US011478134B2

(12) United States Patent
Uchida et al.

(10) Patent No.: US 11,478,134 B2
(45) Date of Patent: Oct. 25, 2022

(54) STEREOSCOPIC-VISION ENDOSCOPE OPTICAL SYSTEM AND ENDOSCOPE USING THE SAME

(71) Applicant: OLYMPUS CORPORATION, Hachioji (JP)

(72) Inventors: Yoshihiro Uchida, Hachioji (JP); Tsutomu Uzawa, Hidaka (JP)

(73) Assignee: OLYMPUS CORPORATION, Tokyo (JP)

( * ) Notice: Subject to any disclaimer, the term of this patent is extended or adjusted under 35 U.S.C. 154(b) by 570 days.

(21) Appl. No.: 16/574,651

(22) Filed: Sep. 18, 2019

(65) Prior Publication Data
US 2020/0008660 A1 Jan. 9, 2020

Related U.S. Application Data

(63) Continuation of application No. PCT/JP2017/015095, filed on Apr. 13, 2017.

(51) Int. Cl.
*A61B 1/00* (2006.01)
*G02B 30/24* (2020.01)

(52) U.S. Cl.
CPC ...... *A61B 1/00193* (2013.01); *A61B 1/00188* (2013.01); *G02B 30/24* (2020.01)

(58) Field of Classification Search
CPC .............. A61B 1/00193; A61B 1/00188
See application file for complete search history.

(56) References Cited

U.S. PATENT DOCUMENTS

| | | |
|---|---|---|
| 5,557,454 A | 9/1996 | Takahashi |
| 5,743,846 A | 4/1998 | Takahashi et al. |
| 5,971,915 A | 10/1999 | Yamamoto et al. |

(Continued)

FOREIGN PATENT DOCUMENTS

| | | |
|---|---|---|
| JP | H07035989 A | 2/1995 |
| JP | H07261094 A | 10/1995 |

(Continued)

OTHER PUBLICATIONS

International Preliminary Report on Patentability (IPRP) dated Oct. 24, 2019 (and English translation thereof) issued in International Application No. PCT/JP2017/015095.

(Continued)

*Primary Examiner* — Brian T Pendleton
*Assistant Examiner* — Frank Johnson
(74) *Attorney, Agent, or Firm* — Holtz, Holtz & Volek PC

(57) ABSTRACT

A stereoscopic-vision endoscope optical system includes a pair of objective optical systems, a pair of relay optical systems, and a pair of image forming optical systems. The image forming optical system includes a first lens unit, a first optical-path bending element, and a second optical-path bending element. The objective optical system and the relay optical system are disposed in a first optical path. A second optical path is formed between the first optical-path bending element and the second optical-path bending element. A third optical path is formed between the second optical-path bending element and a final image. The second optical path is positioned farther from the central axis, than the first optical path. The third optical path is positioned closer to the central axis, than the second optical path.

20 Claims, 24 Drawing Sheets

(56) References Cited

U.S. PATENT DOCUMENTS

| | | | |
|---|---|---|---|
| 5,976,071 | A | 11/1999 | Sekiya |
| 6,306,082 | B1 | 10/2001 | Takahashi et al. |
| 6,338,711 | B1 | 1/2002 | Sekiya et al. |
| 6,364,888 | B1 | 4/2002 | Niemeyer et al. |
| 6,383,131 | B1 | 5/2002 | Yamamoto et al. |
| 6,396,627 | B1 | 5/2002 | Tachihara et al. |
| 6,414,791 | B1 | 7/2002 | Sugawara |
| 6,517,479 | B1 | 2/2003 | Sekiya |
| 6,720,988 | B1 | 4/2004 | Gere et al. |
| 6,976,956 | B2 | 12/2005 | Takahashi et al. |
| 7,564,619 | B2 | 7/2009 | Uzawa et al. |
| 8,149,270 | B1* | 4/2012 | Yaron .................. H04N 13/229 348/45 |
| 8,221,304 | B2 | 7/2012 | Shioda et al. |
| 8,345,084 | B2 | 1/2013 | Namii et al. |
| 8,648,896 | B2 | 2/2014 | Takahashi |
| 8,743,185 | B2 | 6/2014 | Yamaguchi et al. |
| 8,934,169 | B2 | 1/2015 | Mirlay |
| 10,274,717 | B2 | 4/2019 | Togino |
| 2001/0055062 | A1 | 12/2001 | Shioda et al. |
| 2002/0055795 | A1 | 5/2002 | Niemeyer et al. |
| 2002/0082476 | A1 | 6/2002 | Takahashi et al. |
| 2003/0029463 | A1 | 2/2003 | Niemeyer |
| 2005/0020876 | A1 | 1/2005 | Shioda et al. |
| 2005/0027397 | A1 | 2/2005 | Niemeyer |
| 2006/0092273 | A1 | 5/2006 | Gere et al. |
| 2006/0146009 | A1 | 7/2006 | Syrbe et al. |
| 2006/0274433 | A1 | 12/2006 | Kamo |
| 2007/0058249 | A1* | 3/2007 | Hirose .................. H04N 13/239 348/E13.058 |
| 2007/0285508 | A1 | 12/2007 | Gere et al. |
| 2008/0174861 | A1 | 7/2008 | Uzawa et al. |
| 2010/0208046 | A1 | 8/2010 | Takahashi |
| 2012/0008194 | A1 | 1/2012 | Mizuta et al. |
| 2012/0075448 | A1* | 3/2012 | Namii ................. A61B 1/00193 359/462 |
| 2012/0113233 | A1 | 5/2012 | Yamaguchi et al. |
| 2012/0300033 | A1* | 11/2012 | Singh .................... G03B 15/05 348/45 |
| 2013/0044369 | A1 | 2/2013 | Mirlay |
| 2013/0070123 | A1 | 3/2013 | Imoka |
| 2013/0113891 | A1 | 5/2013 | Mayhew et al. |
| 2013/0242412 | A1 | 9/2013 | Uchida et al. |
| 2014/0210945 | A1* | 7/2014 | Morizumi ............ H04N 13/239 348/45 |
| 2014/0300711 | A1 | 10/2014 | Kroon et al. |
| 2014/0375870 | A1* | 12/2014 | Kawamura .... G02B 15/144511 359/680 |
| 2015/0036146 | A1 | 2/2015 | Staloff |
| 2015/0168710 | A1* | 6/2015 | Zobel ................. A61B 1/00193 348/45 |
| 2015/0173846 | A1* | 6/2015 | Schneider .......... G02B 27/0101 600/424 |
| 2016/0131869 | A1 | 5/2016 | Liao et al. |
| 2016/0266370 | A1 | 9/2016 | Uchida et al. |
| 2016/0320606 | A1 | 11/2016 | Togino |
| 2017/0168264 | A1 | 6/2017 | Chen et al. |
| 2017/0235123 | A1 | 8/2017 | Kamo |
| 2017/0251196 | A1* | 8/2017 | Kiniwa ................ H04N 13/218 |
| 2018/0120554 | A1 | 5/2018 | Fukushima |
| 2018/0231748 | A1 | 8/2018 | Chang et al. |
| 2020/0018935 | A1 | 1/2020 | Uchida |
| 2020/0093356 | A1* | 3/2020 | Nishimura ........... A61B 1/0005 |
| 2020/0107707 | A1 | 4/2020 | Uchida |

FOREIGN PATENT DOCUMENTS

| | | |
|---|---|---|
| JP | H07261099 A | 10/1995 |
| JP | H08304714 A | 11/1996 |
| JP | H116967 A | 1/1999 |
| JP | 2001075011 A | 3/2001 |
| JP | 2002011022 A | 1/2002 |
| JP | 3283084 B2 | 3/2002 |
| JP | 2008170803 A | 7/2008 |
| JP | 4750175 B2 | 8/2011 |
| JP | 2012113281 A | 6/2012 |
| JP | 2013524285 A | 6/2013 |
| JP | 2014110910 A | 6/2014 |
| JP | 2014160240 A | 9/2014 |
| JP | 2014174390 A | 9/2014 |
| WO | 2011049195 A1 | 4/2011 |
| WO | 2017033234 A1 | 3/2017 |

OTHER PUBLICATIONS

Related U.S. Appl. No. 16/583,057; First Named Inventor: Yoshihiro Uchida; Title:"Optical System for Stereoscopic Vision and Endoscope Using the Same"; Filed: Sep. 25, 2019.

Related U.S. Appl. No. 16/706,324; First Named Inventor: Yoshihiro Uchida; Title: "Optical System for Stereoscopic Vision and Image Pickup Apparatus Using the Same"; Filed: Dec. 6, 2019.

Related U.S. Appl. No. 16/745,733; First Named Inventor: Yoshihiro Uchida; Title: "Optical System for Stereoscopic Vision and Image Pickup Apparatus Using the Same"; Filed: Jan. 17, 2020.

International Search Report (ISR) (and English language translation thereof) dated Jul. 11, 2017 issued in International Application No. PCT/JP2017/015095.

Written Opinion dated Jul. 11, 2017 issued in International Application No. PCT/JP2017/015095.

Notice of Allowance dated Jul. 28, 2021 issued in related U.S. Appl. No. 16/745,733.

Office Action (Non-Final Rejection) dated Sep. 2, 2020 issued in related U.S. Appl. No. 16/706,324.

* cited by examiner

FIG. 19A
AS
FIY 2.53
FIG. 19B
DT
FIY 2.53
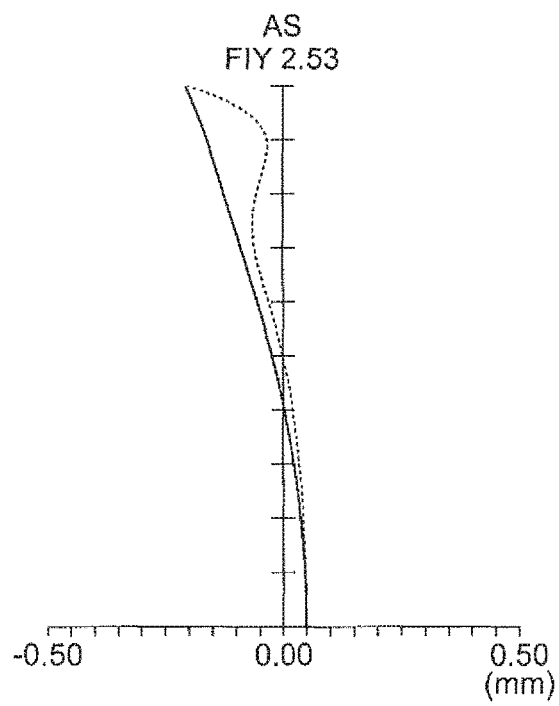
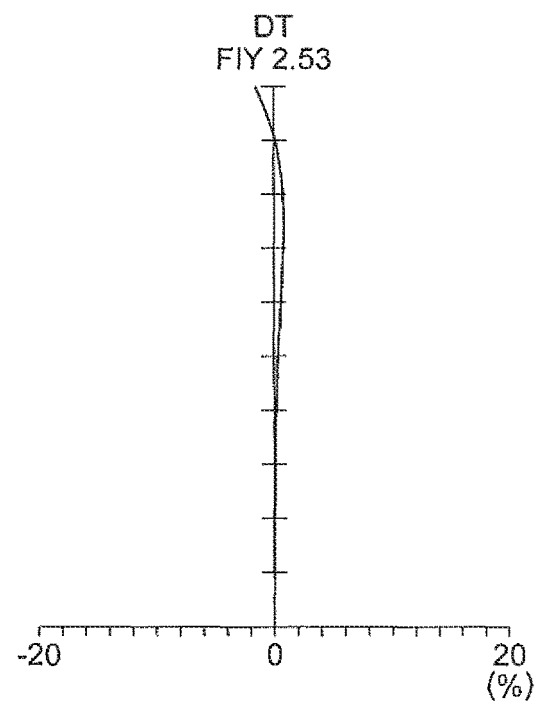
FIG. 19C
Ta, IH 0.0
ey
FIG. 19D
Sa, IH 0.0
ex
FIG. 19E
Ta, IH 0.5
ey
FIG. 19F
Sa, IH 0.5
ex
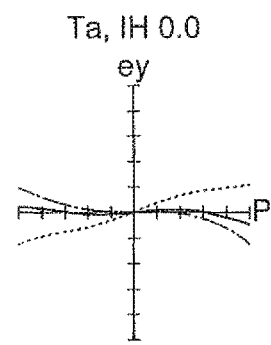
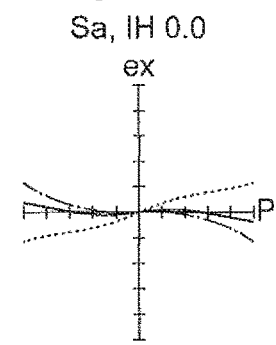
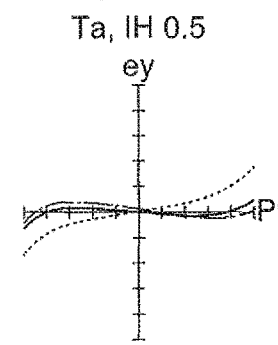
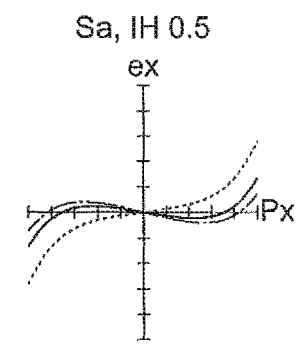
FIG. 19G
Ta, IH 0.7
ey
FIG. 19H
Sa, IH 0.7
ex
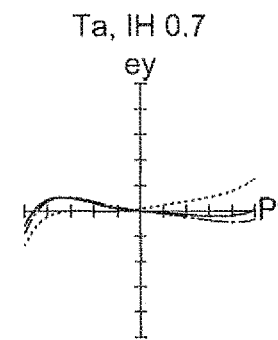
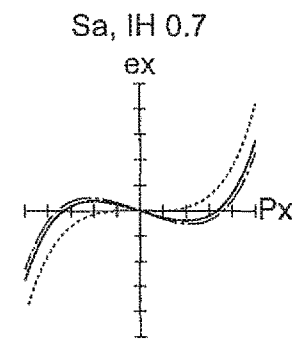

AS
FIY 2.08

DT
FIY 2.08

Ta, IH 0.0

Sa, IH 0.0

Ta, IH 0.5

Sa, IH 0.5

Ta, IH 0.7

Sa, IH 0.7

AS
FIY 2.37

DT
FIY 2.37

Ta, IH 0.0

Sa, IH 0.0

Ta, IH 0.5

Sa, IH 0.5

Ta, IH 0.7

Sa, IH 0.7

AS
FIY 2.36

DT
FIY 2.36

Ta, IH 0.0

Sa, IH 0.0

Ta, IH 0.5

Sa, IH 0.5

Ta, IH 0.7

Sa, IH 0.7

AS
FIY 2.33

DT
FIY 2.33

Ta, IH 0.0

Sa, IH 0.0

Ta, IH 0.5

Sa, IH 0.5

Ta, IH 0.7

Sa, IH 0.7

STEREOSCOPIC-VISION ENDOSCOPE OPTICAL SYSTEM AND ENDOSCOPE USING THE SAME

CROSS-REFERENCE TO RELATED APPLICATION

The present application is a continuation application of International Application No. PCT/JP2017/015095 filed on Apr. 13, 2017, the entire contents of which are incorporated herein by reference.

BACKGROUND OF THE INVENTION

Field of the Invention

The present invention relates to a stereoscopic-vision endoscope optical system, and an endoscope using the same.

Description of the Related Art

As an optical system to be used in a stereoscopic-vision endoscope for medical use, an optical system equipped with an objective optical system and a relay optical system has hitherto been known. In this optical system, an objective lens is disposed at a front end of an insertion portion of an endoscope. The relay optical system is also disposed in the insertion portion, and relays an image of the objective optical system. An image relayed is transmitted to an optical system such as an image forming optical system provided outside the insertion portion.

In Japanese Patent Application Laid-open Publication No. Hei 7-35989, an optical system to be used in a stereoscopic-vision endoscope has been disclosed. In this optical system, two optical systems including an objective optical system, a relay optical system, and an image forming optical system are used. Two final images are formed at two different positions by the two optical systems.

In the optical system disclosed in Japanese Patent Application Laid-open Publication No. Hei 7-35989, a reflecting member is disposed on an image side of the relay optical system, and a distance between optical axes of the two optical systems is widened. Accordingly, observation or acquisition of an image with a high resolution can be performed in wide range of an object space.

In optical systems of examples of Japanese Patent Application Laid-open Publication No. Hei 7-35989, in order to realize small-sizing, an anamorphic optical system is disposed on an image side of the relay optical system. By the anamorphic optical system, an imaging magnification in a parallax direction is made smaller than an imaging magnification in a direction perpendicular to the parallax direction.

SUMMARY OF THE INVENTION

A stereoscopic-vision endoscope optical system according to at least some embodiments of the present invention comprises:
a first optical system, and
a second optical system, wherein
the first optical system and the second optical system are identical optical systems,
a first optical path, a second optical path, and a third optical path are formed in each of the first optical system and the second optical system,
each of the first optical system and the second optical system includes in order from an object side, an objective optical system, a relay optical system, and an image forming optical system,
the image forming optical system includes a first lens unit, a first optical-path bending element, and a second optical-path bending element,
a final image of an object is formed by the image forming optical system,
the objective optical system and the relay optical system are disposed in the first optical path,
the second optical path is formed between the first optical-path bending element and the second optical-path bending element,
the third optical path is formed between the second optical-path bending element and the final image,
the first optical-path bending element has a first reflecting surface disposed in the first optical path and a second reflecting surface disposed in the second optical path,
the second optical-path bending element has a third reflecting surface disposed in the second optical path and a fourth reflecting surface disposed in the third optical path,
a first optical axis of the first optical system, a second optical axis of the first optical system, a third optical axis of the first optical system, a first optical axis of the second optical system, a second optical axis of the second optical system, and at third optical axis of the second optical system are all positioned in the same plane, and
the following conditional expressions (1) and (2) are satisfied:

$$D1 < D2 \quad (1)$$

$$D3 < D2 \quad (2)$$

where,
D1 denotes a distance between the first optical axis of the first optical system and the first optical axis of the second optical system,
D2 denotes a distance between the second optical axis of the first optical system and the second optical axis of the second optical system, and
D3 denotes a distance between the third optical axis of the first optical system and the third optical axis of the second optical system, and here
the first optical axis of the first optical system is an optical axis of the first optical path of the first optical system,
the second optical axis of the first optical system is an optical axis of the second optical path of the first optical system,
the third optical axis of the first optical system is an optical axis of the third optical path of the first optical system,
the first optical axis of the second optical system is an optical axis of the first optical path of the second optical system,
the second optical axis of the second optical system is an optical axis of the second optical path of the second optical system,
the third optical axis of the second optical system is an optical axis of the third optical path of the second optical system, and
the unit of distance is millimeter.

An endoscope according to at least some embodiments of the present invention comprises:
the abovementioned stereoscopic-vision endoscope optical system, and
an imager configured to pick up a final image.

BRIEF DESCRIPTION OF THE DRAWINGS

FIG. 19A, FIG. 19B, FIG. 19C, FIG. 19D, FIG. 19E, FIG. 19F, FIG. 19G, and FIG. 19H are aberration diagrams of the optical system for endoscope according to the example 2;

DETAILED DESCRIPTION OF THE INVENTION

Figure 1:
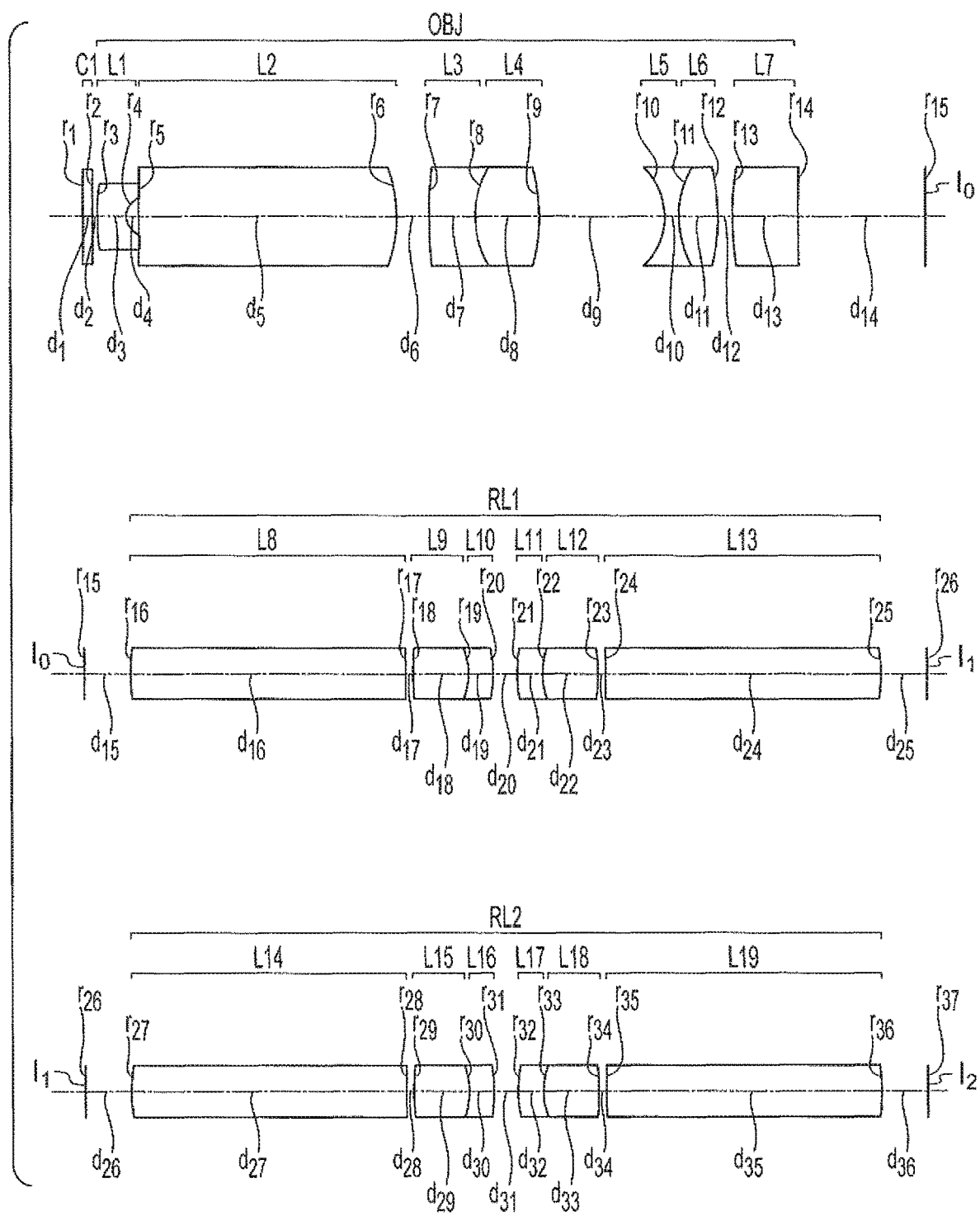
FIG. 1 is a lens cross-sectional view of an optical system for endoscope according to an example 1.

Prior to the explanation of examples, action and effect of embodiments according to certain aspects of the present invention will be described below. In the explanation of the action and effect of the embodiments concretely, the explanation will be made by citing concrete examples. However, similar to a case of the examples to be described later, aspects exemplified thereof are only some of the aspects included in the present invention, and there exists a large number of variations in these aspects. Consequently, the present invention is not restricted to the aspects that will be exemplified.

To start with, a stereoscopic-vision endoscope optical system having an arrangement common to three embodiments (hereinafter, referred to as 'stereoscopic-vision endoscope optical system according to the present embodiment') will be described below. Next, a stereoscopic-vision endoscope optical system according to a first embodiment, a stereoscopic-vision endoscope optical system according to a second embodiment, and a stereoscopic-vision endoscope optical system according to a third embodiment will be described.

The stereoscopic-vision endoscope optical system according to the present embodiment includes a first optical system and a second optical system, wherein the first optical system and the second optical system are identical optical systems, a first optical path, a second optical path, and a third optical path are formed in each of the first optical system and the second optical system, each of the first optical system and the second optical system includes in order from an object side, an objective optical system, a relay optical system, and an image forming optical system, the image forming optical system includes a first lens unit, a first optical-path bending element, and a second optical-path bending element, a final image of an object is formed by the image forming optical system, the objective optical system and the relay optical system are disposed in the first optical path, the second optical path is formed between the first optical-path bending element and the second optical-path bending element, the third optical path is formed between second optical-path bending element and the final image, the first optical-path bending element has a first reflecting surface disposed in the first optical path and a second reflecting surface disposed in the second optical path, the second optical-path bending element has a third reflecting surface disposed in the second optical path and a fourth reflecting surface disposed in the third optical path, a first optical axis of the first optical system, a second optical axis of the first optical system, a third optical axis of the first optical system, a first optical axis of the second optical system, a second optical axis of the second optical system, and a third optical axis of the second optical system are all positioned in the same plane, and the following conditional expressions (1) and (2) are satisfied:

$$D1 < D2 \qquad (1)$$

$$D3 < D2 \qquad (2)$$

where,

D1 denotes a distance between the first optical axis of the first optical system and the first optical axis of the second optical system, D2 denotes a distance between the second optical axis of the first optical system and the second optical axis of the second optical system, and D3 denotes a distance between the third optical axis of the first optical system and the third optical axis of the second optical system, and here the first optical axis of the first optical system is an optical axis of the first optical path of the first optical system, the second optical axis of the first optical system is an optical axis of the second optical path of the first optical system, the third optical axis of the first optical system is an optical axis of the third optical path of the first optical system, the first optical axis of the second optical system is an optical axis of the first optical path of the second optical system, the second optical axis of the second optical system is an optical axis of the second optical path of the second optical system, the third optical axis of the second optical system is an optical axis of the third optical path of the second optical system, and the unit of distance is millimeter.

The stereoscopic-vision endoscope optical system of the present embodiment includes the first optical system and the second optical system. The first optical system and the second optical system are the identical optical systems, and are disposed in parallel.

The first optical path, the second optical path, and the third optical path are formed in each of the first optical system and the second optical system. Each of the first optical system and the second optical system includes in order from the object side, the objective optical system, the relay optical system, and the image forming optical system.

The image forming optical system includes the first lens unit, the first optical-path bending element, and the second optical-path bending element. The final image of an object is formed by the image forming optical system.

As mentioned above, the first optical system and the second optical system are identical optical systems and are disposed in parallel. Therefore, identical final images are formed to be parallel. By observing or picking up the two final images formed in parallel, it is possible to view an object stereoscopically.

In the stereoscopic-vision endoscope optical system of the present embodiment, the objective optical system and the relay optical system are disposed in the first optical path. The second optical path is formed between the first optical-path bending element and the second optical-path bending element. The third optical path is formed between the second optical-path bending element and the final image.

The first optical-path bending element has the first reflecting surface disposed in the first optical path and the second reflecting surface disposed in the second optical path. The second optical-path bending element has the third reflecting surface disposed in the second optical path and the fourth reflecting surface disposed in the third optical path.

The first optical system and the second optical system are disposed in parallel. Therefore, the first optical axis of the first optical system, the second optical axis of the first optical system, the third optical axis of the first optical system, the first optical axis of the second optical system, the second optical axis of the second optical system, and the third optical axis of the second optical system are all positioned in the same plane.

An axis about which the first optical axis of the first optical system and the first optical axis of the second optical system are symmetric is a central axis. The central axis is also positioned in the same abovementioned plane.

For making the stereoscopic-vision endoscope optical system small-sized, narrowing a distance between the first optical system and the second optical system is effective.

However, in a case in which the objective optical system, the relay optical system, and the image forming optical system are disposed on a same straight line, when the distance between the first optical system and the second optical system is narrowed, the two final images come closer mutually. For preventing the two final images from overlapping, a size of the final images has to be made small. As a result, it becomes difficult to form the final images with a high resolution. Moreover, even when the final images are picked up, it becomes difficult to acquire an image with a high resolution.

In the stereoscopic-vision endoscope optical system, conditional expressions (1) and (2) are satisfied.

By satisfying conditional expression (1), the second optical axis is positioned farther from the central axis, than the first optical axis. In other words, the second optical path is positioned farther from the central axis, than the first optical path. Moreover, the second reflecting surface is positioned farther from the central axis, than the first reflecting surface.

Therefore, light incident on the first reflecting surface from the relay optical system is reflected in a direction away from the central axis. Light reflected at the first reflecting surface is incident on the second reflecting surface disposed in the second optical path. Light reflected at the second reflecting surface is incident on the third reflecting surface disposed in the second optical path.

By satisfying conditional expression (2), the third optical axis is positioned closer to the central axis, than the second optical axis. In other words, the third optical path is positioned closer to the central axis from the second optical path. Moreover, the fourth reflecting surface is positioned closer to the central axis, than the third reflecting surface.

Therefore, light incident on the third reflecting surface is reflected in a direction approaching the central axis. Light reflected at the third reflecting surface is incident on the fourth reflecting surface disposed in the third optical path. Light reflected at the fourth reflecting surface travels along the third optical path.

In such manner, in the stereoscopic-vision endoscope optical system of the present embodiment, light in the first optical system and light in the second optical system are reflected to move away mutually by the first reflecting surface. Therefore, it is possible to enlarge a size of the final image up to a size having a high resolution.

Furthermore, light in the first optical system and the light in the second optical system are reflected at the third reflecting surface to come closer mutually. Accordingly, it is possible to bring the final image having a size with a high resolution as close as possible to the central axis. Consequently, in a case of picking up the final image by an imager, it is possible to make a size of the imager small.

As a result, it is possible to realize a stereoscopic-vision endoscope optical system having a high resolution while being small-sized.

In the stereoscopic-vision endoscope optical system of the present embodiment, it is preferable that the following conditional expression (3) be satisfied:

$$0.01 \leq |div1r|/Yimgh \leq 1.5 \qquad (3)$$

where, div1r denotes a distance between the first optical axis and a center of the final image, and Yimgh denotes a height of the final image in the parallax direction, and here the parallax direction is a direction orthogonal to both the first optical axis of the first optical system and the first optical axis of the second optical system.

By satisfying conditional expression (3), it is possible to secure appropriately a distance between the two final images while forming the final images having a high resolution.

In the stereoscopic-vision endoscope optical system of the first embodiment, it is preferable that the image forming optical system include in order from the object side, the first optical-path bending element, the first lens unit, the second optical-path bending element, and a second lens unit, each of the first lens unit and the second lens unit have a positive refractive power, and the following conditional expressions (4), (5), and (6) be satisfied:

$$\beta h \leq -1 \quad (4)$$

$$\beta v \leq -1 \quad (5)$$

$$0.9 \leq \beta h / \beta v \leq 1.1 \quad (6)$$

where,

βh denotes a combined magnification of the first lens unit and the second lens unit in a first direction, and βv denotes a combined magnification of the first lens unit and the second lens unit in a second direction, and here the first direction is a parallax direction, the second direction is a direction perpendicular to the parallax direction, and the parallax direction is a direction orthogonal to both the first optical axis of the first optical system and the first optical axis of the second optical system.

A magnification of the image forming optical system is determined essentially by the combined magnification of the first lens unit and the second lens unit. By satisfying conditional expressions (4) and (5), it is possible to make the magnification of the image forming optical system an enlarged magnification. As a result, it is possible to form the final image with a high resolution. Moreover, by picking up the final image, it is possible to acquire a high-resolution image.

The first lens unit is disposed on an image side of the first optical-path bending element. By imparting a positive refractive power to the first lens unit, even in a case in which the size of the final images is made large, it is possible to make small a diameter of a light beam emerged from the first lens unit. The second optical-path bending element is disposed on the image side of the first lens unit. Therefore, it is possible to make small a diameter of a light beam incident on the second optical-path bending element.

As mentioned above, the third optical path is positioned closer to the central axis, than the second optical path. In such manner, in the third optical path, it is possible to narrow a distance between the third optical axis of the first optical system and the third optical axis of the second optical system by the second optical-path bending element.

In the stereoscopic-vision endoscope optical system of the first embodiment, the second lens unit is disposed in the third optical path. Moreover, in a case of picking up the final image by the imager, the imager is disposed in the third optical path. Consequently, in the stereoscopic-vision endoscope optical system of the first embodiment, it is possible to make both the second lens unit and the imager small-sized.

In the stereoscopic-vision endoscope optical system of the first embodiment, it is preferable that the second optical-path bending element be a prism having a surface of incidence and a surface of emergence, light reaching the second optical-path bending element travel in order through the surface of incidence, the third reflecting surface, the fourth reflecting surface, and the surface of emergence, and the following conditional expression (7) be satisfied:

$$0.8 \leq \Phi pri2in / \Phi pri2ex \leq 1.3 \quad (7)$$

where,

Φpri2in denotes an effective diameter of the surface of incidence of the second optical-path bending element, and Φpri2ex denotes an effective diameter of the surface of emergence of the second optical-path bending element.

By making so as not to exceed an upper limit value of conditional expression (7), it is possible to prevent a diameter of a light beam incident on the second optical-path bending element from becoming excessively large. Consequently, it is possible to make small a size of the third reflecting surface and a size of the fourth reflecting surface, as well as to make small the distance between the third reflecting surface and the fourth reflecting surface.

By making so as not to fall below a lower limit value of conditional expression (7), it is possible to maintain the diameter of the light beam incident on the second lens unit small. Consequently, it is possible to correct an aberration favorably while preventing interference of the second lens unit of the first optical system and the second lens unit of the second optical system. The interference of the two lens units refers to a contact between the two lens units.

In the stereoscopic-vision endoscope optical system of the second embodiment, it is preferable that the image forming optical system include in order from the object side, the first lens unit, the first optical-path bending element, the second optical-path bending element, and a second lens unit, each of the first lens unit and the second lens unit have a positive refractive power, and conditional expressions (4), (5), and (6) be satisfied.

The magnification of the image forming optical system is determined essentially by the combined magnification of the first lens unit and the second lens unit. By satisfying conditional expressions (4) and (5), it is possible to make the magnification of the image forming optical system an enlarged magnification. As a result, it is possible to form the final image with a high resolution. Moreover, by picking up the final image, it is possible to acquire a high-resolution image.

The first lens unit is disposed on the object side of the first optical-path bending element. By imparting a positive refractive power to the first lens unit, even in a case in which the size of the final image is made large, it is possible to make small a diameter of a light beam emerged from the first lens unit. The first optical-path bending element and the second optical-path bending element are disposed on the image side of the first lens unit. Therefore, it is possible to make small a diameter of a light beam incident on the first optical-path bending element and the second optical-path bending element.

As mentioned above, the third optical path is positioned closer to the central axis, than the second optical path. In such manner, in the third optical path, it is possible to narrow a distance between the third optical axis of the first optical system and the third optical axis of the second optical system by the second optical-path bending element.

In the stereoscopic-vision endoscope optical system of the second embodiment, the second lens unit is disposed in the third optical path. Moreover, in a case of picking up the final image by the imager, the imager is disposed in the third optical path. Consequently, in the stereoscopic-vision endoscope optical system of the second embodiment, it is possible to make both the second lens unit and the imager small-sized.

In the stereoscopic-vision endoscope optical system of the second embodiment, it is preferable that the first optical-path bending element be a prism having a surface of incidence and a surface of emergence, the second optical-path bending element is a prism having a surface of incidence and a surface of emergence, light reaching the first optical-path bending element travel in order through the surface of incidence of the first optical-path bending element, the first reflecting surface, the second reflecting surface, and the surface of emergence of the first optical-path bending element, light reaching the second optical-path bending element travel in order through the surface of incidence of the second optical-path bending element, the third reflecting surface, the fourth reflecting surface, and the surface of emergence of the second optical-path bending element, and the following conditional expression (8) be satisfied:

$$0.3 \leq \Phi pri1in/\Phi pri2ex \leq 1.3 \tag{8}$$

where, $\Phi pri1in$ denotes an effective diameter of the surface of incidence of the first optical-path bending element, and $\Phi pri2ex$ denotes an effective diameter of the surface of emergence of the second optical-path bending element.

By making so as not to exceed an upper limit value of conditional expression (8), it is possible to prevent the diameter of the light beam incident on the second optical-path bending element from becoming excessively large. Consequently, it is possible make the second optical-path bending element small-sized without a light ray at the third reflecting surface and the fourth reflecting surface being vignetted.

By making so as not to fall below a lower limit value of conditional expression (8), it is possible to maintain the diameter of the light beam incident on the second lens unit small. Consequently, it is possible to correct an aberration favorably while preventing interference of the second lens unit of the first optical system and the second lens unit of the second optical system.

In the stereoscopic-vision endoscope optical system of the first embodiment, it is preferable that the following conditional expression (9) be satisfied:

$$0.8 \leq DG2b/FLG2 \leq 1.5 \tag{9}$$

where,

DG2b denotes a distance from an image-side principal point of the second lens unit up to the final image, and FLG2 denotes a focal length of the second lens unit.

The final image has various spatial frequency components from a low spatial frequency component to a high spatial frequency component. In an optical system, due to an effect of diffraction, resolution in a spatial frequency component on a high-frequency side is deteriorated. In order to realize small-sizing of the optical system while preventing the deterioration of resolution, it is necessary to make the diameter of the second lens unit small while making an F-number small. By making so as not to exceed an upper limit value of conditional expression (9), it is possible to make the F-number small while maintaining a lens diameter of the second lens unit small.

In a case of falling below a lower limit value of conditional expression (9), the distance from the image-side principal point of the second lens unit up to the final image becomes small with respect to the focal length of the second lens unit. In this case, the refractive power of the first lens unit has to be made large. As the refractive power of the first lens unit is made large, an aberration in susceptible to occur.

By making so as not to fall below a lower limit value of conditional expression (9), it is possible to suppress more favorably occurrence of a spherical aberration and occurrence of a coma while maintaining appropriate the refractive power of the first lens unit.

In the stereoscopic-vision endoscope optical system of the second embodiment, it is preferable that conditional expression (9) be satisfied.

When the F-number becomes large, the resolution in the spatial frequency component on the high-frequency side is degraded due to the effect of diffraction. By making so as not to exceed the upper limit value of conditional expression (9), it is possible to prevent the F-number from becoming large. As a result, it is possible to prevent the degradation of resolution in the spatial frequency component on the high-frequency side due to the effect of diffraction.

By making so as not to fall below the lower limit value of conditional expression (9), it is possible to prevent the diameter of a light beam in the image forming optical system from becoming large. Consequently, it is possible make the first optical-path bending element and the second optical-path bending element small-sized.

In the stereoscopic-vision endoscope optical system of the first embodiment, it is preferable that the following conditional expression (10) be satisfied:

$$0.02 \leq Yimg/FLG2 \leq 0.2 \tag{10}$$

where,

Yimg denotes the maximum height of the final image, and

FLG2 denotes the focal length of the second lens unit.

By making so as not to exceed an upper limit value of conditional expression (10), it is possible to maintain the refractive power of the second lens unit appropriate. As a result, it is possible to suppress more favorably occurrence of various aberrations such as the occurrence of the spherical aberration and the occurrence of the coma.

In a case in which the focal length of the second lens unit becomes long, the refractive power of the first lens unit has to be made large. As the refractive power of the first lens unit is made large, an aberration is susceptible to occur.

By making so as not to fall below a lower limit value of conditional expression (10), it is possible to maintain the refractive power of the first lens unit appropriate. As a result, it is possible to suppress more favorably the occurrence of various aberrations such as the occurrence of the spherical aberration and the occurrence of the coma.

In the stereoscopic-vision endoscope optical system of the second embodiment, it is preferable that conditional expression (10) is satisfied.

By making so as not to exceed the upper limit value of conditional expression (10) or so as not to fall below the lower limit value of conditional expression (10), it is possible to secure an appropriate back focus.

In the stereoscopic-vision endoscope optical system of the third embodiment, it is preferable that the image forming optical system include in order from the object side, the first optical-path bending element, the first lens unit, and the second optical-path bending element, the first lens unit have a positive refractive power, and the following conditional expressions (11), (12), and (13) be satisfied:

$$\beta G1h \leq -1 \tag{11}$$

$$\beta G1v \leq -1 \tag{12}$$

$$0.9 \leq \beta G1h/\beta G1v \leq 1.1 \tag{13}$$

where, $\beta G1h$ denotes a magnification of the first lens unit in a first direction, and βG1v denotes a magnification of the first lens unit in a second direction, and here the first direction is the parallax direction, the second direction is a direction perpendicular to the parallax direction, and the parallax direction is a direction orthogonal to both the first optical axis of the first optical system and the first optical axis of the second optical system.

The magnification of the image forming optical system is determined by the magnification of the first lens unit. By satisfying conditional expressions (11) and (12), it is possible to make the magnification of the image forming optical system an enlarged magnification. As a result, it is possible to form the final image with a high resolution. Moreover, by picking up the final image, it is possible to acquire a high-resolution image.

The first lens unit is disposed on the image side of the first optical-path bending element. By imparting a positive refractive power to the first lens unit, even in a case in which the size of the final image is made large, it is possible to make small a diameter of a light beam emerged from the first lens unit. The second optical-path bending element is disposed on the image side of the first lens unit. Consequently, it is possible to make small a diameter of a light beam incident on the second optical-path bending element.

As mentioned above, the third optical path is positioned closer to the central axis, than the second optical path. In such manner, in the third optical path, it is possible to narrow a distance between the third optical axis of the first optical system and the third optical axis of the second optical system by the second optical-path bending element.

In a case of picking up the final image by the imager, the imager is disposed in the third optical path. Consequently, in the stereoscopic-vision endoscope optical system of the third embodiment, it is possible to make the imager small-sized.

In the stereoscopic-vision endoscope optical system of the first embodiment, it is preferable that an intermediate image of an object be formed on an image side of the relay optical system, and the following conditional expression (14) be satisfied:

$$0.6 \leq DG1f/FLG1 \leq 1.2 \tag{14}$$

where,

DG1f denotes a distance from an object-side principal point of the first lens unit up to the intermediate image, and FLG1 denotes a focal length of the first lens unit.

By making so as not to exceed an upper limit value of conditional expression (14), it is possible to maintain the refractive power of the first lens unit appropriate. As a result, it is possible to suppress a height of a light ray incident on the second optical-path bending element to be small while suppressing the spherical aberration and the coma.

By making so as not to fall below a lower limit value of conditional expression (14), it is possible to suppress a light ray emerged from the first lens unit from being diverged. The second optical-path bending element is disposed on the image side of the first lens unit. Since a light ray suppressed from being diverged is incident on the second optical-path bending element, it is possible prevent the second optical-path bending element from becoming large in size.

In the stereoscopic-vision endoscope optical system of the second embodiment, it is preferable that an intermediate image of an object be formed on the image side of the relay optical system, and conditional expression (14) be satisfied.

The first optical-path bending element and the second optical-path bending element are disposed on the image side of the first lens unit. It is necessary to dispose the first lens unit such that the second optical-path bending element does not become large in size, while maintaining an optical-path length of the first optical-path bending element and an optical-path length of the second optical-path bending element appropriate.

By making so as not to exceed the upper limit value of conditional expression (14), it is possible to make light emerged from the first lens unit incident on the second lens unit, in a state of the optical-path length of the first optical-path bending element and the optical-path length of the second optical-path bending element maintained appropriate. Consequently, it is possible to secure a high resolution while maintaining the refractive power of the second lens unit favorable.

By making so as not to fall below a lower limit value of conditional expression (14), it is possible to prevent a light ray emerged from the first lens unit from being diverged. The first optical-path bending element and the second optical-path bending element are disposed on the image side of the first lens unit. Since a light ray suppressed from being diverged is incident on the first optical-path bending element and the second optical-path bending element, it is possible to prevent each of the first optical-path bending element and the second optical-path bending element from becoming large in size.

In the stereoscopic-vision endoscope optical system of the first embodiment, it is preferable that the following conditional expression (15) be satisfied:

$$0 < Yimg/FLG1 \leq 0.3 \tag{15}$$

where,

Yimg denotes the maximum height of the final image, and

FLG1 denotes the focal length of the first lens unit.

By making so as not to exceed an upper limit value of conditional expression (15), it is possible to maintain the refractive power of the first lens unit appropriate. As a result, it is possible to suppress even more favorably an occurrence of various aberrations, and particularly, the occurrence of the spherical aberration and the occurrence of the coma.

By making so as not to fall below a lower limit value of conditional expression (15), it is possible to prevent a diameter of a light beam incident on the second optical-path bending element from becoming excessively large. Consequently, it is possible make small a size of the third reflecting surface and a size of the fourth reflecting surface, as well as to make small a distance between the third reflecting surface and the fourth reflecting surface.

In the stereoscopic-vision endoscope optical system of the second embodiment, it is preferable that conditional expression (15) be satisfied.

By making so as not to exceed the upper limit value of conditional expression (15), it is possible maintain a diameter of a light beam emerging from the second optical-path bending element appropriate.

By making so as not to fall below the lower limit value of conditional expression (15), it is possible to maintain the diameter of the light beam incident on the second optical-path bending element appropriate. Consequently, it is possible to make small a size of the second optical-path bending element.

In the stereoscopic-vision endoscope optical system of the third embodiment, it is preferable that conditional expression (15) be satisfied.

By making so as not to exceed the upper limit value of conditional expression (15) or so as not to fall below the lower limit value of conditional expression (15), it is possible to make the image forming optical system small-sized.

In the stereoscopic-vision endoscope objective optical system of the first embodiment, the stereoscopic-vision endoscope optical system of the second embodiment, and the stereoscopic-vision endoscope optical system of the third embodiment, it is preferable that the following conditional expression (16) be satisfied:

$$0.3 \leq Dax1/(\Phi r\,\max + Dax1) \leq 0.8 \quad (16)$$

where,

Dax1 denotes a distance between the first optical axis of the first optical system and the first optical axis of the second optical system, and Φr max denotes the maximum lens diameter in the relay optical system.

By making so as not to exceed an upper limit value of conditional expression (16), it is possible to secure adequately a diameter of an axial light beam. Consequently, it is possible to maintain a high resolution in the spatial frequency component on the high-frequency side.

By making so as not to fall below a lower limit value of conditional expression (16), it is possible secure adequately an amount of parallax while maintaining a lens diameter of the relay optical system appropriate.

In the stereoscopic-vision endoscope optical system of the first embodiment, the stereoscopic-vision endoscope optical system of the second embodiment, and the stereoscopic-vision endoscope optical system of the third embodiment, it is preferable that an image of an object be formed on the object side of the relay optical system by the objective optical system, and the following conditional expression (17) be satisfied:

$$1.0 \leq \Phi r\,\max/Ymidimg \leq 5.0 \quad (17)$$

where,

Φr max denotes the maximum lens diameter in the relay optical system, and

Ymidimg denotes the maximum height of the image of the object.

An image of an object is formed on the object side of the relay optical system by the objective optical system. The image of the object is relayed by the relay optical system. An intermediate image is formed on the image side of the relay optical system.

Conditional expression (17) is a favorable conditional expression related to the relay optical system. When a barrel-shape distortion occurs largely, it becomes difficult to achieve a high resolution in a peripheral portion of the final image. Therefore, it is necessary to suppress the barrel-shape distortion to be small.

By making so as not to exceed an upper limit value of conditional expression (17), it is possible to maintain the distortion in particular, appropriate, while maintaining an outer diameter and an angle of view sought for the stereoscopic-vision endoscope optical system.

By making so as not to fall below a lower limit value of conditional expression (17), it is possible to suppress vignetting of an off-axis subordinate light ray. By suppressing the vignetting of the off-axis subordinate light ray, it is possible to maintain a high resolution even in the peripheral portion of the final image. Moreover, in a case of having picked up the final image, it is possible to maintain a high resolution up to a high spatial frequency component even in a periphery of an image picked up.

In the stereoscopic-vision endoscope optical system of the first embodiment, the stereoscopic-vision endoscope optical system of the second embodiment, and the stereoscopic-vision endoscope optical system of the third embodiment, it is preferable that the first lens unit include a movable lens unit, and focusing be carried out by moving the movable lens unit.

By making such arrangement, even when an object is positioned anywhere between a near point and a far point, it is possible to form the final image with a high resolution. Moreover, by picking up the final image, it is possible to acquire an image with a high resolution.

In the stereoscopic-vision endoscope optical system of the first embodiment and the stereoscopic-vision endoscope optical system of the second embodiment, it is preferable that the second lens unit include a movable lens unit, and focusing be carried out by moving the movable lens unit.

By making such arrangement, even when an object is positioned anywhere between a near point and a far point, it is possible to form the final image with a high resolution. Moreover, by picking up the final image, it is possible to acquire an image with a high resolution.

An endoscope of the present embodiment includes the abovementioned stereoscopic-vision endoscope optical system and an imager configured to pick up a final image.

According to the endoscope of the present embodiment, it is possible to acquire an image with a high resolution by picking up the final image, while being small-sized.

For each conditional expression, the lower limit value or the upper limit value may be changed as follows.

For conditional expression (3), it is preferable that the lower limit value be either 0.10 or 0.20, and it is preferable that the upper limit value be either 1.00 or 0.80.

For conditional expression (4), it is preferable that the lower limit vale be either −1.70 or −1.60, and it is preferable that the upper limit value be either −1.05 or −1.10.

For conditional expression (5), it is preferable that the lower limit value be either −1.70 or −1.60, and it is preferable that the upper limit value be either −1.05 or −1.10.

For conditional expression (6), it is preferable that the lower limit value be either 0.95 or 0.99, and it is preferable that the upper limit value be either 1.05 or 1.01.

For conditional expression (7), it is preferable that the lower limit value be either 0.90 or 0.95, and it is preferable that the upper limit value be either 1.20 or 1.10.

For conditional expression (8), it is preferable that the lower limit value be either 0.4 or 0.5, and it is preferable that the upper limit value be either 1.2 or 1.1.

For conditional expression (9), it is preferable that the lower limit value be either 0.90 or 0.95, and it is preferable that the upper limit value be either 1.40 or 1.30.

For conditional expression (10), it is preferable that the lower limit value be either 0.05 or 0.07, and it is preferable that the upper limit value be either 0.14 or 0.12.

For conditional expression (11), it is preferable that the lower limit value be either −1.5 or −1.3, and it is preferable that the upper limit value be either −1.01 or −1.02.

For conditional expression (12), it is preferable that the lower limit value be either −1.5 or −1.3, and it is preferable that the upper limit value be either −1.01 or −1.02.

For conditional expression (13), it is preferable that the lower limit value be either 0.95 or 0.99, and it is preferable that the upper limit value be either 1.05 or 1.01.

For conditional expression (14), it is preferable that the lower limit value be either 0.70 or 0.80, and it is preferable that the upper limit value be either 1.10 or 1.05.

For conditional expression (15), it is preferable that the lower limit value be either 0.02 or 0.08, and it is preferable that the upper limit value be either 0.20 or 0.15.

For conditional expression (16), it is preferable that the lower limit value be either 0.4 or 0.5, and it is preferable that the upper limit value be either 0.7 or 0.6.

For conditional expression (17), it is preferable that the lower limit value be either 2.0 or 3.1, and it is preferable that the upper limit value be either 4.0 or 2.3.

Examples of stereoscopic-vision endoscope optical system will be described below in detail by referring to the accompanying diagrams. However, the present invention is not restricted to the embodiments and the examples described below.

Examples of the stereoscopic-vision endoscope optical system will be described below. FIG. 1, FIG. 2, FIG. 3, FIG. 4, FIG. 5, FIG. 6, FIG. 7, FIG. 8, FIG. 9, FIG. 10, FIG. 11, FIG. 12, FIG. 13, FIG. 14, FIG. 15, FIG. 16, and FIG. 17 are lens cross-sectional views of stereoscopic-vision endoscope optical systems of respective examples. The lens cross-sectional views are cross-sectional views in the parallax direction.

Aberration diagrams of the examples are as follows.

FIG. 18A, FIG. 19A, FIG. 20A, FIG. 21A, FIG. 22A, and FIG. 23A show an astigmatism (AS), FIG. 18B, FIG. 19B, FIG. 20B, FIG. 21B, FIG. 22B, and FIG. 23B show a distortion (DT).

FIG. 18C, FIG. 19C, FIG. 20C, FIG. 21C, FIG. 22C, FIG. 23C, FIG. 18D, FIG. 19D, FIG. 20D, FIG. 21D, FIG. 22D, FIG. 23D, FIG. 18E, FIG. 19E, FIG. 20E, FIG. 21E, FIG. 22E, FIG. 23E, FIG. 18F, FIG. 19F, FIG. 20F, FIG. 21F, FIG. 22F, FIG. 23F, FIG. 18G, FIG. 19G, FIG. 20G, FIG. 21G, FIG. 22G, FIG. 23G, FIG. 18H, FIG. 19H, FIG. 20H, FIG. 21H, FIG. 22H, and FIG. 23H show a transverse aberration.

In the transverse aberration, the maximum value of the horizontal axis is ±50 µm. A vertical axis is normalized by an entrance-pupil diameter. Ta denotes a tangential direction and Sa denotes a sagittal direction. Moreover, IH 0 denotes an axial, IH 0.5 denotes 0.5 times of the maximum image height, and IH 0.7 denotes 0.7 times of the maximum image height.

Figure 2:
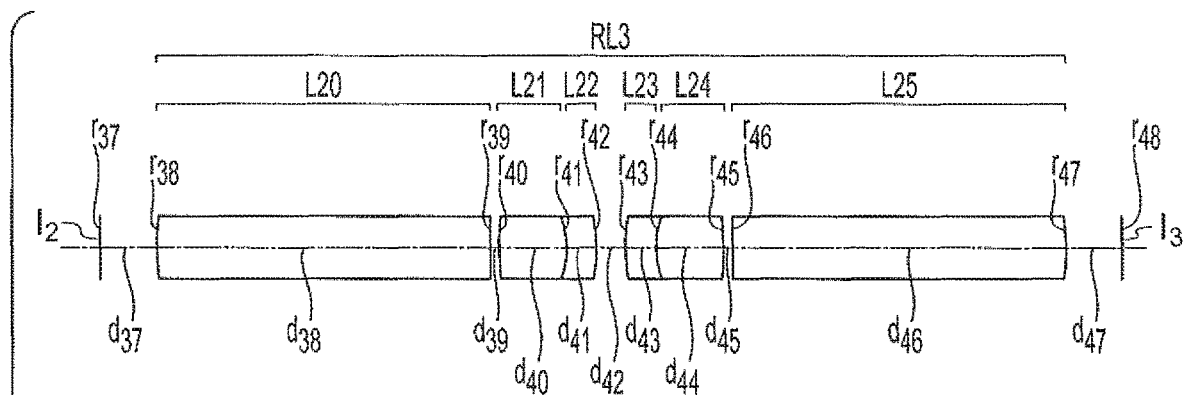
FIG. 2 is a lens cross-sectional view of the optical system for endoscope according to the example 1.
Figure 2:
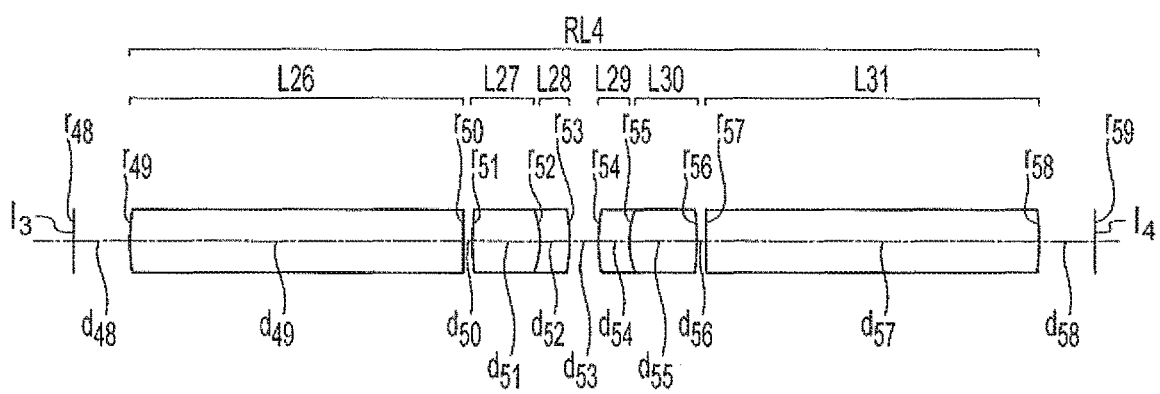
Figure 2:
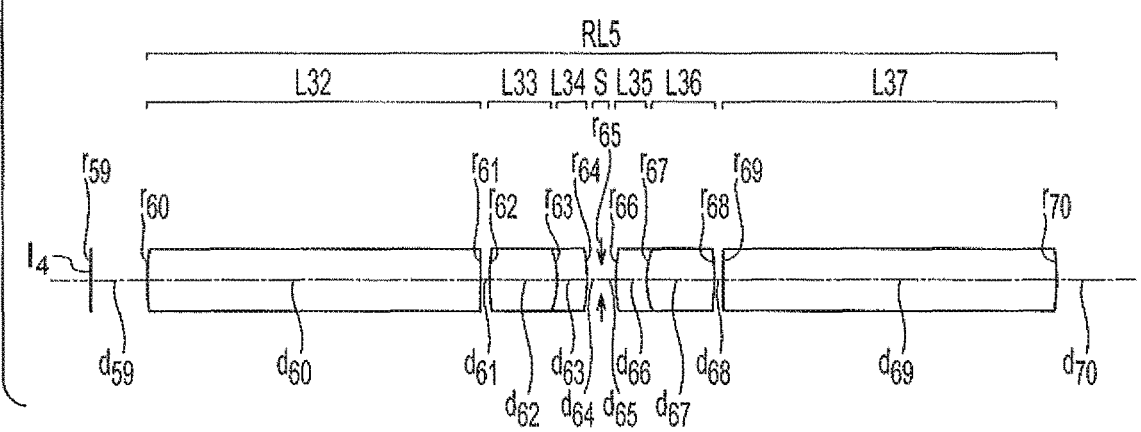
Figure 3:
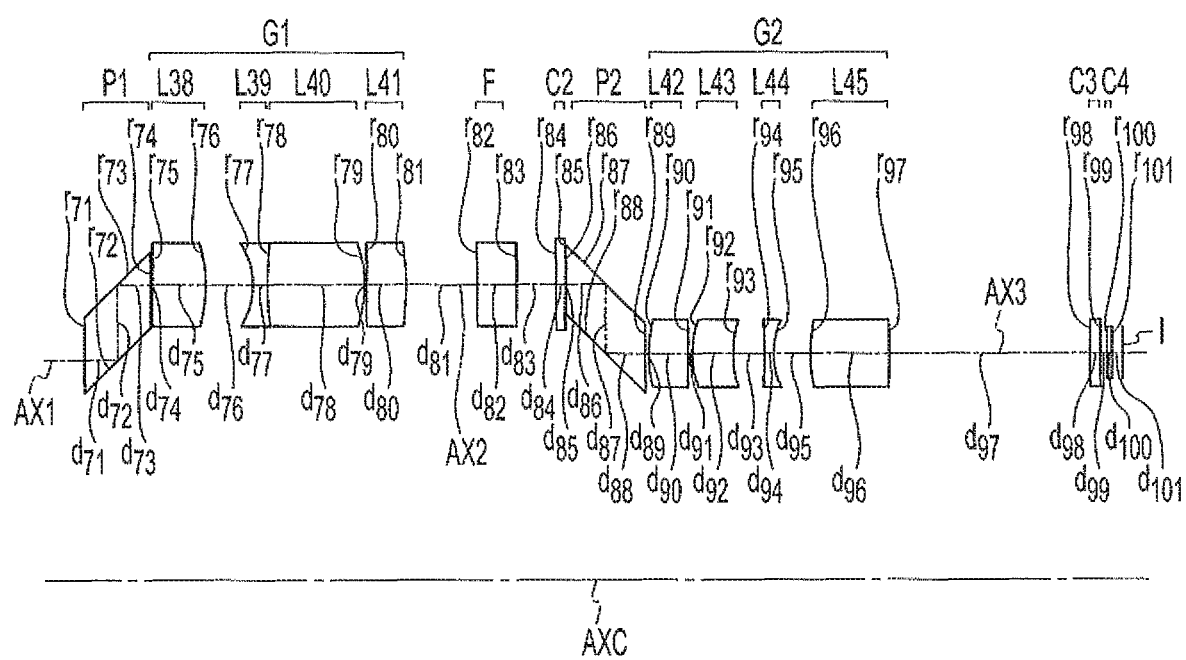
FIG. 3 is a lens cross-sectional view of the optical system for endoscope according to the example 1.

Lens cross-sectional views of a stereoscopic-vision endoscope optical system of an Example 1 are shown in FIG. 1, FIG. 2, and FIG. 3. In FIG. 1, an objective optical system OBJ, a first relay optical system RL1, a second relay optical system RL2 are shown. In FIG. 2, a third relay optical system RL3, a fourth relay optical system RL4, and a fifth relay optical system RL5 are shown. In FIG. 3, an image forming optical system is shown.

The stereoscopic-vision endoscope optical system of the example 1 includes in order from an object side, the objective optical system OBJ, the first relay optical system RL1, the second relay optical system RL2, the third relay optical system RL3, the fourth relay optical system RL4, the fifth relay optical system RL5, and the image forming optical system.

A primary image Io is formed by the objective optical system OBJ. The primary image Io is relayed by the first relay optical system RL1. Accordingly, a first relay image I1 is formed. The first relay image I1 is relayed by the second relay optical system RL2. Accordingly, a second relay image I2 is formed. The second relay image I2 is relayed by the third relay optical system RL3. Accordingly, a third relay image I3 is formed. The third relay image I3 is relayed by the fourth relay optical system RL4. Accordingly, a fourth relay image I4 is formed.

The fourth relay image I4 is relayed by the fifth relay optical system RL5. Accordingly, a fifth relay image is formed, which is not shown in the lens cross-sectional views of the example 1. The fifth relay image is an intermediate image. A final image I is formed by the image forming optical system.

The objective optical system OBJ includes in order from the object side, a planoconcave negative lens L1, a planoconvex positive lens L2, a negative meniscus lens L3 having a convex surface directed toward the object side, a biconvex positive lens L4, a biconcave negative lens L5, a biconvex positive lens L6, and a positive meniscus lens L7 having a convex surface directed toward the object side. Here, the negative meniscus lens L3 and the biconvex positive lens L4 are cemented. The biconcave negative lens L5 and the biconvex positive lens L6 are cemented. A cover glass C1 is disposed on the object side of the planoconcave negative lens L1.

The first relay optical system RL1 includes a planoconvex positive lens L8, a biconvex positive lens L9, a negative meniscus lens L10 having a convex surface directed toward an image side, a negative meniscus lens L11 having a convex surface directed toward the object side, a biconvex positive lens L12, and a planoconvex positive lens L13. Here, the biconvex positive lens L9 and the negative meniscus lens L10 are cemented. The negative meniscus lens L11 and the biconvex positive lens L12 are cemented.

The second relay optical system RL2 includes a planoconvex positive lens L14, a biconvex positive lens L15, a negative meniscus lens L16 having a convex surface directed toward the image side, a negative meniscus lens L17 having a convex surface directed toward the object side, a biconvex positive lens L18, and a planoconvex positive lens L19. Here, the biconvex positive lens L15 and the negative meniscus lens L16 are cemented. The negative meniscus lens L17 and the biconvex positive lens L18 are cemented.

The third relay optical system RL3 includes a planoconvex positive lens L20, a biconvex positive lens L21, a negative meniscus lens L22 having a convex surface directed toward the image side, a negative meniscus lens L23 having a convex surface directed toward the object side, a biconvex positive lens L24, and a planoconvex positive lens L25. Here, the biconvex positive lens L21 and the negative meniscus lens L22 are cemented. The negative meniscus lens L23 and the biconvex positive lens L24 are cemented.

The fourth relay optical system RL4 includes a planoconvex positive lens L26, a biconvex positive lens L27, a negative meniscus lens L28 having a convex surface directed toward the image side, a negative meniscus lens L29 having a convex surface directed toward the object side, a biconvex positive lens L30, and a planoconvex positive lens L31. Here, the biconvex positive lens L27 and the negative meniscus lens L28 are cemented. The negative meniscus lens L29 and the biconvex positive lens L30 are cemented.

The fifth relay optical system RL5 includes a planoconvex positive lens L32, a biconvex positive lens L33, a negative meniscus lens L34 having a convex surface directed toward the image side, a negative meniscus lens L35 having a convex surface directed toward the object side, a biconvex positive lens L36, and a planoconvex positive lens L37. Here, the biconvex positive lens L33 and the negative meniscus lens L34 are cemented. The negative meniscus lens L35 and the biconvex positive lens L36 are cemented.

An aperture stop S is disposed between the negative meniscus lens L34 and the negative meniscus lens L35.

The image forming optical system includes in order from the object side, a prism P1, a first lens unit G1, a prism P2, and a second lens unit G2.

The first lens unit G1 includes a biconvex positive lens L38, a biconcave negative lens L39, a biconvex positive lens L40, and a biconvex positive lens L41. Here, the biconcave negative lens L39 and the biconvex positive lens L40 are cemented. The biconvex positive lens L41 is to be moved for focusing.

The second lens unit G2 includes a biconvex positive lens L42, a positive meniscus lens L43 having a convex surface directed toward the object side, a biconcave negative lens L44, and a biconvex positive lens L45.

The prism P1 is the first optical-path bending element. The prism P1 has a first reflecting surface r72 and a second reflecting surface r73. The prism P2 is the second optical-path bending element. The prism P2 has a third reflecting surface r87 and a fourth reflecting surface r88.

An optical filter F and a plane parallel plate C2 are disposed between the first lens unit G1 and the prism P2. A cover glass C3 and a cover glass C4 are disposed between the second lens unit G2 and the final image I.

An aspheric surface is provided to both surfaces of the planoconcave negative lens L1.

A second optical axis AX2 is positioned farther from a central axis AXc, than a first optical axis AX1. A third optical axis AX3 is positioned closer to the central axis AXc, than the second optical axis AX2.

Figure 4:
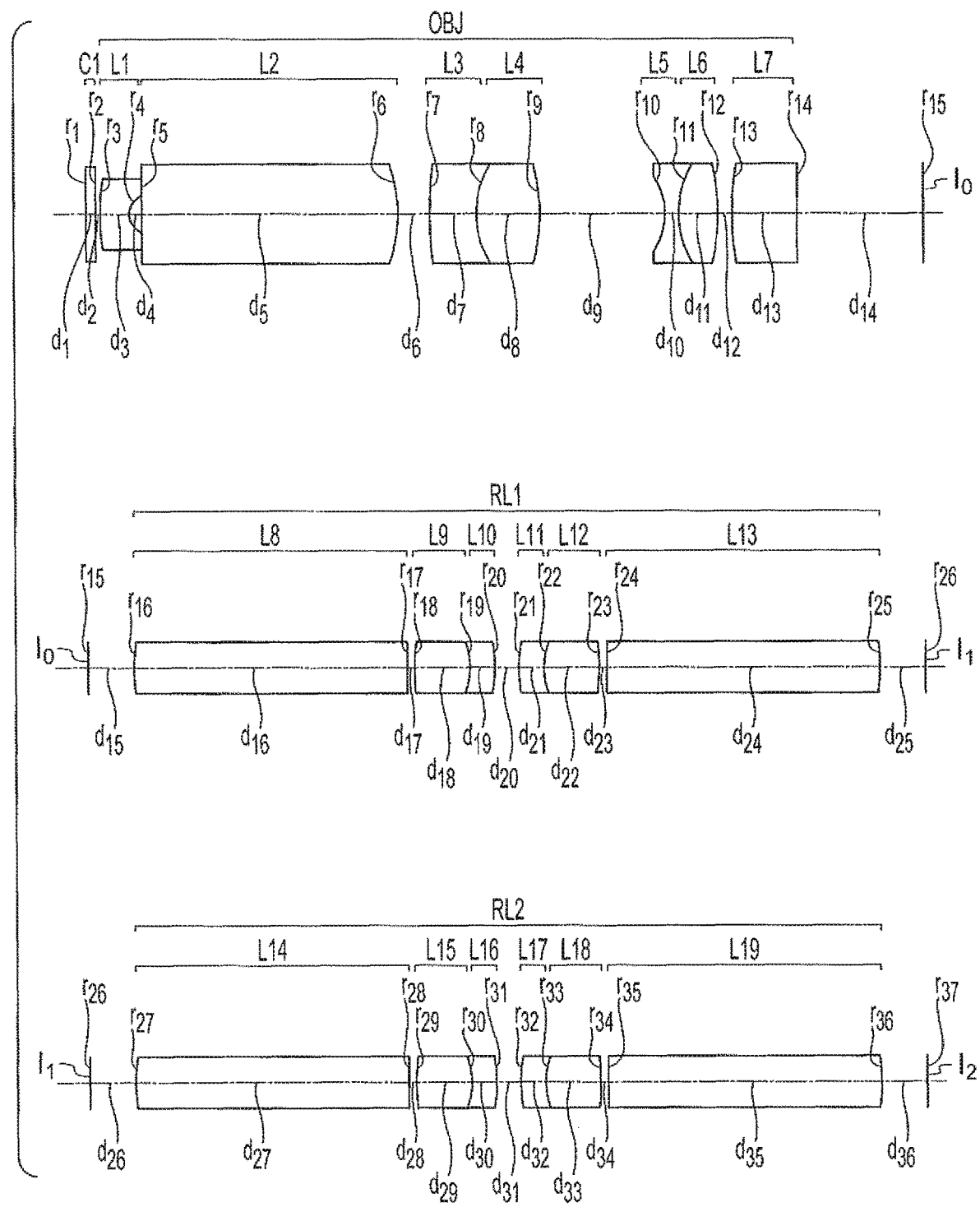
FIG. 4 is a lens cross-sectional view of an optical system for endoscope according to an example 2.
Figure 5:
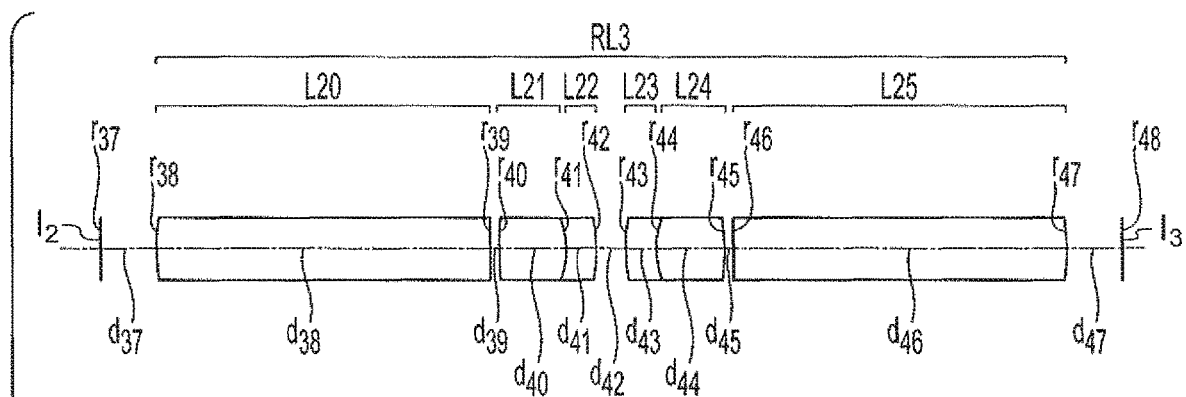
FIG. 5 is a lens cross-sectional view of the optical system for endoscope according to the example 2.
Figure 5:
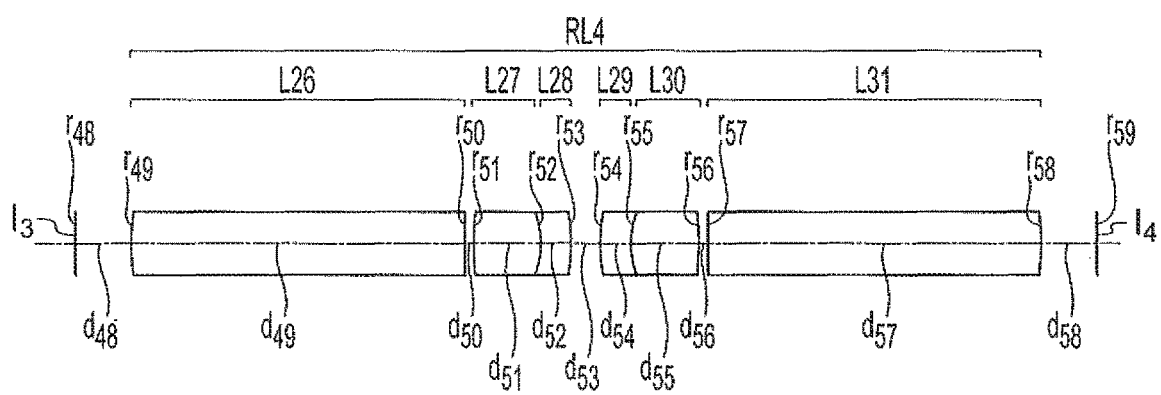
Figure 5:
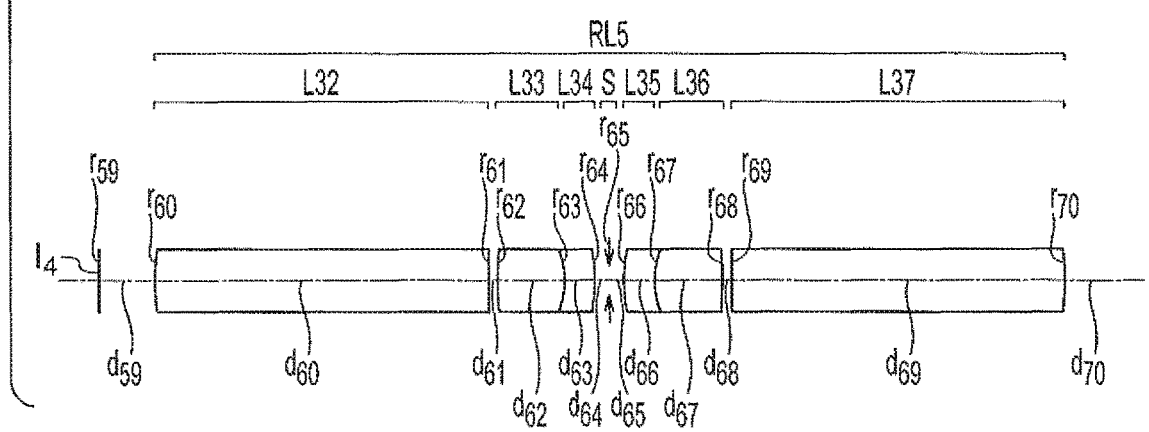
Figure 6:
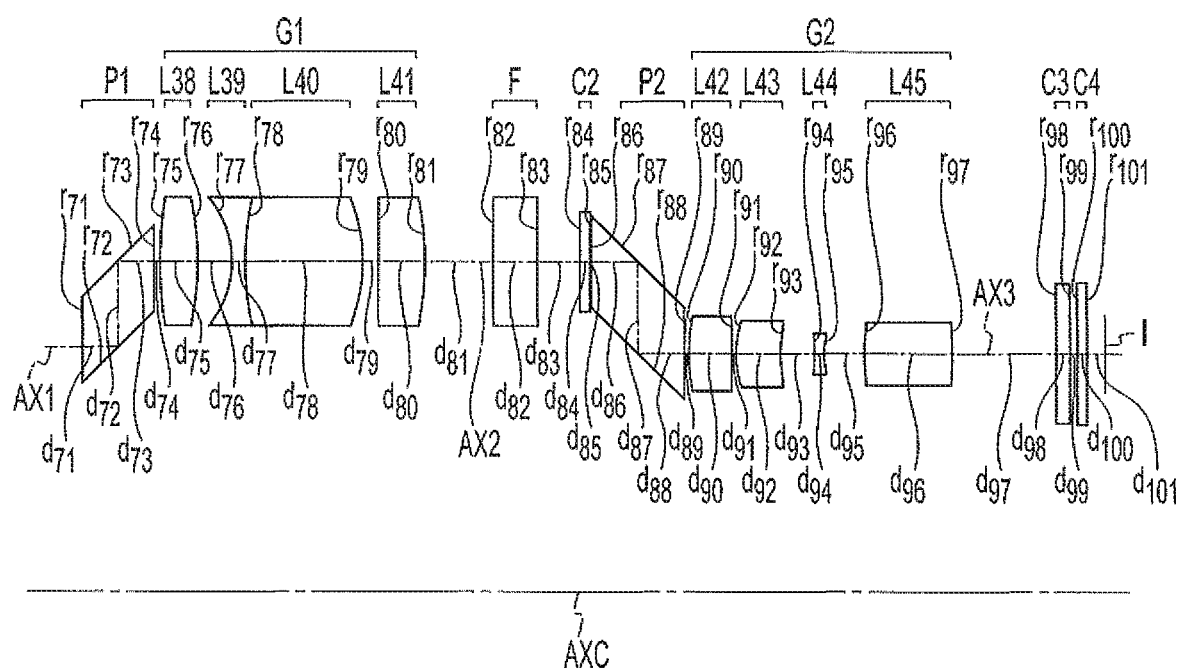
FIG. 6 is a lens cross-sectional view of the optical system for endoscope according to the example 2.

Lens cross-sectional views of a stereoscopic-vision endoscope optical system of an example 2 are shown in FIG. 4, FIG. 5, and FIG. 6. In FIG. 4, an objective optical system OBJ, a first relay optical system RL1, and a second relay optical system RL2 are shown. In FIG. 5, a third relay optical system RL3, a fourth relay optical system RL4, and a fifth relay optical system RL5 are shown. In FIG. 6, an image forming optical system is shown.

The stereoscopic-vision endoscope optical system of the example 2 includes in order from an object side, the objective optical system OBJ, the first relay optical system RL1, the second relay optical system RL2, the third relay optical system RL3, the fourth relay optical system RL4, the fifth relay optical system RL5, and the image forming optical system.

A primary image Io is formed by the objective optical system OBJ. The primary image Io is relayed by the first relay optical system RL1. Accordingly, a first relay image I1 is formed. The first relay image I1 is relayed by the second relay optical system RL2. Accordingly, a second relay image I2 is formed. The second relay image I2 is relayed by the third relay optical system RL3. Accordingly, a third relay image I3 is formed. The third relay image I3 is relayed by the fourth relay optical system RL4. Accordingly, a fourth relay image I4 is formed.

The fourth relay image I4 is relayed by the fifth relay optical system RL5. Accordingly, a fifth relay image is formed, which is not shown in the lens cross-sectional views of the example 2. The fifth relay image is an intermediate image. A final image I is formed by the image forming optical system.

The objective optical system OBJ includes in order from the object side, a planoconcave negative lens L1, a planoconvex positive lens L2, a negative meniscus lens L3 having a convex surface directed toward the object side, a biconvex positive lens L4, a biconcave negative lens L5, a biconvex positive lens L6, and a positive meniscus lens L7 having a convex surface directed toward the object side. Here, the negative meniscus lens L3 and the biconvex positive lens L4 are cemented. The biconcave negative lens L5 and the biconvex positive lens L6 are cemented. A cover glass C1 is disposed on the object side of the planoconcave negative lens L1.

The first relay optical system RL1 includes a planoconvex positive lens L8, a biconvex positive lens L9, a negative meniscus lens L10 having a convex surface directed toward an image side, a negative meniscus lens L11 having a convex surface directed toward the object side, a biconvex positive lens L12, and a planoconvex positive lens L13. Here, the biconvex positive lens L9 and the negative meniscus lens L10 are cemented. The negative meniscus lens L11 and the biconvex positive lens L12 are cemented.

The second relay optical system RL2 includes a planoconvex positive lens L14, a biconvex positive lens L15, a negative meniscus lens L16 having a convex surface directed toward the image side, a negative meniscus lens L17 having a convex surface directed toward the object side, a biconvex positive lens L18, and a planoconvex positive lens L19. Here, the biconvex positive lens L15 and the negative meniscus lens L16 are cemented. The negative meniscus lens L17 and the biconvex positive lens L18 are cemented.

The third relay optical system RL3 includes a planoconvex positive lens L20, a biconvex positive lens L21, a negative meniscus lens L22 having a convex surface directed toward the image side, a negative meniscus lens L23 having a convex surface directed toward the object side, a biconvex positive lens L24, and a planoconvex positive lens L25. Here, the biconvex positive lens L21 and the negative meniscus lens L22 are cemented. The negative meniscus lens L23 and the biconvex positive lens L24 are cemented.

The fourth relay optical system RL4 includes a planoconvex positive lens L26, a biconvex positive lens L27, a negative meniscus lens L28 having a convex surface directed toward the image side, a negative meniscus lens L29 having a convex surface directed toward the object side, a biconvex positive lens L30, and a planoconvex positive lens L31. Here, the biconvex positive lens L27 and the negative meniscus lens L28 are cemented. The negative meniscus lens L29 and the biconvex positive lens L30 are cemented.

The fifth relay optical system RL5 includes a planoconvex positive lens L32, a biconvex positive lens L33, a negative meniscus lens L34 having a convex surface directed toward the image side, a negative meniscus lens L35 having a convex surface directed toward the object side, a biconvex positive lens L36, and a planoconvex positive lens L37. Here, the biconvex positive lens L33 and the negative meniscus lens L34 are cemented. The negative meniscus lens L35 and the biconvex positive lens L36 are cemented.

An aperture stop S is disposed between the negative meniscus lens L34 and the negative meniscus lens L35.

The image forming optical system includes in order from the object side, a prism P1, a first lens unit G1, a prism P2, and a second lens unit G2.

The first lens unit G1 includes a biconvex positive lens L38, a biconcave negative lens L39, a biconvex positive lens L40, and a planoconvex positive lens L41. Here, the biconcave negative lens L39 and the biconvex positive lens L40 are cemented. The planoconvex positive lens L41 is to be moved for focusing.

The second lens unit G2 includes a biconvex positive lens L42, a positive meniscus lens L43 having a convex surface directed toward the object side, a biconcave negative lens L44, and a biconvex positive lens L45.

The prism P1 is the first optical-path bending element. The prism P1 has a first reflecting surface r72 and a second reflecting surface r73. The prism P2 is the second optical-path bending element. The prism P2 has a third reflecting surface r87 and a fourth reflecting surface r88.

An optical filter F and a plane parallel plate C2 are disposed between the first lens unit G1 and the prism P2. A cover glass C3 and a cover glass C4 are disposed between the second lens unit G2 and the final image I.

An aspheric surface is provided to both surfaces of the planoconcave negative lens L1.

A second optical axis AX2 is positioned farther from a central axis AXc, than a first optical axis AX1. A third optical axis AX3 is positioned closer to the central axis AXc, than the second optical axis AX2.

Figure 7:
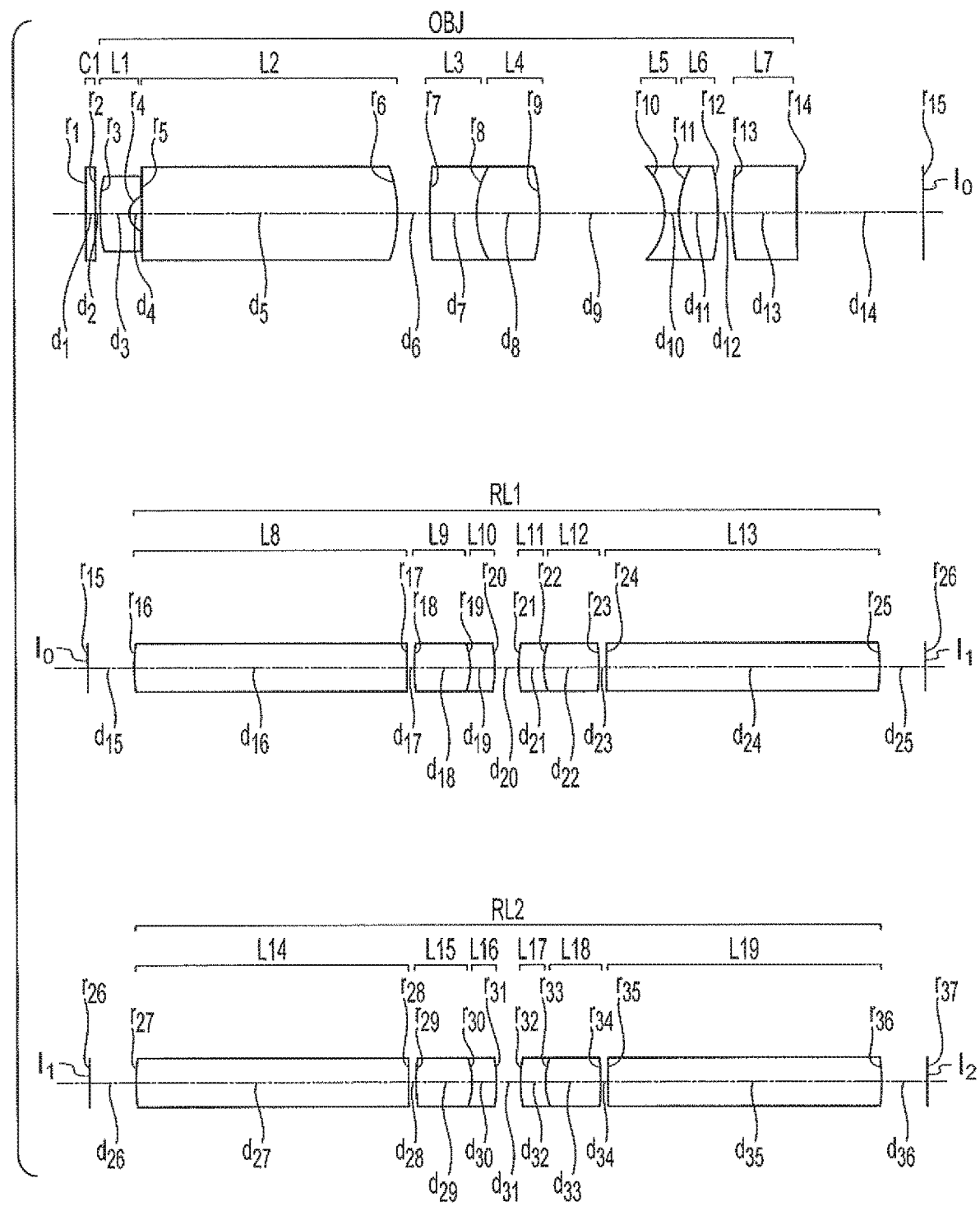
FIG. 7 is a lens cross-sectional view of an optical system for endoscope according to an example 3.
Figure 8:
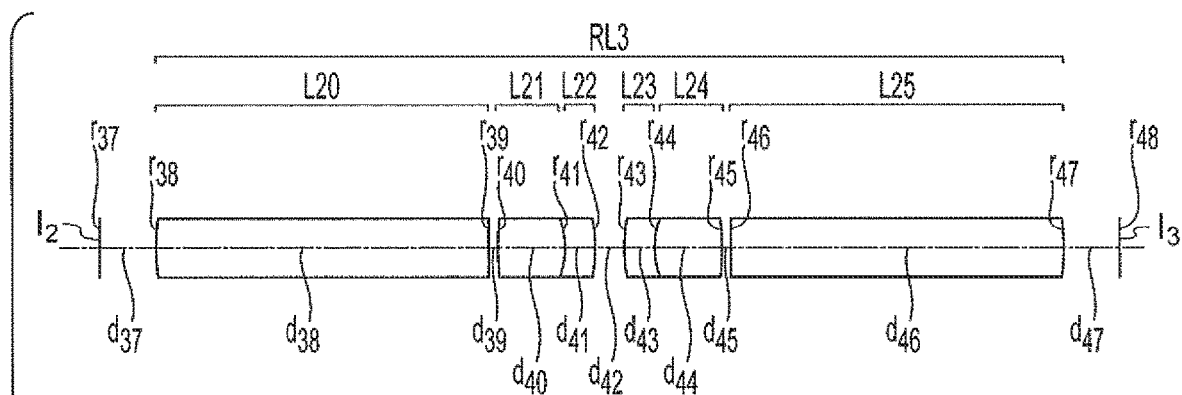
FIG. 8 is a lens cross-sectional view of the optical system for endoscope according to the example 3.
Figure 8:
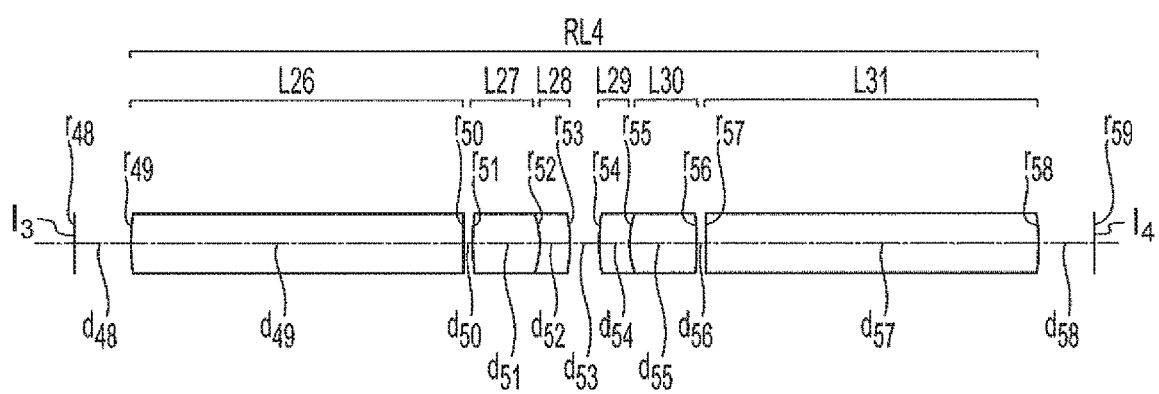
Figure 8:
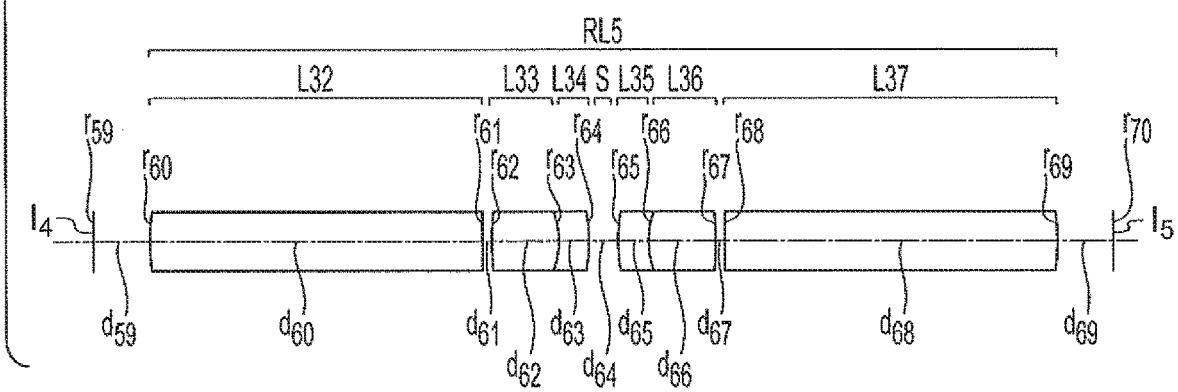
Figure 9:
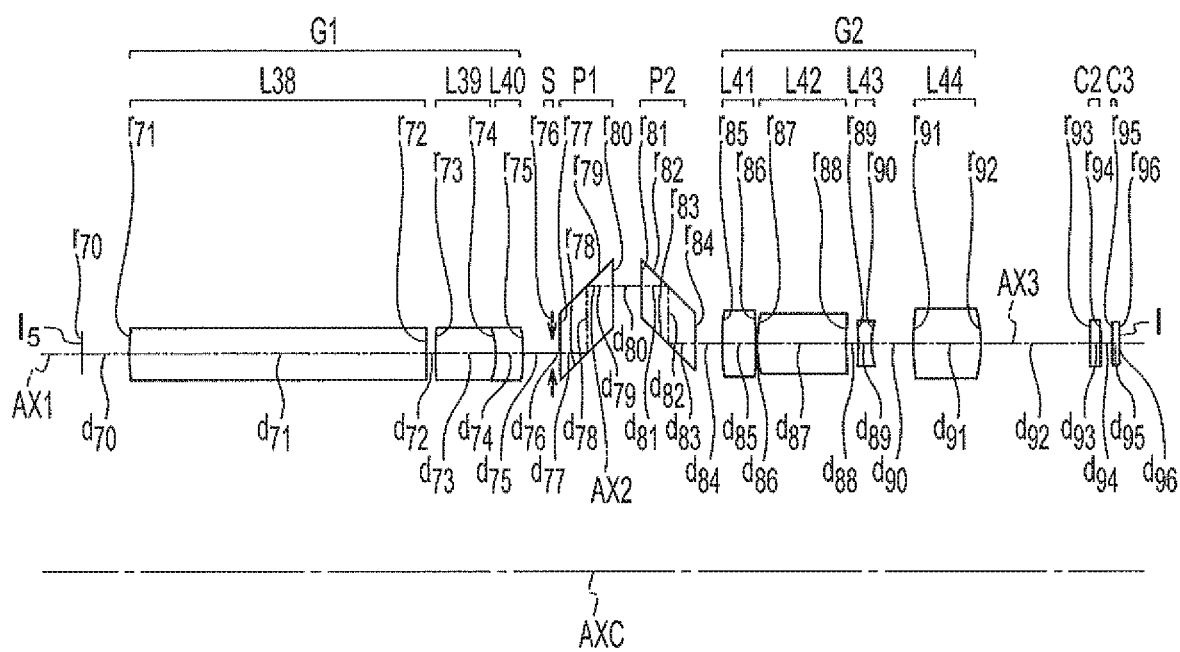
FIG. 9 is a lens cross-sectional view of the optical system for endoscope according to the example 3.

Lens cross-sectional views of a stereoscopic-vision endoscope optical system of an example 3 are shown in FIG. 7, FIG. 8, and FIG. 9. In FIG. 7, an objective optical system OBJ, a first relay optical system RL1, and a second relay optical system RL2 are shown. In FIG. 8, a third relay optical system RL3, a fourth relay optical system RL4, and a fifth relay optical system RL5 are shown. In FIG. 9, an image forming optical system is shown.

The stereoscopic-vision endoscope optical system of the example 3 includes in order from an object side, the objective optical system OBJ, the first relay optical system RL1, the second relay optical system RL2, the third relay optical system RL3, the fourth relay optical system RL4, the fifth relay optical system RL5, and the image forming optical system.

A primary image Io is formed by the objective optical system OBJ. The primary image Io is relayed by the first relay optical system RL1. Accordingly, a first relay image I1 is formed. The first relay image I1 is relayed by the second relay optical system RL2. Accordingly, a second relay image I2 is formed. The second relay image I2 is relayed by the third relay optical system RL3. Accordingly, a third relay image I3 is formed. The third relay image I3 is relayed by the fourth relay optical system RL4. Accordingly, a fourth relay image I4 is formed.

The fourth relay image I4 is relayed by the fifth relay optical system RL5. Accordingly, a fifth relay image I5 is formed. The fifth relay image I5 is an intermediate image. A final image I is formed by the image forming optical system.

The objective optical system OBJ includes in order from the object side, a planoconcave negative lens L1, a planoconvex positive lens L2, a negative meniscus lens L3 having a convex surface directed toward the object side, a biconvex positive lens L4, a biconcave negative lens L5, a biconvex positive lens L6, and a positive meniscus lens L7 having a convex surface directed toward the object side. Here, the negative meniscus lens L3 and the biconvex positive lens L4 are cemented. The biconcave negative lens L5 and the biconvex positive lens L6 are cemented. A cover glass C1 is disposed on the object side of the planoconcave negative lens L1.

The first relay optical system RL1 includes a planoconvex positive lens L8, a biconvex positive lens L9, a negative meniscus lens L10 having a convex surface directed toward an image side, a negative meniscus lens L11 having a convex surface directed toward the object side, a biconvex positive lens L12, and a planoconvex positive lens L13. Here, the biconvex positive lens L9 and the negative meniscus lens L10 are cemented. The negative meniscus lens L11 and the biconvex positive lens L12 are cemented.

The second relay optical system RL2 includes a planoconvex positive lens L14, a biconvex positive lens L15, a negative meniscus lens L16 having a convex surface directed toward the image side, a negative meniscus lens L17 having a convex surface directed toward the object side, a biconvex positive lens L18, and a planoconvex positive lens L19. Here, the biconvex positive lens L15 and the negative meniscus lens L16 are cemented. The negative meniscus lens L17 and the biconvex positive lens L18 are cemented.

The third relay optical system RL3 includes a planoconvex positive lens L20, a biconvex positive lens L21, a negative meniscus lens L22 having a convex surface directed toward the image side, a negative meniscus lens L23 having a convex surface directed toward the object side, a biconvex positive lens L24, and a planoconvex positive lens L25. Here, the biconvex positive lens L21 and the negative meniscus lens L22 are cemented. The negative meniscus lens L23 and the biconvex positive lens L24 are cemented.

The fourth relay optical system RL4 includes a planoconvex positive lens L26, a biconvex positive lens L27, a negative meniscus lens L28 having a convex surface directed toward the image side, a negative meniscus lens L29 having a convex surface directed toward the object side, a biconvex positive lens L30, and a planoconvex positive lens L31. Here, the biconvex positive lens L27 and the negative meniscus lens L28 are cemented. The negative meniscus lens L29 and the biconvex positive lens L30 are cemented.

The fifth relay optical system RL5 includes a planoconvex positive lens L32, a biconvex positive lens L33, a negative meniscus lens L34 having a convex surface directed toward the image side, a negative meniscus lens L35 having a convex surface directed toward the object side, a biconvex positive lens L36, and a planoconvex positive lens L37. Here, the biconvex positive lens L33 and the negative meniscus lens L34 are cemented. The negative meniscus lens L35 and the biconvex positive lens L36 are cemented.

The image forming optical system includes in order from the object side, a first lens unit G1, a prism P1, a prism P2, and a second lens unit G2.

The first lens unit G1 includes a planoconvex positive lens L38, a biconvex positive lens L39, and a negative meniscus lens L40 having a convex surface directed toward the image side. Here, the biconvex positive lens L39 and the negative meniscus lens L40 are cemented.

The second lens unit G2 includes a biconvex positive lens L41, a positive meniscus lens L42 having a convex surface directed toward the object side, a biconcave negative lens L43, and a biconvex positive lens L44. The biconvex positive lens L44 is to be moved for focusing.

The prism P1 is the first optical-path bending element. The prism P1 has a first reflecting surface r78 and a second reflecting surface r79. The prism P2 is the second optical-path bending element. The prism P2 has a third reflecting surface r82 and a fourth reflecting surface r83.

An aperture stop S is disposed between the first lens unit G1 and the prism P1.

A cover glass C2 and a cover glass C3 are disposed between the second lens unit G2 and the final image I.

An aspheric surface is provided to both surfaces of the planoconcave negative lens L1.

A second optical axis AX2 is positioned farther from a central axis AXc, than a first optical axis AX1. A third optical axis AX3 is positioned closer to the central axis AXc, than the second optical axis AX2.

Figure 10:
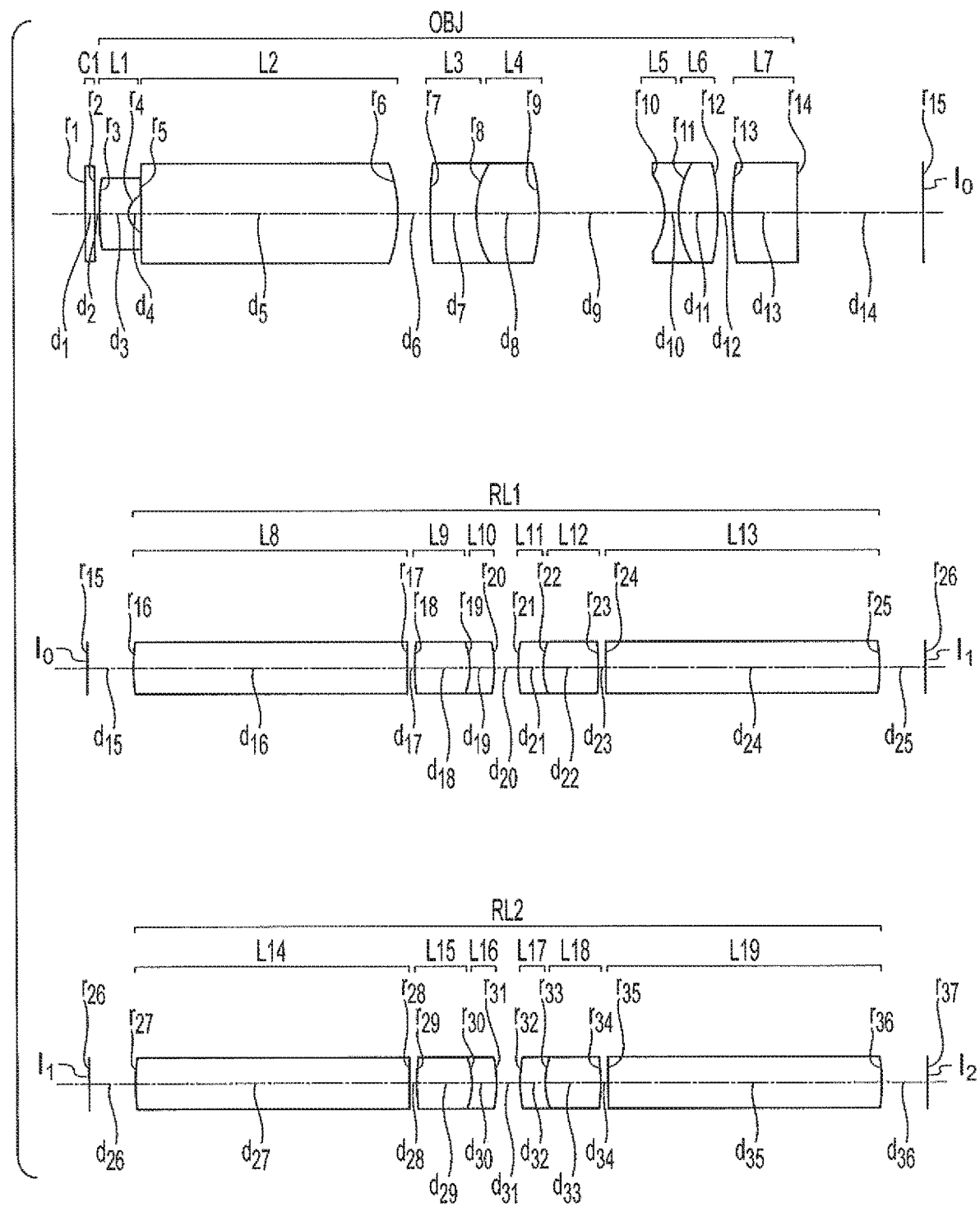
FIG. 10 is a lens cross-sectional view of an optical system for endoscope according to an example 4.
Figure 11:
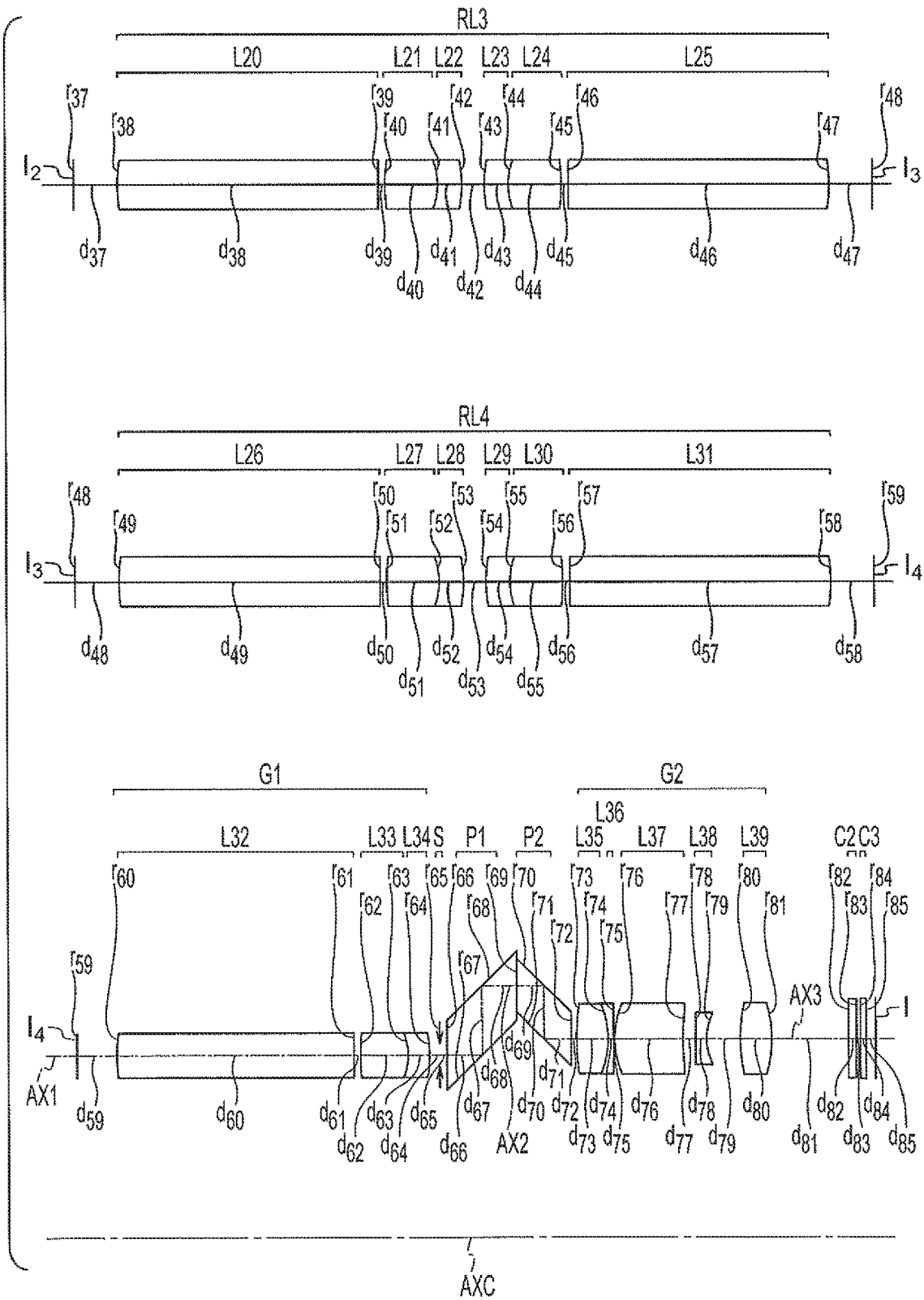
FIG. 11 is lens cross-sectional view of the optical system for endoscope according to the example 4.

Lens cross-sectional views of a stereoscopic-vision endoscope optical system of an example 4 are shown in FIG. 10 and FIG. 11. In FIG. 10, an objective optical system OBJ, a first relay optical system RL1, and a second relay optical system RL2 are shown. In FIG. 11, a third relay optical system RL3, a fourth relay optical system RL4, and an image forming optical system are shown.

The stereoscopic-vision endoscope optical system of the example 4 includes in order from an object side, the objective optical system OBJ, the first relay optical system RL1, the second relay optical system RL2, the third relay optical system RL3, the fourth relay optical system RL4, and the image forming optical system.

A primary image Io is formed by the objective optical system OBJ. The primary image Io is relayed by the first relay optical system RL1. Accordingly, a first relay image I1 is formed. The first relay image I1 is relayed by the second relay optical system RL2. Accordingly, a second relay image I2 is formed. The second relay image I2 is relayed by the third relay optical system RL3. Accordingly, a third relay image I3 is formed.

The third relay image I3 is relayed by the fourth relay optical system RL4. Accordingly, a fourth relay image I4 is formed. The fourth relay image I4 is an intermediate image. A final image I is formed by the image forming optical system.

The objective optical system OBJ includes in order from the object side, a planoconcave negative lens L1, a planoconvex positive lens L2, a negative meniscus lens L3 having a convex surface directed toward the object side, a biconvex positive lens L4, a biconcave negative lens L5, a biconvex positive lens L6, and a positive meniscus lens L7 having a convex surface directed toward the object side. Here, the negative meniscus lens L3 and the biconvex positive lens L4 are cemented. The biconcave negative lens L5 and the biconvex positive lens L6 are cemented. A cover glass C1 is disposed on the object side of the planoconcave negative lens L1.

The first relay optical system RL1 includes a planoconvex positive lens L8, a biconvex positive lens L9, a negative meniscus lens L10 having a convex surface directed toward an image side, a negative meniscus lens L11 having a convex surface directed toward the object side, a biconvex positive lens L12, and a planoconvex positive lens L13. Here, the biconvex positive lens L9 and the negative meniscus lens L10 are cemented. The negative meniscus lens L11 and the biconvex positive lens L12 are cemented.

The second relay optical system RL2 includes a planoconvex positive lens L14, a biconvex positive lens L15, a negative meniscus lens L16 having a convex surface directed toward the image side, a negative meniscus lens L17 having a convex surface directed toward the object side, a biconvex positive lens L18, and a planoconvex positive lens L19. Here, the biconvex positive lens L15 and the negative meniscus lens L16 are cemented. The negative meniscus lens L17 and the biconvex positive lens L18 are cemented.

The third relay optical system RL3 includes a planoconvex positive lens L20, a biconvex positive lens L21, a negative meniscus lens L22 having a convex surface directed toward the image side, a negative meniscus lens L23 having a convex surface directed toward the object side, a biconvex positive lens L24, and a planoconvex positive lens L25. Here, the biconvex positive lens L21 and the negative meniscus lens L22 are cemented. The negative meniscus lens L23 and the biconvex positive lens L24 are cemented.

The fourth relay optical system RL4 includes a planoconvex positive lens L26, a biconvex positive lens L27, a negative meniscus lens L28 having a convex surface directed toward the image side, a negative meniscus lens L29 having a convex surface directed toward the object side, a biconvex positive lens L30, and a planoconvex positive lens L31. Here, the biconvex positive lens L27 and the negative meniscus lens L28 are cemented. The negative meniscus lens L29 and the biconvex positive lens L30 are cemented.

The image forming optical system includes in order from the object side, a first lens unit G1, a prism P1, a prism P2, and a second lens unit G2.

The first lens unit G1 includes a planoconvex positive lens L32, a biconvex positive lens L33, and a negative meniscus lens L34 having a convex surface directed toward the image side. Here, the biconvex positive lens L33 and the negative meniscus lens L34 are cemented.

The second lens unit G2 includes a biconvex positive lens L35, a negative meniscus lens L36 having a convex surface directed toward the image side, a positive meniscus lens L37 having a convex surface directed toward the object side, a biconcave negative lens L38, and a biconvex positive lens L39. Here, the biconvex positive lens L35 and the negative meniscus lens L36 are cemented. The biconvex positive lens L39 is to be moved for focusing.

The prism P1 is the first optical-path bending element. The prism P1 has a first reflecting surface r67 and a second reflecting surface r68. The prism P2 is the second optical-path bending element. The prism P2 has a third reflecting surface r70 and a fourth reflecting surface r71.

An aperture stop S is disposed between the first lens unit G1 and the prism P1.

A cover glass C2 and a cover glass C3 are disposed between the second lens unit G2 and the final image I.

An aspheric surface is provided to both surfaces of the planoconcave negative lens L1.

A second optical axis AX2 is positioned farther from a central axis AXc, than a first optical axis AX1. A third optical axis AX3 is positioned closer to the central axis AXc, than the second optical axis AX2.

Figure 12:
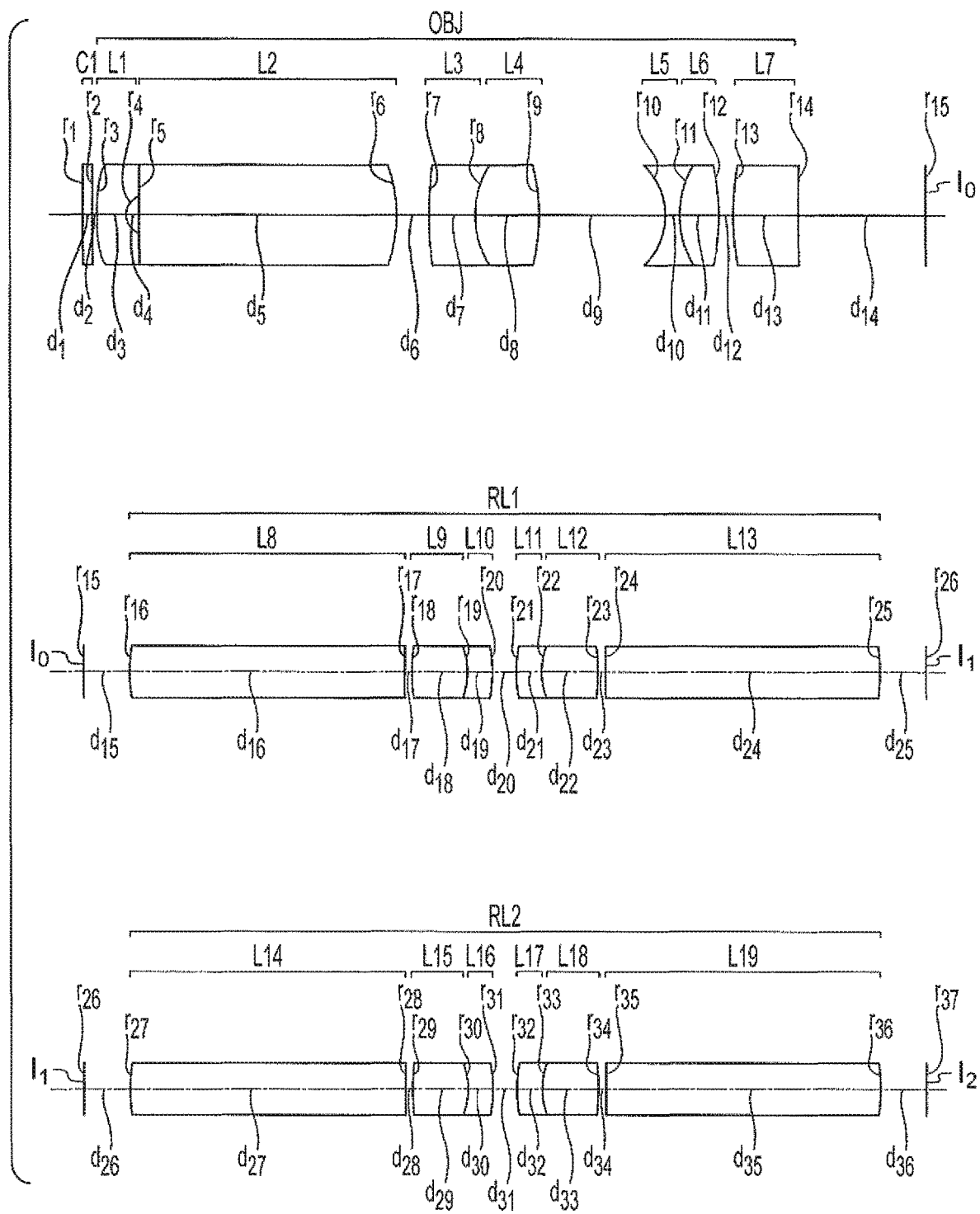
FIG. 12 is a lens cross-sectional view of an optical system for endoscope according to an example 5.
Figure 13:
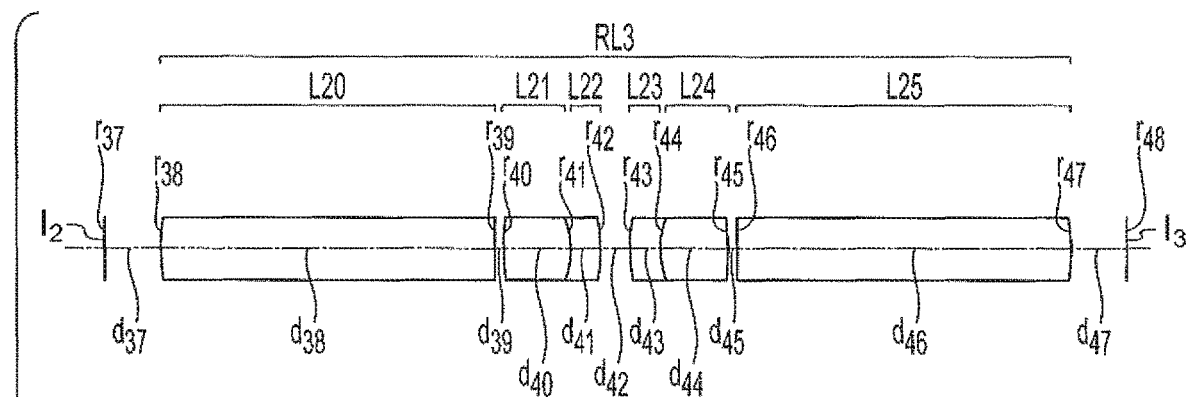
FIG. 13 is a lens cross-sectional view of the optical system for endoscope according to the example 5.
Figure 13:
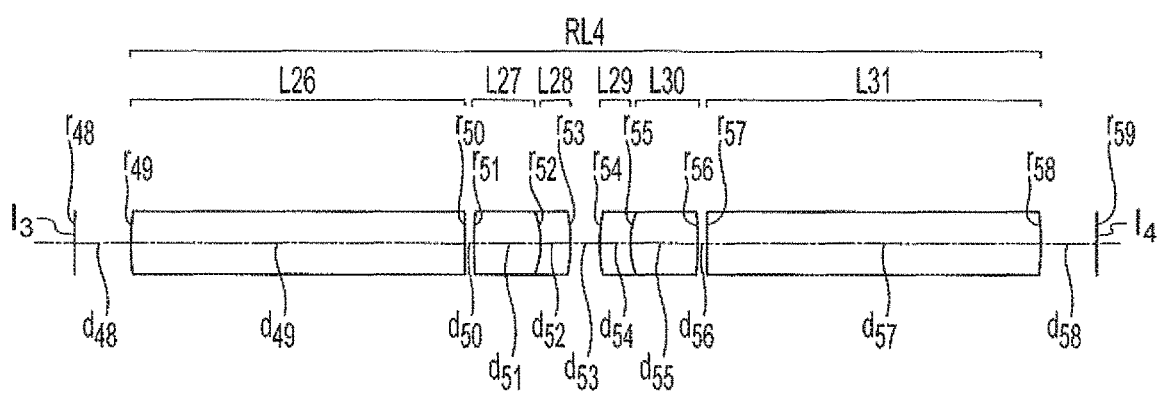
Figure 13:
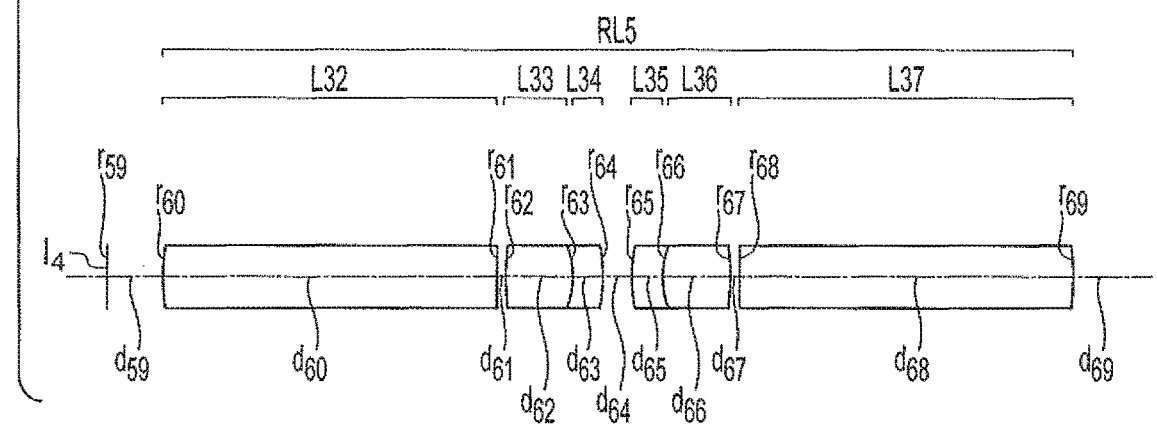
Figure 14:
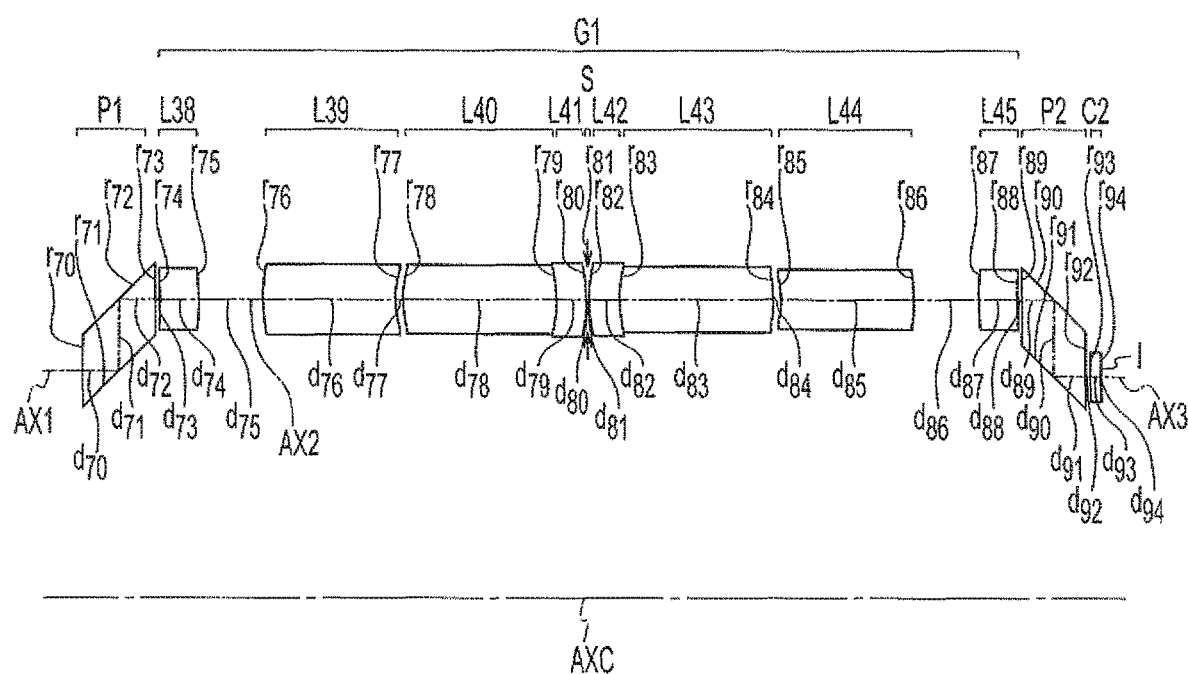
FIG. 14 is a lens cross-sectional view of the optical system for endoscope according to the example 5.

Lens cross-sectional views of a stereoscopic-vision endoscope optical system of an example 5 are shown in FIG. 12, FIG. 13, and FIG. 14. In FIG. 12, an objective optical system OBJ, a first relay optical system RL1, and a second relay optical system RL2 are shown. In FIG. 13, a third relay optical system RL3, a fourth relay optical system RL4, and a fifth relay optical system RL5 are shown. In FIG. 14, an image forming optical system is shown.

The stereoscopic-vision endoscope optical system of the example 5 includes in order from an object side, the objective optical system OBJ, the first relay optical system RL1, the second relay optical system RL2, the third relay optical system RL3, the fourth relay optical system RL4, the fifth relay optical system RL5, and the image forming optical system.

A primary image Io is formed by the objective optical system OBJ. The primary image Io is relayed by the first relay optical system RL1. Accordingly, a first relay image I1 is formed. The first relay image I1 is relayed by the second relay optical system RL2. Accordingly, a second relay image I2 is formed. The second relay image I2 is relayed by the third relay optical system RL3. Accordingly, a third relay image I3 is formed. The third relay image I3 is relayed by the fourth relay optical system RL4. Accordingly, a fourth relay image I4 is formed.

The fourth relay image I4 is relayed by the fifth relay optical system RL5. Accordingly, a fifth relay image is formed, which is not shown in the lens cross-sectional views of the example 5. The fifth relay image is an intermediate image. A final image I is formed by the image forming optical system.

The objective optical system OBJ includes in order from the object side, a planoconcave negative lens L1, a planoconvex positive lens L2, a negative meniscus lens L3 having a convex surface directed toward an object side, a biconvex positive lens L4, a biconcave negative lens L5, a biconvex positive lens L6, and a positive meniscus lens L7 having a convex surface directed toward the object side. Here, the negative meniscus lens L3 and the biconvex positive lens L4 are cemented. The biconcave negative lens L5 and the biconvex positive lens L6 are cemented. A cover glass C1 is disposed on the object side of the planoconcave negative lens L1.

The first relay optical system RL1 includes a planoconvex positive lens L8, a biconvex positive lens L9, a negative meniscus lens L10 having a convex surface directed toward an image side, a negative meniscus lens L11 having a convex surface directed toward the object side, the biconvex positive lens L12, and a planoconvex positive lens L13. Here, the biconvex positive lens L9 and the negative meniscus lens L10 are cemented. The negative meniscus lens L11 and the biconvex positive lens L12 are cemented.

The second relay optical system RL2 includes a planoconvex positive lens L14, a biconvex positive lens L15, a negative meniscus lens L16 having a convex surface directed toward the image side, a negative meniscus lens L17 having a convex surface directed toward the object side, a biconvex positive lens L18, and a planoconvex positive lens L19. Here, the biconvex positive lens L15 and the negative meniscus lens L16 are cemented. The negative meniscus lens L17 and the biconvex positive lens L18 are cemented.

The third relay optical system RL3 includes a planoconvex positive lens L20, a biconvex positive lens L21, a negative meniscus lens L22 having a convex surface directed toward the image side, a negative meniscus lens L23 having a convex surface directed toward the object side, a biconvex positive lens L24, and a planoconvex positive lens L25. Here, the biconvex positive lens L21 and the negative meniscus lens L22 are cemented. The negative meniscus lens L23 and the biconvex positive lens L24 are cemented.

The fourth relay optical system RL4 includes a planoconvex positive lens L26, a biconvex positive lens L27, a negative meniscus lens L28 having a convex surface directed toward the image side, a negative meniscus lens L29 having a convex surface directed toward the object side, a biconvex positive lens L30, and a planoconvex positive lens L31. Here, the biconvex positive lens L27 and the negative meniscus lens L28 are cemented. The negative meniscus lens L29 and the biconvex positive lens L30 are cemented.

The fifth relay optical system RL5 includes a planoconvex positive lens L32, a biconvex positive lens L33, a negative meniscus lens L34 having a convex surface directed toward the image side, a negative meniscus lens L35 having a convex surface directed toward the object side, a biconvex positive lens L36, and a planoconvex positive lens L37. Here, the biconvex positive lens L33 and the negative meniscus lens L34 are cemented. The negative meniscus lens L35 and the biconvex positive lens L36 are cemented.

The image forming optical system includes in order from the object side, a prism P1, a first lens unit G1, and a prism P2.

The first lens unit G1 includes a positive meniscus lens L38 having a convex surface directed toward the image side, a negative meniscus lens L39 having a convex surface directed toward the object side, a biconvex positive lens L40, a negative meniscus lens L41 having a convex surface directed toward the image side, a negative meniscus lens L42 having a convex surface directed toward the object side, a biconvex positive lens L43, a negative meniscus lens L44 having a convex surface directed toward the image side, and a positive meniscus lens L45 having a convex surface directed toward the object side. The positive meniscus lens L45 is to be moved for focusing.

Here, the biconvex positive lens L40 and the negative meniscus lens L41 are cemented. The negative meniscus lens L42 and the biconvex positive lens L43 are cemented.

An aperture stop S is disposed between the negative meniscus lens L41 and the negative meniscus lens L42.

The prism P1 is the first optical-path bending element. The prism P1 has a first reflecting surface r71 and a second reflecting surface r72. The prism P2 is the second optical-path bending element. The prism P2 has a third reflecting surface r90 and a fourth reflecting surface r91.

A cover glass C2 is disposed between the first lens unit G1 and the final image I.

An aspheric surface is provided to both surfaces of the planoconcave negative lens L1.

A second optical axis AX2 is positioned farther from a central axis AXc, than a first optical axis AX1. A third optical axis AX3 is positioned closer to the central axis AXc, than the second optical axis AX2.

Figure 15:
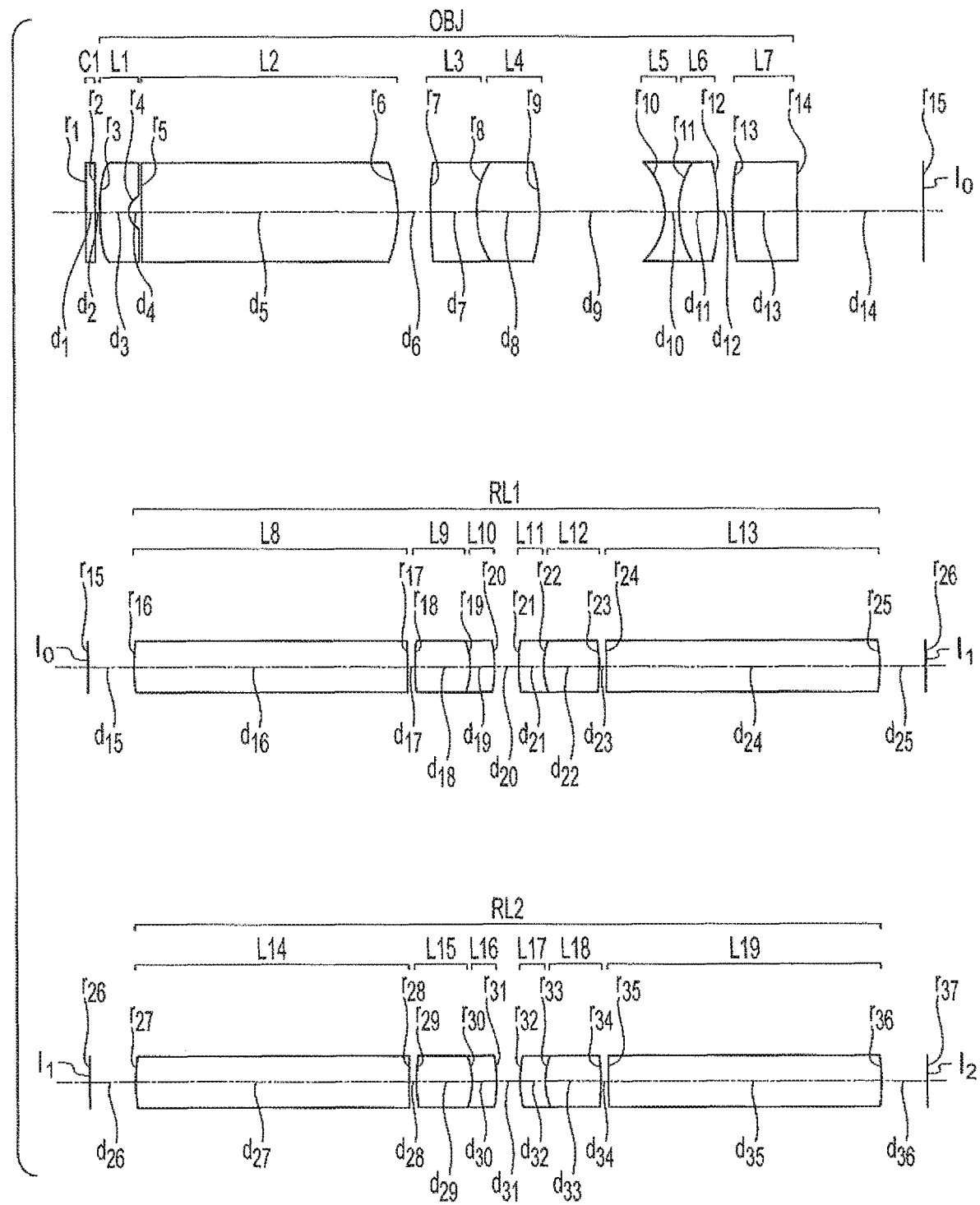
FIG. 15 is a lens cross-sectional view of an optical system for endoscope according to an example 6.
Figure 16:
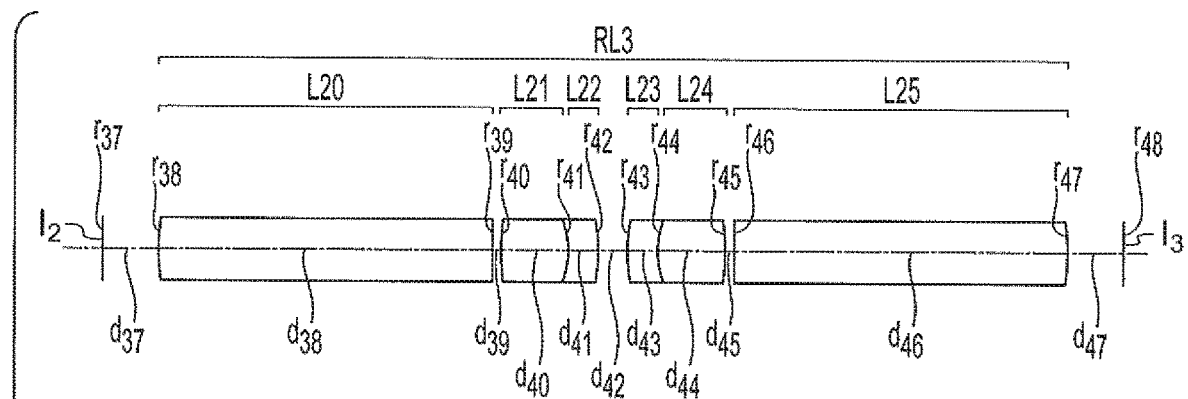
FIG. 16 is a lens cross-sectional view of the optical system for endoscope according to the example 6.
Figure 16:
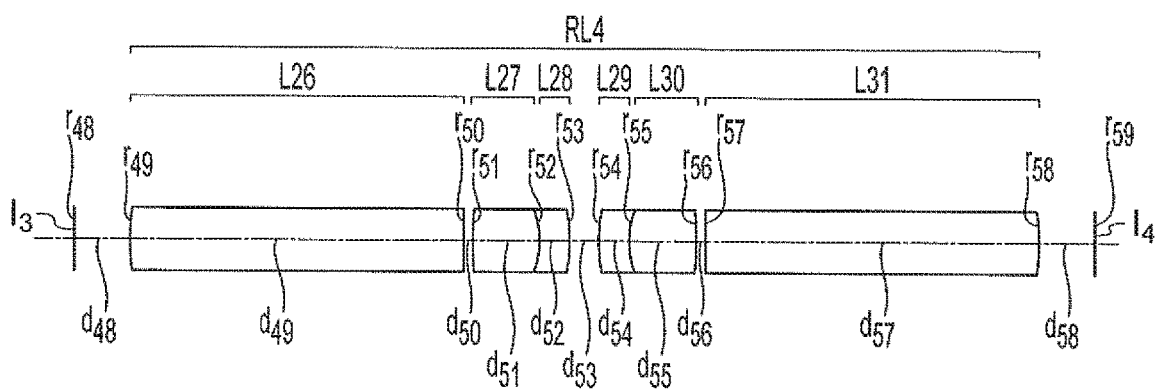
Figure 16:
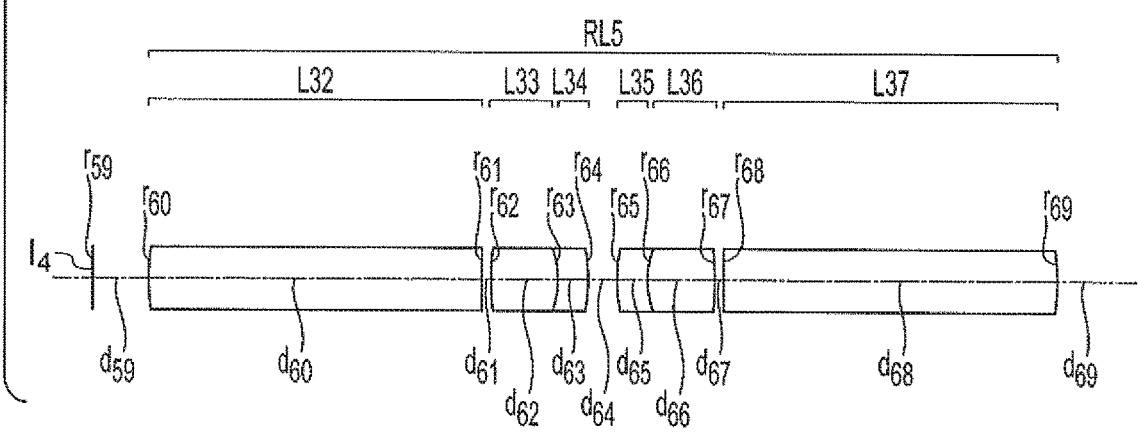
Figure 17:
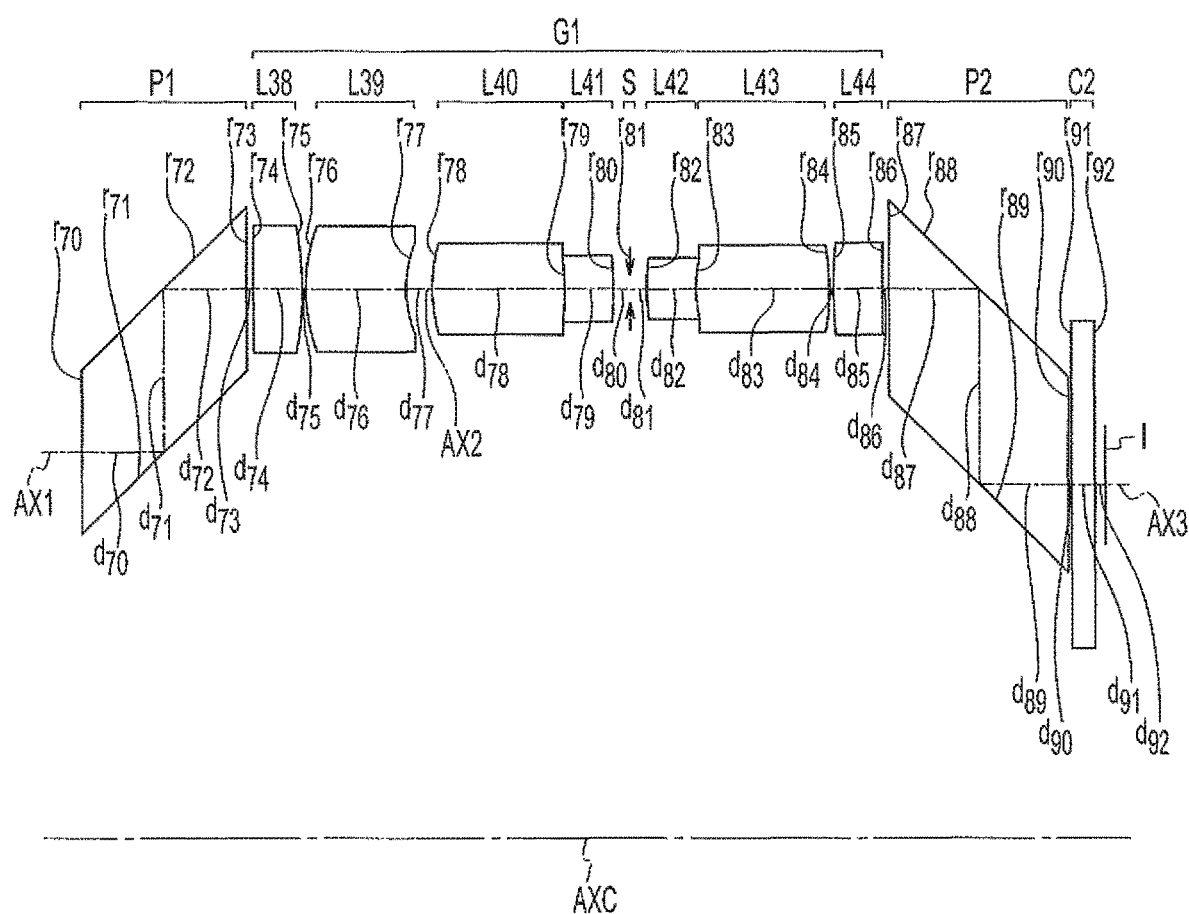
FIG. 17 is a lens cross-sectional view of the optical system for endoscope according to the example 6.
Figure 18A:
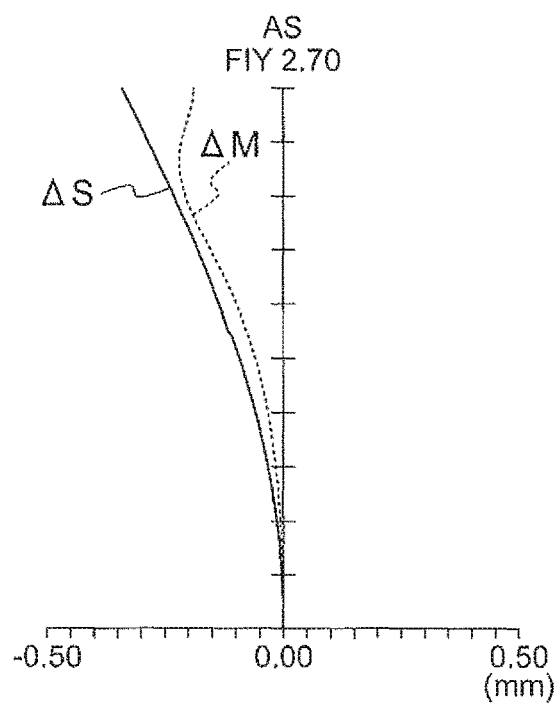
FIG. 18A, FIG. 18B, FIG. 18C, FIG. 18D, FIG. 18E, FIG. 18F, FIG. 18G, and FIG. 18H are aberration diagrams of the optical system for endoscope according to the example 1.
Figure 18B:
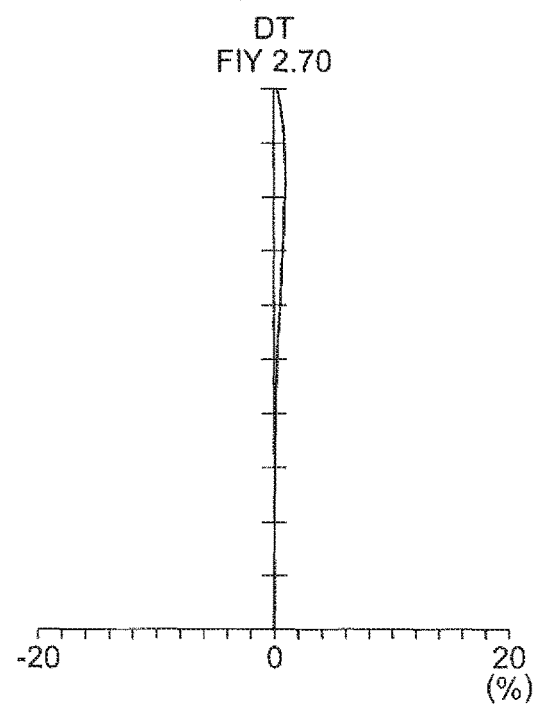
Figure 18C:
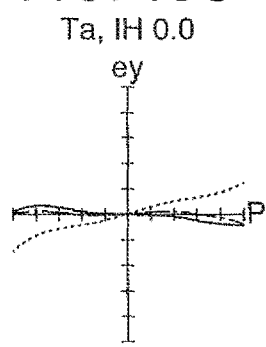
Figure 18D:
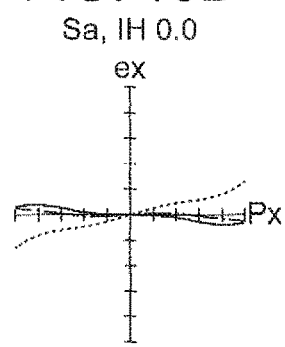
Figure 18E:
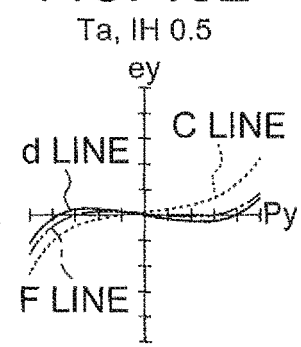
Figure 18F:
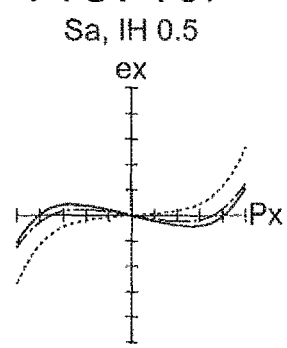
Figure 18G:
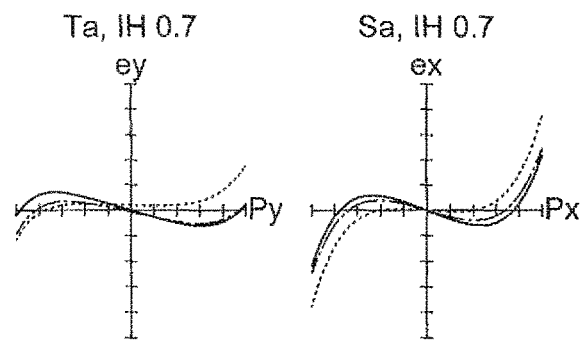
Figure 18H:
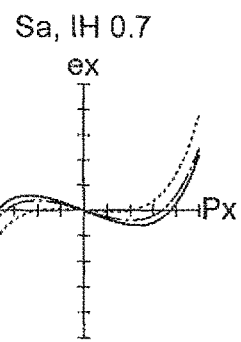
Figure 20A:
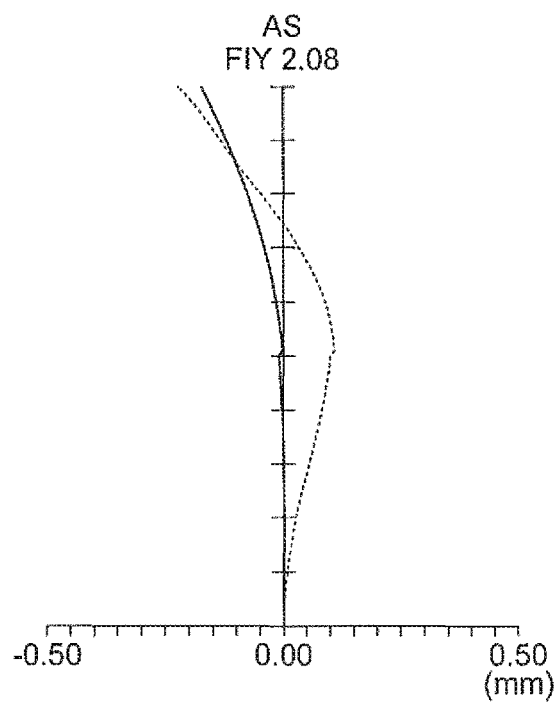
FIG. 20A, FIG. 20B, FIG. 20C, FIG. 20D, FIG. 20E, FIG. 20F, FIG. 20G, and FIG. 20H are aberration diagrams of the optical system for endoscope according to the example 3.
Figure 20B:
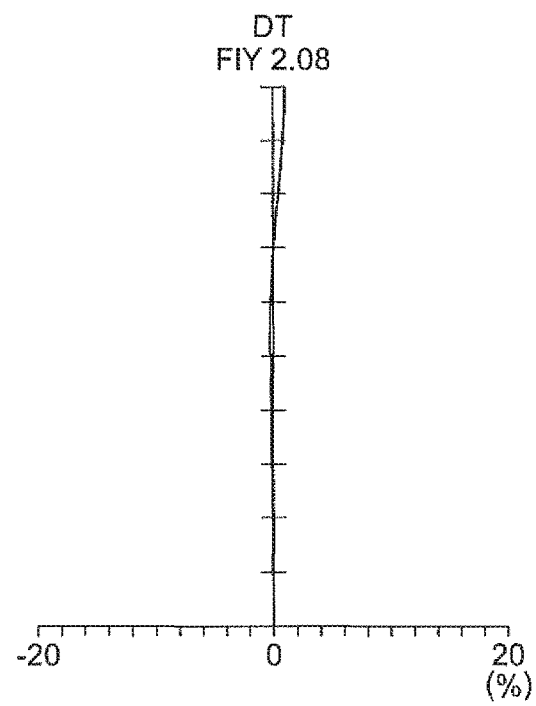
Figure 20C:
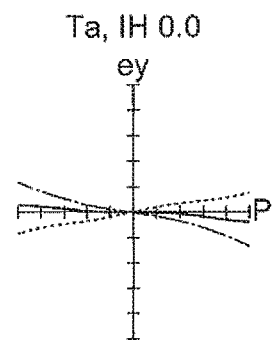
Figure 20D:
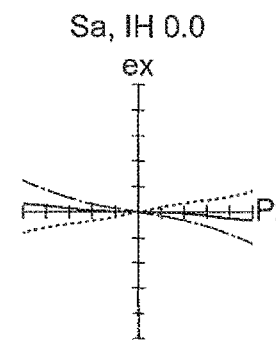
Figure 20E:
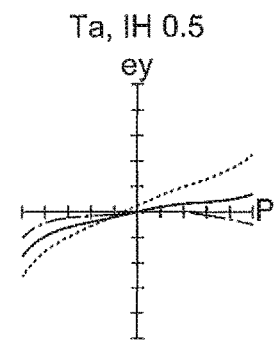
Figure 20F:
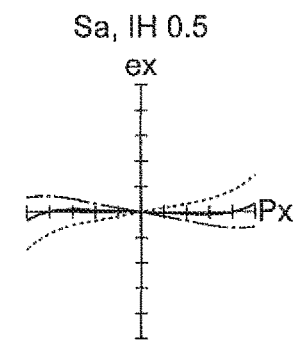
Figure 20G:
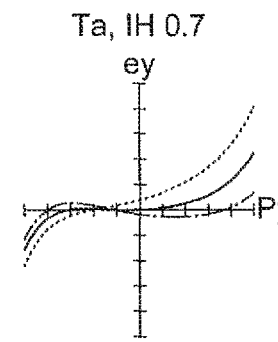
Figure 20H:
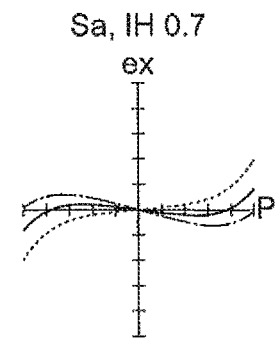
Figure 21A:
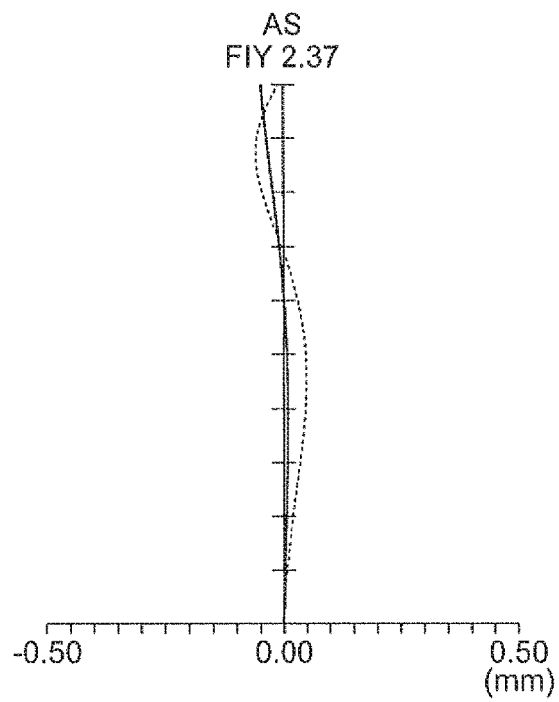
FIG. 21A, FIG. 21B, FIG. 21C, FIG. 21D, FIG. 21E, FIG. 21F, FIG. 21G, and FIG. 21H are aberration diagrams of the optical system for endoscope according to the example 4.
Figure 21B:
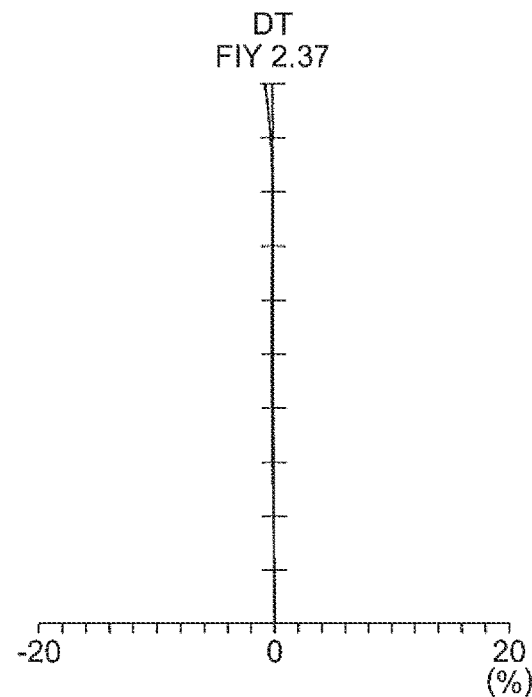
Figure 21C:
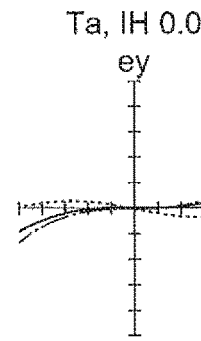
Figure 21D:
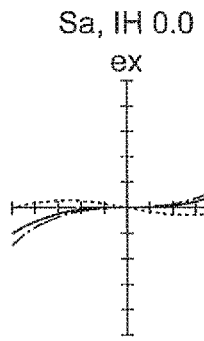
Figure 21E:
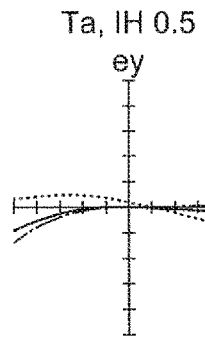
Figure 21F:
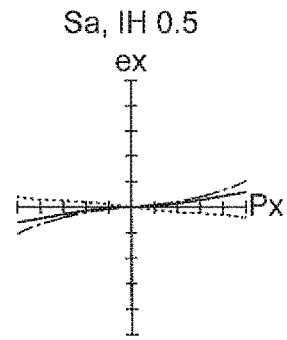
Figure 21G:
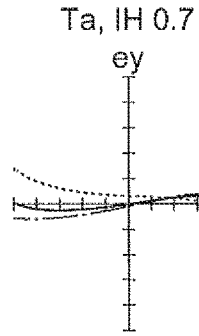
Figure 21H:
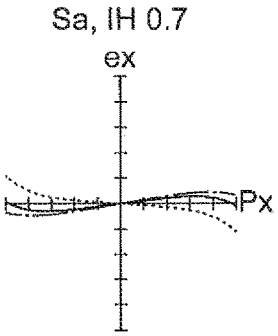
Figure 22A:
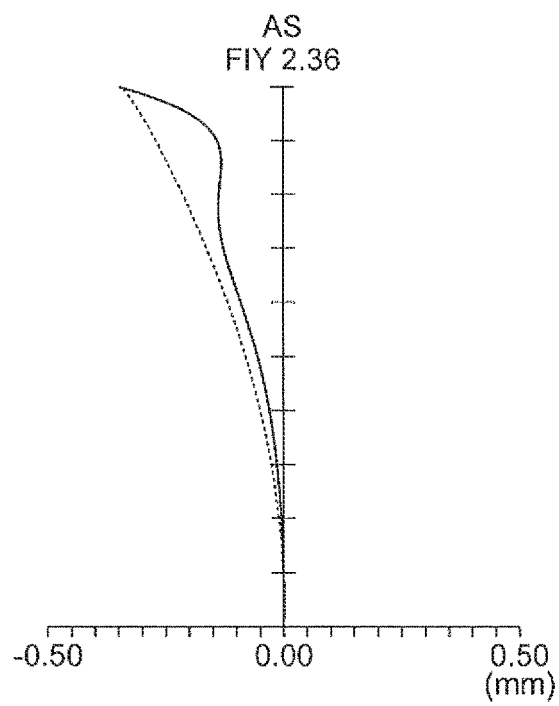
FIG. 22A, FIG. 22B, FIG. 22C, FIG. 22D, FIG. 22E, FIG. 22F, FIG. 22G, and FIG. 22H are aberration diagrams of the optical system for endoscope according to the example 5.
Figure 22B:
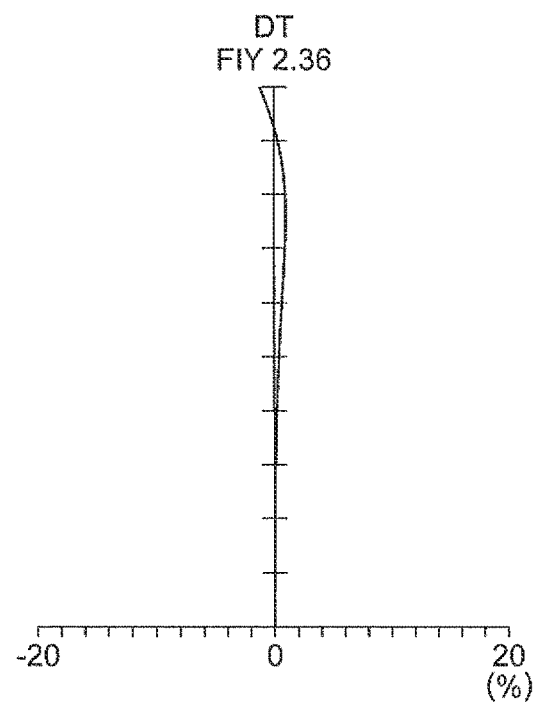
Figure 22C:
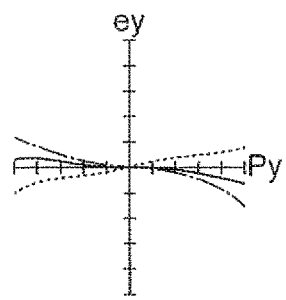
Figure 22D:
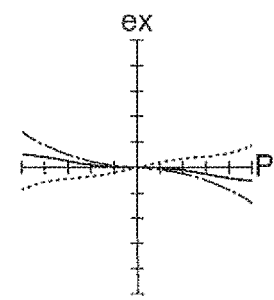
Figure 22E:
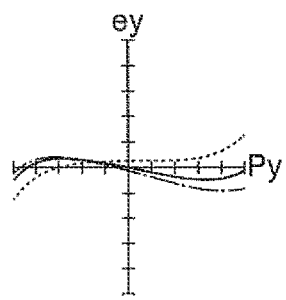
Figure 22F:
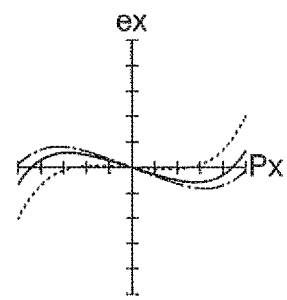
Figure 22G:
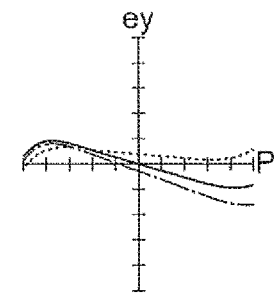
Figure 22H:
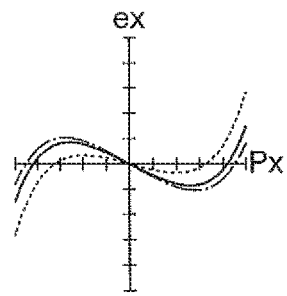
Figure 23A:
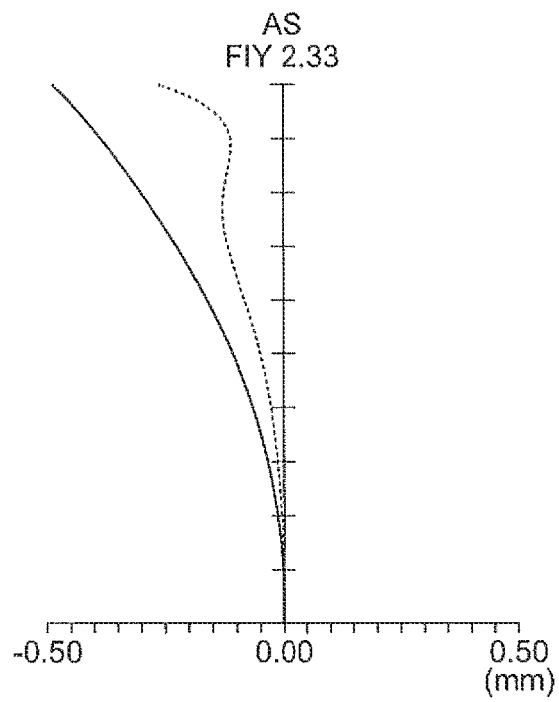
FIG. 23A, FIG. 23B, FIG. 23C, FIG. 23D, FIG. 23E, FIG. 23F, FIG. 23G, and FIG. 23H are aberration diagrams of the optical system for endoscope according to the example 6.
Figure 23B:
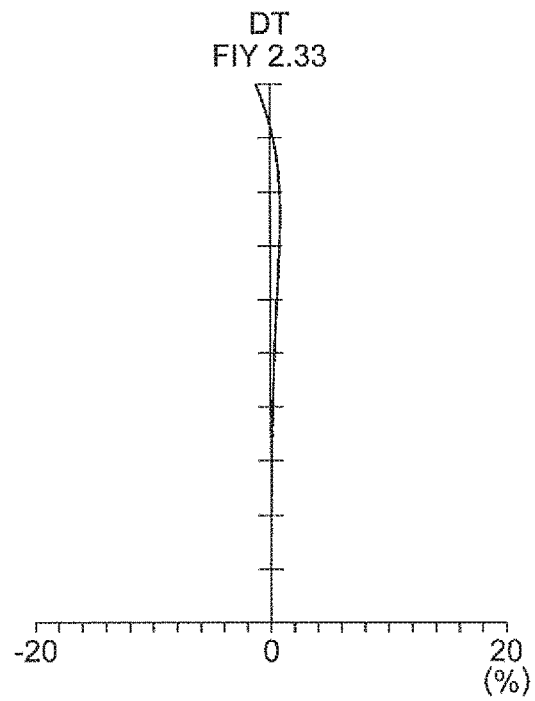
Figure 23C:
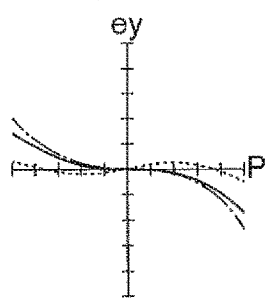
Figure 23D:
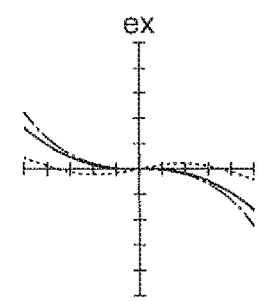
Figure 23E:
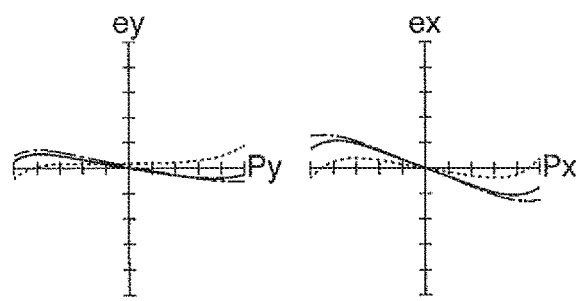
Figure 23F:
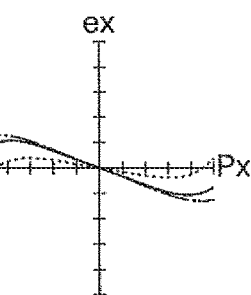
Figure 23G:
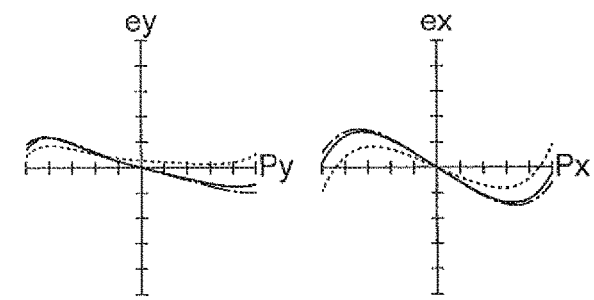
Figure 23H:
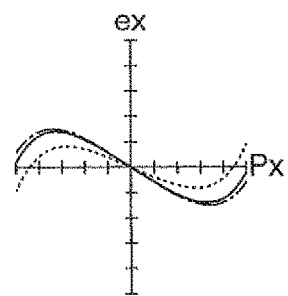

Lens cross-sectional views of a stereoscopic-vision endoscope optical system of an example 6 are shown in FIG. 15, FIG. 16, and FIG. 17. In FIG. 15, an objective optical system OBJ, a first relay optical system RL1, and a second relay optical system RL2 are shown. In FIG. 16, a third relay optical system RL3, a fourth relay optical system RL4, and a fifth relay optical system RL5 are shown. In FIG. 17, an image forming optical system is shown.

The stereoscopic-vision endoscope optical system of the example 6 includes in order from an object side, the objective optical system OBJ, the first relay optical system RL1, the second relay optical system RL2, the third relay optical system RL3, the fourth relay optical system RL4, the fifth relay optical system RL5, and the image forming optical system.

A primary image Io is formed by the objective optical system OBJ. The primary image Io is relayed by the first relay optical system RL1. Accordingly, a first relay image I1 is formed. The first relay image I1 is relayed by the second relay optical system RL2. Accordingly, a second relay image I2 is formed. The second relay image I2 is relayed by the third relay optical system RL3. Accordingly, a third relay image I3 is formed. The third relay image I3 is relayed by the fourth relay optical system RL4. Accordingly, a fourth relay image I4 is formed.

The fourth relay image I4 is relayed by the fifth relay optical system RL5. Accordingly, a fifth relay image is formed, which is not shown in the lens cross-sectional views of the example 6. The fifth relay image is an intermediate image. A final image I is formed by the image forming optical system.

The objective optical system OBJ includes in order from the object side, a planoconcave negative lens L1, a planoconvex positive lens L2, a negative meniscus lens L3 having a convex surface directed toward an object side, a biconvex positive lens L4, a biconcave negative lens L5, a biconvex positive lens L6, and a positive meniscus lens L7 having a convex surface directed toward the object side. Here, the negative meniscus lens L3 and the biconvex positive lens L4 are cemented. The biconcave negative lens L5 and the biconvex positive lens L6 are cemented. A cover glass C1 is disposed on the object side of the planoconcave negative lens L1.

The first relay optical system RL1 includes a planoconvex positive lens L8, a biconvex positive lens L9, a negative meniscus lens L10 having a convex surface directed toward an image side, a negative meniscus lens L11 having a convex surface directed toward the object side, a biconvex positive lens L12, and a planoconvex positive lens L13. Here, the biconvex positive lens L9 and the negative meniscus lens L10 are cemented. The negative meniscus lens L11 and the biconvex positive lens L12 are cemented.

The second relay optical system RL2 includes a planoconvex positive lens L14, a biconvex positive lens L15, a negative meniscus lens L16 having a convex surface directed toward the image side, a negative meniscus lens L17 having a convex surface directed toward the object side, a biconvex positive lens L18, and a planoconvex positive lens L19. Here, the biconvex positive lens L15 and the negative meniscus lens L16 are cemented. The negative meniscus lens L17 and the biconvex positive lens L18 are cemented.

The third relay optical system RL3 includes a planoconvex positive lens L20, a biconvex positive lens L21, a negative meniscus lens L22 having a convex surface directed toward the image side, a negative meniscus lens L23 having a convex surface directed toward the object side, a biconvex positive lens L24, and a planoconvex positive lens L25. Here, the biconvex positive lens L21 and the negative meniscus lens L22 are cemented. The negative meniscus lens L23 and the biconvex positive lens L24 are cemented.

The fourth relay optical system RL4 includes a planoconvex positive lens L26, a biconvex positive lens L27, a negative meniscus lens L28 having a convex surface directed toward the image side, a negative meniscus lens L29 having a convex surface directed toward the object side, a biconvex positive lens L30, and a planoconvex positive lens L31. Here, the biconvex positive lens L27 and the negative meniscus lens L28 are cemented. The negative meniscus lens L29 and the biconvex positive lens L30 are cemented.

The fifth relay optical system RL5 includes a planoconvex positive lens L32, a biconvex positive lens L33, a negative meniscus lens L34 having a convex surface directed toward the image side, a negative meniscus lens L35 having a convex surface directed toward the object side, a biconvex positive lens L36, and a planoconvex positive lens L37. Here, the biconvex positive lens L33 and the negative meniscus lens L34 are cemented. The negative meniscus lens L35 and the biconvex positive lens L36 are cemented.

The image forming optical system includes in order from the object side, a prism P1, a first lens unit G1, and a prism P2.

The first lens unit G1 includes a biconvex positive lens L38, a negative meniscus lens L39 having a convex surface directed toward the object side, a biconvex positive lens L40, a negative meniscus lens L41 having a convex surface directed toward the image side, a negative meniscus lens L42 having a convex surface directed toward the object side, a biconvex positive lens L43, and a positive meniscus lens L44 having a convex surface directed toward the object side. The positive meniscus lens L44 is to be moved for focusing.

Here, the biconvex positive lens L40 and the negative meniscus lens L41 are cemented. The negative meniscus lens L42 and the biconvex positive lens L43 are cemented.

An aperture stop S is disposed between the negative meniscus lens L41 and the negative meniscus lens L42.

The prism P1 is the first optical-path bending element. The prism P1 has a first reflecting surface r71 and a second reflecting surface r72. The prism P2 is the second optical-path bending element. The prism P2 has a third reflecting surface r88 and a fourth reflecting surface r89.

A cover glass C2 is disposed between the first lens unit G1 and the final image I.

An aspheric surface is provided to both surfaces of the planoconcave negative lens L1.

A second optical axis AX2 is positioned farther from a central axis AXc, than a first optical axis AX1. A third optical axis AX3 is positioned closer to the central axis AXc, than the second optical axis AX2.

Numerical data of each example described above is shown below. In Surface data, r denotes radius of curvature of each lens surface, d denotes a distance between respective lens surfaces, nd denotes a refractive index of each lens for a d-line, νd denotes an Abbe number for each lens, and * denotes an aspherical surface.

In various numerical data, f denotes a focal length of the stereoscopic-vision endoscope optical system, IH denotes the maximum image height, and FNO denotes an F-number.

A shape of an aspherical surface is defined by the following expression where the direction of the optical axis is represented by z, the direction orthogonal to the optical axis is represented by y, a conical coefficient is represented by K, aspherical surface coefficients are represented by A4, A6, A8, A10, A12 . . .

$$Z=(y^2/r)/[1+\{1-(1+k)(y/r)^2\}^{1/2}]+A4y^4+A6y^6+A8y^8+A10y^{10}+A12y^{12}+ \ldots$$

Further, in the aspherical surface coefficients, 'E-n' (where, n is an integral number) indicates '$10^{-n}$'. Moreover, these symbols are commonly used in the following numerical data for each example.

Moreover, in decentering data, a decentering amount is denoted by X, Y, and Z, and an angle of inclination is denoted by α, β, and γ. Here, X denotes a decentering amount in an X-axis direction, Y denotes a decentering amount in a Y-axis direction, and Z denotes a decentering amount in a Z-axis direction. Moreover, α denotes an angle of inclination with respect to the X-axis, β denotes an angle of inclination with respect to the Y-axis, and γ denotes an angle of inclination with respect to the Z-axis.

For instance, in a numerical example 1, a value of β on a $73^{rd}$ surface in the first optical path is a negative value. This indicates that the $73^{rd}$ surface is in a state of a plane rotated in a counterclockwise direction from the Y-axis.

Example 1

| Unit mm | | | | |
|---|---|---|---|---|
| Surface data | | | | |
| Surface no. | r | d | nd | νd |
| 1 | ∞ | 0.54 | 1.769 | 64.15 |
| 2 | ∞ | 0.27 | | |
| 3* | ∞ | 1.63 | 1.80625 | 40.91 |
| 4* | 1.022 | 0.72 | | |

-continued

Unit mm

| | | | | |
|---|---|---|---|---|
| 5 | ∞ | 14.5 | 1.883 | 40.76 |
| 6 | −8.28 | 1.83 | | |
| 7 | 26.096 | 2.62 | 1.72047 | 34.71 |
| 8 | 5.403 | 3.63 | 1.618 | 63.33 |
| 9 | −10.919 | 7.06 | | |
| 10 | −3.981 | 0.8 | 1.71736 | 29.52 |
| 11 | 5.778 | 2.24 | 1.883 | 40.77 |
| 12 | −11.851 | 0.8 | | |
| 13 | 17.8 | 3.64 | 1.7725 | 49.6 |
| 14 | 195.508 | 7.2 | | |
| 15 | ∞ | 5.03 | | |
| 16 | 19.696 | 29.78 | 1.7725 | 49.6 |
| 17 | ∞ | 0.81 | | |
| 18 | 25.555 | 6.02 | 1.497 | 81.55 |
| 19 | −8.033 | 2.75 | 1.7725 | 49.6 |
| 20 | −15.28 | 2.62 | | |
| 21 | 15.28 | 2.75 | 1.7725 | 49.6 |
| 22 | 8.033 | 6.02 | 1.497 | 81.55 |
| 23 | −25.555 | 0.81 | | |
| 24 | ∞ | 29.78 | 1.7725 | 49.6 |
| 25 | −19.696 | 5.03 | | |
| 26 | ∞ | 5.03 | | |
| 27 | 19.696 | 29.78 | 1.7725 | 49.6 |
| 28 | ∞ | 0.81 | | |
| 29 | 25.555 | 6.02 | 1.497 | 81.55 |
| 30 | −8.033 | 2.75 | 1.7725 | 49.6 |
| 31 | −15.28 | 2.62 | | |
| 32 | 15.28 | 2.75 | 1.7725 | 49.6 |
| 33 | 8.033 | 6.02 | 1.497 | 81.55 |
| 34 | −25.555 | 0.81 | | |
| 35 | ∞ | 29.78 | 1.7725 | 49.6 |
| 36 | −19.696 | 5.03 | | |
| 37 | ∞ | 5.03 | | |
| 38 | 19.696 | 29.78 | 1.7725 | 49.6 |
| 39 | ∞ | 0.81 | | |
| 40 | 25.555 | 6.02 | 1.497 | 81.55 |
| 41 | −8.033 | 2.75 | 1.7725 | 49.6 |
| 42 | −15.28 | 2.62 | | |
| 43 | 15.28 | 2.75 | 1.7725 | 49.6 |
| 44 | 8.033 | 6.02 | 1.497 | 81.55 |
| 45 | −25.555 | 0.81 | | |
| 46 | ∞ | 29.78 | 1.7725 | 49.6 |
| 47 | −19.696 | 5.03 | | |
| 48 | ∞ | 5.03 | | |
| 49 | 19.696 | 29.78 | 1.7725 | 49.6 |
| 50 | ∞ | 0.81 | | |
| 51 | 25.555 | 6.02 | 1.497 | 81.55 |
| 52 | −8.033 | 2.75 | 1.7725 | 49.6 |
| 53 | −15.28 | 2.62 | | |
| 54 | 15.28 | 2.75 | 1.7725 | 49.6 |
| 55 | 8.033 | 6.02 | 1.497 | 81.55 |
| 56 | −25.555 | 0.81 | | |
| 57 | ∞ | 29.78 | 1.7725 | 49.6 |
| 58 | −19.696 | 5.03 | | |
| 59 | ∞ | 5.03 | | |
| 60 | 19.696 | 29.78 | 1.7725 | 49.6 |
| 61 | ∞ | 0.81 | | |
| 62 | 25.555 | 6.02 | 1.497 | 81.55 |
| 63 | −8.033 | 2.75 | 1.7725 | 49.6 |
| 64 | −15.28 | 1.31 | | |
| 65 (Stop) | ∞ | 1.31 | | |
| 66 | 15.28 | 2.75 | 1.7725 | 49.6 |
| 67 | 8.033 | 6.02 | 1.497 | 81.55 |
| 68 | −25.555 | 0.81 | | |
| 69 | ∞ | 29.78 | 1.7725 | 49.6 |
| 70 | −19.696 | 0.95 | | |
| 71 | ∞ | 3.4 | 1.8061 | 40.93 |
| 72 | ∞ | 7.9 | 1.8061 | 40.93 |
| 73 | ∞ | 3.4 | 1.8061 | 40.93 |
| 74 | ∞ | 0.22 | | |
| 75 | 708.111 | 5.44 | 1.883 | 40.77 |
| 76 | −15.662 | 4.87 | | |
| 77 | −8.283 | 1.52 | 2.0033 | 28.27 |
| 78 | 33.398 | 10.04 | 1.804 | 46.58 |
| 79 | −13.096 | 0.23 | | |
| 80 | 2041.51 | 4.03 | 1.497 | 81.55 |
| 81 | −34.812 | 7.34 | | |
| 82 | ∞ | 4.08 | 1.76819 | 71.7 |
| 83 | ∞ | 4.08 | | |
| 84 | ∞ | 0.95 | 1.7682 | 71.7 |
| 85 | ∞ | 0.14 | | |
| 86 | ∞ | 4.08 | 1.8061 | 40.93 |
| 87 | ∞ | 7.26 | 1.8061 | 40.93 |
| 88 | ∞ | 4.08 | 1.8061 | 40.93 |
| 89 | ∞ | 0.39 | | |
| 90 | 16.318 | 4.08 | 1.497 | 81.55 |
| 91 | −147.835 | 0.41 | | |
| 92 | 10.228 | 4.19 | 1.497 | 81.55 |
| 93 | 12.274 | 3.16 | | |
| 94 | −47.057 | 0.95 | 1.69895 | 30.13 |
| 95 | 8.537 | 3.78 | | |
| 96 | 19.153 | 8.16 | 1.83481 | 42.71 |
| 97 | −46.376 | 20.77 | | |
| 98 | ∞ | 1.07 | 1.52113 | 66.54 |
| 99 | ∞ | 0.68 | | |
| 100 | ∞ | 0.53 | 1.51633 | 64.14 |
| 101 | ∞ | 1.09 | | |
| Image plane | ∞ | | | |

Aspherical surface data

3rd surface k = 0
A4 = 2.196.E−02, A6 = −4.5356.E−03, A8 = 3.4501.E−04

4th surface k = −0.2024
A4 = 9.164.E−03, A6 = 2.1354.E−02, A8 = −9.6887.E−02

Various data

| | |
|---|---|
| IH | 2.70 |
| f | 4.00 |
| FNO. | 6.1 |

Eccentricity data

71st surface

| X | Y | Z |
|---|---|---|
| 0.00 | −0.15 | 0.00 |
| α | β | γ |
| 0.0 | 0.0 | 0.0 |

72nd surface

| X | Y | Z |
|---|---|---|
| 0.00 | 0.00 | 0.00 |
| α | β | γ |
| 45.0 | 0.0 | 0.0 |

73rd surface

| X | Y | Z |
|---|---|---|
| 0.00 | 0.00 | 0.00 |
| α | β | γ |
| −45.0 | 0.0 | 0.0 |

87th surface

| X | Y | Z |
|---|---|---|
| 0.00 | 0.00 | 0.00 |

-continued

Unit mm

| α | β | γ |
|---|---|---|
| −45.0 | 0.0 | 0.0 |

88th surface

| X | Y | Z |
|---|---|---|
| 0.00 | 0.00 | 0.00 |

| α | β | γ |
|---|---|---|
| 45.0 | 0.0 | 0.0 |

Example 2

Unit mm

Surface data

| Surface no. | r | d | nd | νd |
|---|---|---|---|---|
| 1 | ∞ | 0.51 | 1.769 | 64.15 |
| 2 | ∞ | 0.26 | | |
| 3 | ∞ | 1.53 | 1.8061 | 40.88 |
| 4* | 0.959 | 0.68 | | |
| 5 | ∞ | 13.61 | 1.883 | 40.77 |
| 6 | −7.776 | 1.72 | | |
| 7 | 24.508 | 2.46 | 1.72047 | 34.71 |
| 8 | 5.074 | 3.41 | 1.618 | 63.33 |
| 9 | −10.255 | 6.63 | | |
| 10 | −3.739 | 0.75 | 1.71736 | 29.52 |
| 11 | 5.426 | 2.1 | 1.883 | 40.77 |
| 12 | −11.13 | 0.75 | | |
| 13 | 16.717 | 3.42 | 1.7725 | 49.6 |
| 14 | 183.612 | 6.76 | | |
| 15 | ∞ | 4.73 | | |
| 16 | 18.498 | 27.97 | 1.7725 | 49.6 |
| 17 | ∞ | 0.76 | | |
| 18 | 24 | 5.66 | 1.497 | 81.55 |
| 19 | −7.545 | 2.58 | 1.7725 | 49.6 |
| 20 | −14.35 | 2.46 | | |
| 21 | 14.35 | 2.58 | 1.7725 | 49.6 |
| 22 | 7.545 | 5.66 | 1.497 | 81.55 |
| 23 | −24 | 0.76 | | |
| 24 | ∞ | 27.97 | 1.7725 | 49.6 |
| 25 | −18.498 | 4.73 | | |
| 26 | ∞ | 4.73 | | |
| 27 | 18.498 | 27.97 | 1.7725 | 49.6 |
| 28 | ∞ | 0.76 | | |
| 29 | 24 | 5.66 | 1.497 | 81.55 |
| 30 | −7.545 | 2.58 | 1.7725 | 49.6 |
| 31 | −14.35 | 2.46 | | |
| 32 | 14.35 | 2.58 | 1.7725 | 49.6 |
| 33 | 7.545 | 5.66 | 1.497 | 81.55 |
| 34 | −24 | 0.76 | | |
| 35 | ∞ | 27.97 | 1.7725 | 49.6 |
| 36 | −18.498 | 4.73 | | |
| 37 | ∞ | 4.73 | | |
| 38 | 18.498 | 27.97 | 1.7725 | 49.6 |
| 39 | ∞ | 0.76 | | |
| 40 | 24 | 5.66 | 1.497 | 81.55 |
| 41 | −7.545 | 2.58 | 1.7725 | 49.6 |
| 42 | −14.35 | 2.46 | | |
| 43 | 14.35 | 2.58 | 1.7725 | 49.6 |
| 44 | 7.545 | 5.66 | 1.497 | 81.55 |
| 45 | −24 | 0.76 | | |
| 46 | ∞ | 27.97 | 1.7725 | 49.6 |
| 47 | −18.498 | 4.73 | | |
| 48 | ∞ | 4.73 | | |
| 49 | 18.498 | 27.97 | 1.7725 | 49.6 |
| 50 | ∞ | 0.76 | | |
| 51 | 24 | 5.66 | 1.497 | 81.55 |
| 52 | −7.545 | 2.58 | 1.7725 | 49.6 |
| 53 | −14.35 | 2.46 | | |
| 54 | 14.35 | 2.58 | 1.7725 | 49.6 |
| 55 | 7.545 | 5.66 | 1.497 | 81.55 |
| 56 | −24 | 0.76 | | |
| 57 | ∞ | 27.97 | 1.7725 | 49.6 |
| 58 | −18.498 | 4.73 | | |
| 59 | ∞ | 4.73 | | |
| 60 | 18.498 | 27.97 | 1.7725 | 49.6 |
| 61 | ∞ | 0.76 | | |
| 62 | 24 | 5.66 | 1.497 | 81.55 |
| 63 | −7.545 | 2.58 | 1.7725 | 49.6 |
| 64 | −14.35 | 1.23 | | |
| 65 (Stop) | ∞ | 1.23 | | |
| 66 | 14.35 | 2.58 | 1.7725 | 49.6 |
| 67 | 7.545 | 5.66 | 1.497 | 81.55 |
| 68 | −24 | 0.76 | | |
| 69 | ∞ | 27.97 | 1.7725 | 49.6 |
| 70 | −18.498 | 5.69 | | |
| 71 | ∞ | 2.4 | 1.8061 | 40.93 |
| 72 | ∞ | 5.75 | 1.8061 | 40.93 |
| 73 | ∞ | 2.4 | 1.8061 | 40.93 |
| 74 | ∞ | 0.43 | | |
| 75 | 28.801 | 2.47 | 1.883 | 40.77 |
| 76 | −20.886 | 2.26 | | |
| 77 | −6.857 | 0.89 | 2.0033 | 28.27 |
| 78 | 20.112 | 7.78 | 1.816 | 46.62 |
| 79 | −11.502 | 1.04 | | |
| 80 | ∞ | 3.1 | 1.618 | 63.33 |
| 81 | −20.637 | 4.5 | | |
| 82 | ∞ | 2.87 | 1.76819 | 71.7 |
| 83 | ∞ | 2.87 | | |
| 84 | ∞ | 0.67 | 1.7682 | 71.7 |
| 85 | ∞ | 0.1 | | |
| 86 | ∞ | 3.07 | 1.8061 | 40.93 |
| 87 | ∞ | 6.16 | 1.8061 | 40.93 |
| 88 | ∞ | 3.07 | 1.8061 | 40.93 |
| 89 | ∞ | 0.28 | | |
| 90 | 11.494 | 2.87 | 1.497 | 81.55 |
| 91 | −104.13 | 0.29 | | |
| 92 | 7.204 | 2.95 | 1.497 | 81.55 |
| 93 | 8.645 | 2.22 | | |
| 94 | −33.145 | 0.67 | 1.69895 | 30.13 |
| 95 | 6.013 | 2.66 | | |
| 96 | 13.491 | 5.75 | 1.83481 | 42.71 |
| 97 | −32.666 | 6.87 | | |
| 98 | ∞ | 0.96 | 1.52113 | 66.54 |
| 99 | ∞ | 0.48 | | |
| 100 | ∞ | 0.67 | 1.51633 | 64.14 |
| 101 | ∞ | 1.2 | | |
| Image plane | ∞ | | | |

Aspherical surface data

4th surface k = 0
A4 = 2.651.E−02, A6 = −6.2080.E−03, A8 = 5.3540.E−04
5th surface k = −0.2024
A4 = 1.106.E−02, A6 = 2.9227.E−02, A8 = −1.5035.E−01

Various data

| IH | 2.53 |
|---|---|
| f | 3.01 |
| FNO. | 4.7 |

Eccentricity data

71st surface

| X | Y | Z |
|---|---|---|
| 0.00 | −0.14 | 0.00 |

-continued

| Unit mm | | |
|---|---|---|
| α | β | γ |
| 0.0 | 0.0 | 0.0 |

72nd surface

| X | Y | Z |
|---|---|---|
| 0.00 | 0.00 | 0.00 |
| α | β | γ |
| 45.0 | 0.0 | 0.0 |

73rd surface

| X | Y | Z |
|---|---|---|
| 0.00 | 0.00 | 0.00 |
| α | β | γ |
| −45.0 | 0.0 | 0.0 |

87th surface

| X | Y | Z |
|---|---|---|
| 0.00 | 0.00 | 0.00 |
| α | β | γ |
| −45.0 | 0.0 | 0.0 |

88th surface

| X | Y | Z |
|---|---|---|
| 0.00 | 0.00 | 0.00 |
| α | β | γ |
| 45.0 | 0.0 | 0.0 |

Example 3

Unit mm

Surface data

| Surface no. | r | d | nd | vd |
|---|---|---|---|---|
| 1 | ∞ | 0.52 | 1.769 | 64.15 |
| 2 | ∞ | 0.26 | | |
| 3 | ∞ | 1.57 | 1.8061 | 40.93 |
| 4* | 0.985 | 0.7 | | |
| 5 | ∞ | 13.98 | 1.883 | 40.77 |
| 6 | −7.983 | 1.77 | | |
| 7 | 25.16 | 2.53 | 1.72047 | 34.7 |
| 8 | 5.209 | 3.5 | 1.618 | 63.33 |
| 9 | −10.527 | 6.81 | | |
| 10 | −3.838 | 0.77 | 1.71736 | 29.52 |
| 11 | 5.571 | 2.16 | 1.883 | 40.77 |
| 12 | −11.426 | 0.77 | | |
| 13 | 17.161 | 3.51 | 1.7725 | 49.6 |
| 14 | 188.495 | 6.94 | | |
| 15 | ∞ | 4.85 | | |
| 16 | 18.987 | 28.71 | 1.7725 | 49.6 |
| 17 | ∞ | 0.78 | | |
| 18 | 24.668 | 5.81 | 1.497 | 81.55 |
| 19 | −7.75 | 2.65 | 1.7725 | 49.6 |
| 20 | −14.732 | 2.52 | | |
| 21 | 14.732 | 2.65 | 1.7725 | 49.6 |
| 22 | 7.75 | 5.81 | 1.497 | 81.55 |
| 23 | −24.668 | 0.78 | | |
| 24 | ∞ | 28.71 | 1.7725 | 49.6 |
| 25 | −18.987 | 4.85 | | |
| 26 | ∞ | 4.85 | | |
| 27 | 18.987 | 28.71 | 1.7725 | 49.6 |
| 28 | ∞ | 0.78 | | |
| 29 | 24.668 | 5.81 | 1.497 | 81.55 |
| 30 | −7.75 | 2.65 | 1.7725 | 49.6 |
| 31 | −14.732 | 2.52 | | |
| 32 | 14.732 | 2.65 | 1.7725 | 49.6 |
| 33 | 7.75 | 5.81 | 1.497 | 81.55 |
| 34 | −24.668 | 0.78 | | |
| 35 | ∞ | 28.71 | 1.7725 | 49.6 |
| 36 | −18.987 | 4.85 | | |
| 37 | ∞ | 4.85 | | |
| 38 | 18.987 | 28.71 | 1.7725 | 49.6 |
| 39 | ∞ | 0.78 | | |
| 40 | 24.668 | 5.81 | 1.497 | 81.55 |
| 41 | −7.75 | 2.65 | 1.7725 | 49.6 |
| 42 | −14.732 | 2.52 | | |
| 43 | 14.732 | 2.65 | 1.7725 | 49.6 |
| 44 | 7.75 | 5.81 | 1.497 | 81.55 |
| 45 | −24.668 | 0.78 | | |
| 46 | ∞ | 28.71 | 1.7725 | 49.6 |
| 47 | −18.987 | 4.85 | | |
| 48 | ∞ | 4.85 | | |
| 49 | 18.987 | 28.71 | 1.7725 | 49.6 |
| 50 | ∞ | 0.78 | | |
| 51 | 24.668 | 5.81 | 1.497 | 81.55 |
| 52 | −7.75 | 2.65 | 1.7725 | 49.6 |
| 53 | −14.732 | 2.52 | | |
| 54 | 14.732 | 2.65 | 1.7725 | 49.6 |
| 55 | 7.75 | 5.81 | 1.497 | 81.55 |
| 56 | −24.668 | 0.78 | | |
| 57 | ∞ | 28.71 | 1.7725 | 49.6 |
| 58 | −18.987 | 4.85 | | |
| 59 | ∞ | 4.85 | | |
| 60 | 18.987 | 28.71 | 1.7725 | 49.6 |
| 61 | ∞ | 0.78 | | |
| 62 | 24.668 | 5.81 | 1.497 | 81.55 |
| 63 | −7.75 | 2.65 | 1.7725 | 49.6 |
| 64 | −14.732 | 2.52 | | |
| 65 | 14.732 | 2.65 | 1.7725 | 49.6 |
| 66 | 7.75 | 5.81 | 1.497 | 81.55 |
| 67 | −24.668 | 0.78 | | |
| 68 | ∞ | 28.71 | 1.7725 | 49.6 |
| 69 | −18.987 | 4.85 | | |
| 70 | ∞ | 4.63 | | |
| 71 | 19.01 | 28.82 | 1.7725 | 49.6 |
| 72 | ∞ | 0.88 | | |
| 73 | 24.958 | 5.9 | 1.497 | 81.55 |
| 74 | −7.765 | 2.67 | 1.7725 | 49.6 |
| 75 | −14.809 | 2.86 | | |
| 76 (Stop) | ∞ | 0.76 | | |
| 77 | ∞ | 2.62 | 1.8061 | 40.93 |
| 78 | ∞ | 6.7 | 1.8061 | 40.93 |
| 79 | ∞ | 2.62 | 1.8061 | 40.93 |
| 80 | ∞ | 1.44 | | |
| 81 | ∞ | 3.93 | 1.8061 | 40.93 |
| 82 | ∞ | 5.7 | 1.8061 | 40.93 |
| 83 | ∞ | 3.93 | 1.8061 | 40.93 |
| 84 | ∞ | 1.31 | | |
| 85 | 27.692 | 3.28 | 1.497 | 81.55 |
| 86 | −40.68 | 0.13 | | |
| 87 | 13.516 | 8.56 | 1.497 | 81.55 |
| 88 | 29.845 | 1.16 | | |
| 89 | −36.756 | 1.31 | 1.8 | 30.13 |
| 90 | 7.368 | 4.04 | | |
| 91 | 22.834 | 6.56 | 1.83481 | 42.71 |
| 92 | −14.2 | 10.77 | | |
| 93 | ∞ | 0.98 | 1.52113 | 66.54 |
| 94 | ∞ | 1.21 | | |
| 95 | ∞ | 0.69 | 1.51633 | 64.14 |
| 96 | ∞ | 0.00 | | |
| Image plane | ∞ | | | |

-continued

Unit mm

Aspherical surface data

3rd surface k = 0
A4 = 2.503.E−02, A6 = −5.6163.E−03, A8 = 5.5411.E−04

4th surface k = −0.9151
A4 = 1.431.E−01, A6 = −2.5790.E−02

Various data

| | | |
|---|---|---|
| IH | | 2.08 |
| f | | 3.00 |
| FNO. | | 5.1 |

Eccentricity data

77th surface

| X | Y | Z |
|---|---|---|
| 0.00 | −0.14 | 0.00 |
| α | β | γ |
| 0.0 | 0.0 | 0.0 |

78th surface

| X | Y | Z |
|---|---|---|
| 0.00 | 0.00 | 0.00 |
| α | β | γ |
| 45.0 | 0.0 | 0.0 |

79th surface

| X | Y | Z |
|---|---|---|
| 0.00 | 0.00 | 0.00 |
| α | β | γ |
| −45.0 | 0.0 | 0.0 |

82nd surface

| X | Y | Z |
|---|---|---|
| 0.00 | 0.00 | 0.00 |
| α | β | γ |
| −45.0 | 0.0 | 0.0 |

83rd surfaceV

| X | Y | Z |
|---|---|---|
| 0.00 | 0.00 | 0.00 |
| α | β | γ |
| 45.0 | 0.0 | 0.0 |

Example 4

Unit mm

Surface data

| Surface no. | r | d | nd | vd |
|---|---|---|---|---|
| 1 | ∞ | 1.34 | 1.769 | 64.15 |
| 2 | ∞ | 0.28 | | |
| 3* | ∞ | 1.67 | 1.8061 | 40.93 |
| 4* | 1.045 | 0.74 | | |
| 5 | ∞ | 14.83 | 1.883 | 40.77 |
| 6 | −8.471 | 1.87 | | |
| 7 | 26.698 | 2.68 | 1.72047 | 34.71 |
| 8 | 5.528 | 3.71 | 1.618 | 63.33 |
| 9 | −11.171 | 7.22 | | |
| 10 | −4.073 | 0.82 | 1.71736 | 29.52 |
| 11 | 5.911 | 2.29 | 1.883 | 40.77 |
| 12 | −12.125 | 0.82 | | |
| 13 | 18.21 | 3.73 | 1.7725 | 49.6 |
| 14 | 200.018 | 7.37 | | |
| 15 | ∞ | 5.15 | | |
| 16 | 20.15 | 30.47 | 1.7725 | 49.6 |
| 17 | ∞ | 0.83 | | |
| 18 | 26.144 | 6.16 | 1.497 | 81.55 |
| 19 | −8.219 | 2.81 | 1.7725 | 49.6 |
| 20 | −15.632 | 2.68 | | |
| 21 | 15.632 | 2.81 | 1.7725 | 49.6 |
| 22 | 8.219 | 6.16 | 1.497 | 81.55 |
| 23 | −26.144 | 0.83 | | |
| 24 | ∞ | 30.47 | 1.7725 | 49.6 |
| 25 | −20.15 | 5.15 | | |
| 26 | ∞ | 5.15 | | |
| 27 | 20.15 | 30.47 | 1.7725 | 49.6 |
| 28 | ∞ | 0.83 | | |
| 29 | 26.144 | 6.16 | 1.497 | 81.55 |
| 30 | −8.219 | 2.81 | 1.7725 | 49.6 |
| 31 | −15.632 | 2.68 | | |
| 32 | 15.632 | 2.81 | 1.7725 | 49.6 |
| 33 | 8.219 | 6.16 | 1.497 | 81.55 |
| 34 | −26.144 | 0.83 | | |
| 35 | ∞ | 30.47 | 1.7725 | 49.6 |
| 36 | −20.15 | 5.15 | | |
| 37 | ∞ | 5.15 | | |
| 38 | 20.15 | 30.47 | 1.7725 | 49.6 |
| 39 | ∞ | 0.83 | | |
| 40 | 26.144 | 6.16 | 1.497 | 81.55 |
| 41 | −8.219 | 2.81 | 1.7725 | 49.6 |
| 42 | −15.632 | 2.68 | | |
| 43 | 15.632 | 2.81 | 1.7725 | 49.6 |
| 44 | 8.219 | 6.16 | 1.497 | 81.55 |
| 45 | −26.144 | 0.83 | | |
| 46 | ∞ | 30.47 | 1.7725 | 49.6 |
| 47 | −20.15 | 5.15 | | |
| 48 | ∞ | 5.15 | | |
| 49 | 20.15 | 30.47 | 1.7725 | 49.6 |
| 50 | ∞ | 0.83 | | |
| 51 | 26.144 | 6.16 | 1.497 | 81.55 |
| 52 | −8.219 | 2.81 | 1.7725 | 49.6 |
| 53 | −15.632 | 2.68 | | |
| 54 | 15.632 | 2.81 | 1.7725 | 49.6 |
| 55 | 8.219 | 6.16 | 1.497 | 81.55 |
| 56 | −26.144 | 0.83 | | |
| 57 | ∞ | 30.47 | 1.7725 | 49.6 |
| 58 | −20.15 | 5.15 | | |
| 59 | ∞ | 5.15 | | |
| 60 | 20.15 | 30.47 | 1.7725 | 49.6 |
| 61 | ∞ | 0.83 | | |
| 62 | 26.144 | 6.16 | 1.497 | 81.55 |
| 63 | −8.219 | 2.81 | 1.7725 | 49.6 |
| 64 | −15.632 | 1.34 | | |
| 65 (Stop) | ∞ | 0.92 | | |
| 66 | ∞ | 4.52 | 1.8061 | 40.93 |
| 67 | ∞ | −9.04 | 1.8061 | 40.93 |
| 68 | ∞ | 4.52 | 1.8061 | 40.93 |
| 69 | ∞ | 3.48 | 1.8061 | 40.93 |
| 70 | ∞ | −6.96 | 1.8061 | 40.93 |
| 71 | ∞ | 3.48 | 1.8061 | 40.93 |

-continued

Unit mm

| | | | | |
|---|---|---|---|---|
| 72 | ∞ | 0.7 | | |
| 73 | 28.914 | 4.07 | 1.497 | 81.55 |
| 74 | −11.809 | 0.7 | 1.52944 | 51.72 |
| 75 | −549.99 | 0.14 | | |
| 76 | 11.209 | 8.68 | 1.497 | 81.55 |
| 77 | 31.598 | 1.65 | | |
| 78 | −296.255 | 1.39 | 1.80071 | 34.71 |
| 79 | 7.134 | 4.35 | | |
| 80 | 20.476 | 4.08 | 1.83481 | 42.73 |
| 81 | −15.75 | 10 | | |
| 82 | ∞ | 1.04 | 1.51633 | 64.14 |
| 83 | ∞ | 0.52 | | |
| 84 | ∞ | 0.73 | 1.51633 | 64.14 |
| 85 | ∞ | 1.24 | | |
| Image plane | ∞ | | | |

Aspherical surface data

3rd surface k = 0
A4 = 1.853.E−02, A6 = −4.0183.E−03, A8 = 3.4921.E−04

4th surface k = −0.9892
A4 = 1.030.E−01, A6 = −1.9170.E−02

Various data

| IH | 2.37 |
|---|---|
| f | 3.00 |
| FNO. | 4.8 |

Eccentricity data

66th surface

| X | Y | Z |
|---|---|---|
| 0.00 | −0.20 | 0.00 |

| α | β | γ |
|---|---|---|
| 0.0 | 0.0 | 0.0 |

67th surface

| X | Y | Z |
|---|---|---|
| 0.00 | 0.00 | 0.00 |

| α | β | γ |
|---|---|---|
| 45.0 | 0.0 | 0.0 |

68th surface

| X | Y | Z |
|---|---|---|
| 0.00 | 0.00 | 0.00 |

| α | β | γ |
|---|---|---|
| −45.0 | 0.0 | 0.0 |

70th surface

| X | Y | Z |
|---|---|---|
| 0.00 | 0.00 | 0.00 |

| α | β | γ |
|---|---|---|
| −45.0 | 0.0 | 0.0 |

-continued

Unit mm

71st surface

| X | Y | Z |
|---|---|---|
| 0.00 | 0.00 | 0.00 |

| α | β | γ |
|---|---|---|
| 45.0 | 0.0 | 0.0 |

Example 5

Unit mm

Surface data

| Surface no. | r | d | nd | vd |
|---|---|---|---|---|
| 1 | ∞ | 0.59 | 1.769 | 64.15 |
| 2 | ∞ | 0.29 | | |
| 3* | ∞ | 1.7 | 1.80625 | 40.91 |
| 4* | 1.107 | 0.78 | | |
| 5 | ∞ | 15.7 | 1.883 | 40.77 |
| 6 | −8.972 | 1.98 | | |
| 7 | 28.276 | 2.84 | 1.72047 | 34.71 |
| 8 | 5.854 | 3.93 | 1.618 | 63.33 |
| 9 | −11.831 | 7.65 | | |
| 10 | −4.314 | 0.86 | 1.71736 | 29.52 |
| 11 | 6.261 | 2.42 | 1.883 | 40.77 |
| 12 | −12.841 | 0.87 | | |
| 13 | 19.287 | 3.95 | 1.7725 | 49.6 |
| 14 | 211.841 | 7.8 | | |
| 15 | ∞ | 5.45 | | |
| 16 | 21.342 | 32.27 | 1.7725 | 49.6 |
| 17 | ∞ | 0.88 | | |
| 18 | 27.69 | 6.53 | 1.497 | 81.55 |
| 19 | −8.704 | 2.98 | 1.7725 | 49.6 |
| 20 | −16.556 | 2.84 | | |
| 21 | 16.556 | 2.98 | 1.7725 | 49.6 |
| 22 | 8.704 | 6.53 | 1.497 | 81.55 |
| 23 | −27.69 | 0.88 | | |
| 24 | ∞ | 32.27 | 1.7725 | 49.6 |
| 25 | −21.342 | 5.45 | | |
| 26 | ∞ | 5.45 | | |
| 27 | 21.342 | 32.27 | 1.7725 | 49.6 |
| 28 | ∞ | 0.88 | | |
| 29 | 27.69 | 6.53 | 1.497 | 81.55 |
| 30 | −8.704 | 2.98 | 1.7725 | 49.6 |
| 31 | −16.556 | 2.84 | | |
| 32 | 16.556 | 2.98 | 1.7725 | 49.6 |
| 33 | 8.704 | 6.53 | 1.497 | 81.55 |
| 34 | −27.69 | 0.88 | | |
| 35 | ∞ | 32.27 | 1.7725 | 49.6 |
| 36 | −21.342 | 5.45 | | |
| 37 | ∞ | 5.45 | | |
| 38 | 21.342 | 32.27 | 1.7725 | 49.6 |
| 39 | ∞ | 0.88 | | |
| 40 | 27.69 | 6.53 | 1.497 | 81.55 |
| 41 | −8.704 | 2.98 | 1.7725 | 49.6 |
| 42 | −16.556 | 2.84 | | |
| 43 | 16.556 | 2.98 | 1.7725 | 49.6 |
| 44 | 8.704 | 6.53 | 1.497 | 81.55 |
| 45 | −27.69 | 0.88 | | |
| 46 | ∞ | 32.27 | 1.7725 | 49.6 |
| 47 | −21.342 | 5.45 | | |
| 48 | ∞ | 5.45 | | |
| 49 | 21.342 | 32.27 | 1.7725 | 49.6 |
| 50 | ∞ | 0.88 | | |
| 51 | 27.69 | 6.53 | 1.497 | 81.55 |
| 52 | −8.704 | 2.98 | 1.7725 | 49.6 |
| 53 | −16.556 | 2.84 | | |
| 54 | 16.556 | 2.98 | 1.7725 | 49.6 |
| 55 | 8.704 | 6.53 | 1.497 | 81.55 |
| 56 | −27.69 | 0.88 | | |
| 57 | ∞ | 32.27 | 1.7725 | 49.6 |

-continued

| | Unit mm | | | |
|---|---|---|---|---|
| 58 | −21.342 | 5.45 | | |
| 59 | ∞ | 5.45 | | |
| 60 | 21.342 | 32.27 | 1.7725 | 49.6 |
| 61 | ∞ | 0.88 | | |
| 62 | 27.69 | 6.53 | 1.497 | 81.55 |
| 63 | −8.704 | 2.98 | 1.7725 | 49.6 |
| 64 | −16.556 | 2.84 | | |
| 65 | 16.556 | 2.98 | 1.7725 | 49.6 |
| 66 | 8.704 | 6.53 | 1.497 | 81.55 |
| 67 | −27.69 | 0.88 | | |
| 68 | ∞ | 32.27 | 1.7725 | 49.6 |
| 69 | −21.342 | 1.03 | | |
| 70 | ∞ | 3.5 | 1.80609 | 40.93 |
| 71 | ∞ | 7 | 1.80609 | 40.93 |
| 72 | ∞ | 3.5 | 1.80609 | 40.93 |
| 73 | ∞ | 0.44 | | |
| 74 | −45.208 | 3.73 | 1.7725 | 49.6 |
| 75 | −25.148 | 6.18 | | |
| 76 | 18.856 | 12.76 | 1.8044 | 39.59 |
| 77 | 9.579 | 0.74 | | |
| 78 | 11.375 | 14.74 | 1.497 | 81.55 |
| 79 | −13.7 | 2.95 | 1.8044 | 39.59 |
| 80 | −15.793 | 0.15 | | |
| 81 (Stop) | ∞ | 0.15 | | |
| 82 | 15.793 | 2.95 | 1.8044 | 39.59 |
| 83 | 13.7 | 14.74 | 1.497 | 81.55 |
| 84 | −11.375 | 0.74 | | |
| 85 | −9.579 | 12.76 | 1.8044 | 39.59 |
| 86 | −18.856 | 6.18 | | |
| 87 | 25.148 | 3.73 | 1.7725 | 49.6 |
| 88 | 45.208 | 0.44 | | |
| 89 | ∞ | 3.09 | 1.80609 | 40.93 |
| 90 | ∞ | 7.5 | 1.80609 | 40.93 |
| 91 | ∞ | 3.09 | 1.80609 | 40.93 |
| 92 | ∞ | 0.47 | | |
| 93 | ∞ | 1.03 | 1.51633 | 64.14 |
| 94 | ∞ | 0 | | |
| Image plane | ∞ | | | |

Aspherical surface data

3rd surface k = 0
A4 = 1.726.E−02, A6 = −3.0368.E−03, A8 = 1.9675.E−04

4th surface k = −0.2024
A4 = 7.203.E−03, A6 = 1.4297.E−02, A8 = −5.5253.E−02

Various data

| | |
|---|---|
| IH | 2.36 |
| f | 3.00 |
| FNO. | 4.1 |

Eccentricity data

70th surface

| X | Y | Z |
|---|---|---|
| 0.00 | −0.17 | 0.00 |

| α | β | γ |
|---|---|---|
| 0.0 | 0.0 | 0.0 |

71st surface

| X | Y | Z |
|---|---|---|
| 0.00 | 0.00 | 0.00 |

-continued

| | Unit mm | |
|---|---|---|
| α | β | γ |
| 45.0 | 0.0 | 0.0 |

72nd surface

| X | Y | Z |
|---|---|---|
| 0.00 | 0.00 | 0.00 |

| α | β | γ |
|---|---|---|
| −45.0 | 0.0 | 0.0 |

90th surface

| X | Y | Z |
|---|---|---|
| 0.00 | 0.00 | 0.00 |

| α | β | γ |
|---|---|---|
| −45.0 | 0.0 | 0.0 |

91st surface

| X | Y | Z |
|---|---|---|
| 0.00 | 0.00 | 0.00 |

| α | β | γ |
|---|---|---|
| 45.0 | 0.0 | 0.0 |

Example 6

| | Unit mm | | |
|---|---|---|---|
| | Surface data | | |
| Surface no. | r | d | nd | νd |
|---|---|---|---|---|
| 1 | ∞ | 0.52 | 1.769 | 64.15 |
| 2 | ∞ | 0.26 | | |
| 3* | ∞ | 1.4 | 1.80625 | 40.91 |
| 4* | 0.969 | 0.68 | | |
| 5 | ∞ | 13.74 | 1.883 | 40.77 |
| 6 | −7.85 | 1.74 | | |
| 7 | 24.74 | 2.48 | 1.72047 | 34.71 |
| 8 | 5.122 | 3.44 | 1.618 | 63.33 |
| 9 | −10.352 | 6.69 | | |
| 10 | −3.774 | 0.76 | 1.71736 | 29.52 |
| 11 | 5.478 | 2.12 | 1.883 | 40.77 |
| 12 | −11.235 | 0.76 | | |
| 13 | 16.875 | 3.45 | 1.7725 | 49.6 |
| 14 | 185.349 | 6.83 | | |
| 15 | ∞ | 4.77 | | |
| 16 | 18.673 | 28.23 | 1.7725 | 49.6 |
| 17 | ∞ | 0.77 | | |
| 18 | 24.227 | 5.71 | 1.497 | 81.55 |
| 19 | −7.616 | 2.61 | 1.7725 | 49.6 |
| 20 | −14.486 | 2.48 | | |
| 21 | 14.486 | 2.61 | 1.7725 | 49.6 |
| 22 | 7.616 | 5.71 | 1.497 | 81.55 |
| 23 | −24.227 | 0.77 | | |
| 24 | ∞ | 28.23 | 1.7725 | 49.6 |
| 25 | −18.673 | 4.77 | | |
| 26 | ∞ | 4.77 | | Relay image |
| 27 | 18.673 | 28.23 | 1.7725 | 49.6 |
| 28 | ∞ | 0.77 | | |
| 29 | 24.227 | 5.71 | 1.497 | 81.55 |
| 30 | −7.616 | 2.61 | 1.7725 | 49.6 |
| 31 | −14.486 | 2.48 | | |

-continued

Unit mm

| | | | | |
|---|---|---|---|---|
| 32 | 14.486 | 2.61 | 1.7725 | 49.6 |
| 33 | 7.616 | 5.71 | 1.497 | 81.55 |
| 34 | −24.227 | 0.77 | | |
| 35 | ∞ | 28.23 | 1.7725 | 49.6 |
| 36 | −18.673 | 4.77 | | |
| 37 | ∞ | 4.77 | | Relay image |
| 38 | 18.673 | 28.23 | 1.7725 | 49.6 |
| 39 | ∞ | 0.77 | | |
| 40 | 24.227 | 5.71 | 1.497 | 81.55 |
| 41 | −7.616 | 2.61 | 1.7725 | 49.6 |
| 42 | −14.486 | 2.48 | | |
| 43 | 14.486 | 2.61 | 1.7725 | 49.6 |
| 44 | 7.616 | 5.71 | 1.497 | 81.55 |
| 45 | −24.227 | 0.77 | | |
| 46 | ∞ | 28.23 | 1.7725 | 49.6 |
| 47 | −18.673 | 4.77 | | |
| 48 | ∞ | 4.77 | | |
| 49 | 18.673 | 28.23 | 1.7725 | 49.6 |
| 50 | ∞ | 0.77 | | |
| 51 | 24.227 | 5.71 | 1.497 | 81.55 |
| 52 | −7.616 | 2.61 | 1.7725 | 49.6 |
| 53 | −14.486 | 2.48 | | |
| 54 | 14.486 | 2.61 | 1.7725 | 49.6 |
| 55 | 7.616 | 5.71 | 1.497 | 81.55 |
| 56 | −24.227 | 0.77 | | |
| 57 | ∞ | 28.23 | 1.7725 | 49.6 |
| 58 | −18.673 | 4.77 | | |
| 59 | ∞ | 4.77 | | |
| 60 | 18.673 | 28.23 | 1.7725 | 49.6 |
| 61 | ∞ | 0.77 | | |
| 62 | 24.227 | 5.71 | 1.497 | 81.55 |
| 63 | −7.616 | 2.61 | 1.7725 | 49.6 |
| 64 | −14.486 | 2.48 | | |
| 65 | 14.486 | 2.61 | 1.7725 | 49.6 |
| 66 | 7.616 | 5.71 | 1.497 | 81.55 |
| 67 | −24.227 | 0.77 | | |
| 68 | ∞ | 28.23 | 1.7725 | 49.6 |
| 69 | −18.673 | 1.55 | | |
| 70 | ∞ | 3.22 | 1.8061 | 40.93 |
| 71 | ∞ | 6.45 | 1.8061 | 40.93 |
| 72 | ∞ | 3.22 | 1.8061 | 40.93 |
| 73 | ∞ | 0.26 | | |
| 74 | 197.104 | 1.93 | 1.7725 | 49.6 |
| 75 | −13.281 | 0.13 | | |
| 76 | 7.314 | 3.87 | 1.755 | 52.32 |
| 77 | 4.897 | 1.03 | | |
| 78 | 6.845 | 5.16 | 1.497 | 81.55 |
| 79 | −12.894 | 1.93 | 1.8322 | 40.1 |
| 80 | −17.148 | 0.64 | | |
| 81 (Stop) | ∞ | 0.64 | | |
| 82 | 9.776 | 1.93 | 1.8322 | 40.1 |
| 83 | 5.632 | 5.16 | 1.497 | 81.55 |
| 84 | −9.044 | 0.14 | | |
| 85 | 18.148 | 1.93 | 1.7725 | 49.6 |
| 86 | 209.051 | 0.26 | | |
| 87 | ∞ | 3.48 | 1.8061 | 40.93 |
| 88 | ∞ | 7.74 | 1.8061 | 40.93 |
| 89 | ∞ | 3.48 | 1.8061 | 40.93 |
| 90 | ∞ | 0.13 | | |
| 91 | ∞ | 0.9 | 1.51633 | 64.14 |
| 92 | ∞ | 0.4231 | | |
| Image plane | ∞ | | | |

Aspherical surface data

3rd surface k = 0
A4 = 2.577.E−02, A6 = −5.9225.E−03, A8 = 5.0125.E−04

4th surface k = −0.2024
A4 = 1.076.E−02, A6 = 2.7883.E−02, A8 = −1.4076.E−01

-continued

Unit mm

Various data

| | |
|---|---|
| IH | 2.33 |
| f | 3.00 |
| FNO. | 4.7 |

70th surface

| X | Y | Z |
|---|---|---|
| 0.00 | −0.14 | 0.00 |

| α | β | γ |
|---|---|---|
| 0.0 | 0.0 | 0.0 |

71st surface

| X | Y | Z |
|---|---|---|
| 0.00 | 0.00 | 0.00 |

| α | β | γ |
|---|---|---|
| 45.0 | 0.0 | 0.0 |

73rd surface

| X | Y | Z |
|---|---|---|
| 0.00 | 0.00 | 0.00 |

| α | β | γ |
|---|---|---|
| −45.0 | 0.0 | 0.0 |

88th surface

| X | Y | Z |
|---|---|---|
| 0.00 | 0.00 | 0.00 |

| α | β | γ |
|---|---|---|
| −45.0 | 0.0 | 0.0 |

89th surface

| X | Y | Z |
|---|---|---|
| 0.00 | 0.00 | 0.00 |

| α | β | γ |
|---|---|---|
| 45.0 | 0.0 | 0.0 |

Next, values of conditional expressions in each example are given below. '-' (hyphen) indicates that there is no corresponding arrangement. FLG1 in conditional expression (14) may be considered as an object side focal length.

| | Example 1 | Example 2 | Example 3 |
|---|---|---|---|
| (3) \|divlr\|/Yimgh | 0.34 | 0.27 | 0.52 |
| (4) βh | −1.50 | −1.20 | −1.16 |
| (5) βv | −1.50 | −1.20 | −1.16 |
| (6) βh/βv | 1.00 | 1.00 | 1.00 |
| (7) Φpri2in/Φpri2ex | 1.07 | 1.00 | — |
| (8) Φpri1in/Φpri2ex | — | — | 0.98 |
| (9) DG2b/FLG2 | 1.29 | 1.00 | 1.02 |
| (10) Yimg/FLG2 | 0.08 | 0.11 | 0.08 |
| (11) βG1h | — | — | — |
| (12) βG1v | — | — | — |
| (13) βG1h/βG1v | — | — | — |

-continued

|  | Example 1 | Example 2 | Example 3 |
|---|---|---|---|
| (14) DG1f/FLG1 | 0.81 | 1.00 | 0.99 |
| (15) Yimg/FLG1 | 0.10 | 0.13 | 0.09 |
| (16) Dax1/(Φrmax + Dax1) | 0.53 | 0.53 | 0.54 |
| (17) Φrmax/Ymidimg | 2.93 | 2.55 | 2.46 |

|  | Example 4 | Example 5 | Example 6 |
|---|---|---|---|
| (3) \|divlr\|/Yimgh | 1.11 | 0.33 | 0.62 |
| (4) βh | −1.09 | — | — |
| (5) βv | −1.09 | — | — |
| (6) βh/βv | 1.00 | — | — |
| (7) Φpri2in/Φpri2ex | — | — | — |
| (8) Φpri1in/Φpri2ex | 0.63 | — | — |
| (9) DG2b/FLG2 | 1.00 | — | — |
| (10) Yimg/FLG2 | 0.09 | — | — |
| (11) βG1h | — | −1.04 | −1.19 |
| (12) βG1v | — | −1.04 | −1.19 |
| (13) βG1h/βG1v | — | 1.00 | 1.00 |
| (14) DG1f/FLG1 | 1.00 | 0.69 | 0.88 |
| (15) Yimg/FLG1 | 0.10 | 0.03 | 0.14 |
| (16) Dax1/(Φrmax + Dax1) | 0.59 | 0.54 | 0.53 |
| (17) Φrmax/Ymidimg | 3.03 | 2.67 | 2.85 |

Figure 24:
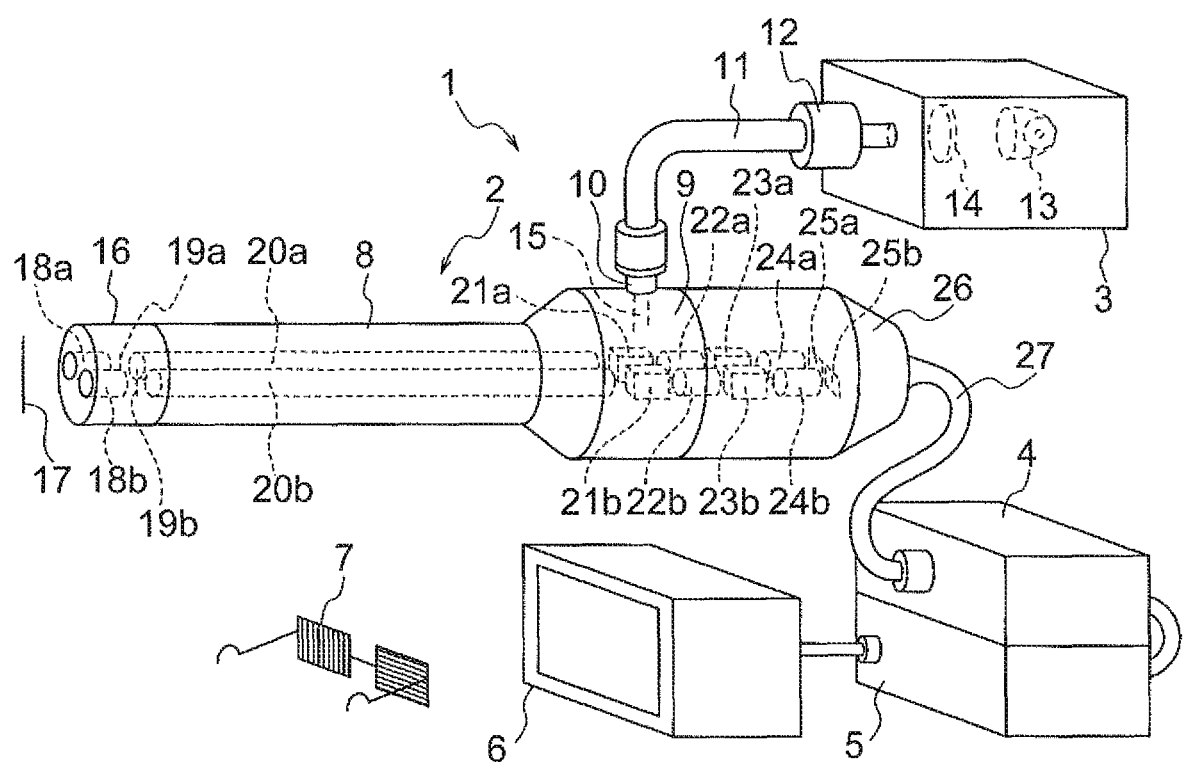
FIG. 24 is a diagram showing a stereoscopic vision endoscope according to the present embodiment.

FIG. 24 is a diagram showing the stereoscopic-vision endoscope of the present embodiment. A stereoscopic-vision endoscope 1 includes a body portion 2, a light-source unit 3, a camera control unit 4 (hereinafter, referred to as 'CCU 4'), a scan converter 5, a monitor 6, and shutter glasses 7.

The body portion 2 includes an insertion portion 8 and a holding portion 9. The insertion portion 8 is a portion to be inserted into a body cavity, and is formed by a hard jacket tube. The jacket tube is in the form of a circular tube, and is made of a metal such as stainless steel. In such manner, the stereoscopic-vision endoscope 1 is a rigid endoscope. The holding portion 9 is a portion to be held by an operator.

The holding portion 9 is provided with a light-guide tube 10. One end of a light-guide cable 11 is connected to the light-guide tube 10. The other end of the light-guide cable 11 is provided with alight-guide connector 12. The light-guide cable 11 is detachably connected to the holding portion 9 and the light-source unit 3.

The light-source unit 3 includes a lamp 13 and a lens 14. The lamp 13 generates illumination light such as white light. The lens 14 focuses the illumination light. The illumination light focused by the lens 14 is irradiated to an end surface of the light-guide connector 12. The illumination light irradiated to the end surface is transmitted to the body portion 2 by a light guide inside the light-guide cable 11.

The body portion 2 is provided with a light guide 15. The light guide 15 is bent inside the holding portion 9, and is passed through the insertion portion 8. The light guide 15 transmits the illumination light supplied from the light-guide cable 11 to a front-end surface which is fixed to a front-end portion 16 of the insertion portion 8. Accordingly, the illumination light is emerged frontward from the front-end surface.

An object 17 is illuminated by the illumination light. Light from the object 17 is incident on an objective optical system 18a and 18b which is disposed inside the front-end portion 16. An optical image I9a is formed at an image forming position of the objective optical system 18a. An optical image 19b is formed at an image forming position of the objective optical system 18b.

The optical image I9a is relayed to the holding portion 9 by a relay optical system 20a. The optical image I9b is relayed to the holding portion 9 by a relay optical system 20b.

An intermediate image is formed at a final-image position of the relay optical systems 20a and 20b. The intermediate image formed by the relay optical system 20a is imaged once again by a first optical-path bending element 21a, a first lens unit 22a, a first optical-path bending element 23a, and a second lens unit 24a. Accordingly, a first image is formed on an image pickup surface of a first imager 25a.

The intermediate image formed by the relay optical system 20b is imaged once again by a first optical-path bending element 21b, a first lens unit 22b, a first optical-path bending element 23b, and a second lens unit 24b. Accordingly, a second image is formed on an image pickup surface of a second imager 25b.

One end of a signal cable 27 is connected to an output portion 26. The other end of the signal cable 27 is connected to the CCU 4. A signal which is output from the first image pickup element 25a and a signal which is output from the second image pickup element 25b are input to the CCU 4 via the signal cable 27.

In the CCU 4, signal processing is carried out on signals output from the first image pickup element 25a and the second image pickup element 25b. An image signal subjected to signal processing in the CCU 4 is input to the scan converter 5. In the scan converter 5, the signal output from the CCU 4 is converted to a video signal.

The video signal is input to the monitor 6. The monitor 6 displays the video signal that has been input. Two images having a parallax are displayed alternately on the monitor 6. The shutter glasses 7 have a shutter function. By using the shutter glasses 7, images displayed on the monitor 6 can be viewed stereoscopically.

In FIG. 24, shapes of the first optical-path bending elements 21a and 21b and shapes of the second optical-path bending elements 23a and 23b are drawn as simplified shapes. Therefore, an optical path from the first optical-path bending element 21a up to the first imager 25a and an optical path from the second optical-path bending element 21b up to the second imager 25b are drawn in straight lines.

However, practically, due to the first optical-path bending elements 21a and 21b and the second optical-path bending elements 23a and 23b, the optical paths are not straight lines as mentioned above.

According to the present embodiment, it is possible to provide a stereoscopic-vision endoscope optical system having a high resolution, while being small-sized, and an endoscope using the stereoscopic-vision endoscope optical system.

The present invention is suitable for a stereoscopic-vision endoscope optical system having a high resolution, while being small-sized, and an endoscope using the stereoscopic-vision endoscope optical system.

What is claimed is:

1. A stereoscopic-vision endoscope optical system, comprising:
    a first optical system; and
    a second optical system,
    wherein:
        the first optical system and the second optical system are identical optical systems,
        a first optical path, a second optical path, and a third optical path are formed in each of the first optical system and the second optical system, each of the first optical system and the second optical system includes, in order from an object side, an objective optical system, a relay optical system, and an image forming optical system, the image forming optical system includes a first lens unit, a first optical-path bending element, and a second optical-path bending element, a final image of an object is formed by the image forming optical system, the objective optical system and the relay optical system are disposed in the first optical path, the second optical path is formed between the first optical-path bending element and the second optical-path bending element, the third optical path is formed between the second optical-path bending element and the final image, the first optical-path bending element has a first reflecting surface disposed in the first optical path and a second reflecting surface disposed in the second optical path, the second optical-path bending element has a third reflecting surface disposed in the second optical path and a fourth reflecting surface disposed in the third optical path, a first optical axis of the first optical system, a second optical axis of the first optical system, a third optical axis of the first optical system, a first optical axis of the second optical system, a second optical axis of the second optical system, and a third optical axis of the second optical system are all positioned in a same plane, and the following conditional expressions (1), (2), and (3) are satisfied:

D1<D2 (1)
D3<D2 (2)
0.01≤|div1r|/Yimgh≤1.5 (3)

where,

D1 denotes a distance between the first optical axis of the first optical system and the first optical axis of the second optical system, D2 denotes a distance between the second optical axis of the first optical system and the second optical axis of the second optical system, D3 denotes a distance between the third optical axis of the first optical system and the third optical axis of the second optical system, div1r denotes a distance between the first optical axis and a center of the final image, and Yimgh denotes a height of the final image in a parallax direction, and here the first optical axis of the first optical system is an optical axis of the first optical path of the first optical system, the second optical axis of the first optical system is an optical axis of the second optical path of the first optical system, the third optical axis of the first optical system is an optical axis of the third optical path of the first optical system, the first optical axis of the second optical system is an optical axis of the first optical path of the second optical system, the second optical axis of the second optical system is an optical axis of the second optical path of the second optical system, the third optical axis of the second optical system is an optical axis of the third optical path of the second optical system, the unit of distance is millimeter, and the parallax direction is a direction orthogonal to both the first optical axis of the first optical system and the first optical axis of the second optical system.

2. An endoscope comprising:
the stereoscopic-vision endoscope optical system according to claim 1; and
an imager configured to pick up the final image.

3. A stereoscopic-vision endoscope optical system comprising:
a first optical system; and
a second optical system,
wherein:
the first optical system and the second optical system are identical optical systems, a first optical path, a second optical path, and a third optical path are formed in each of the first optical system and the second optical system, each of the first optical system and the second optical system includes, in order from an object side, an objective optical system, a relay optical system, and an image forming optical system, the image forming optical system includes a first lens unit, a first optical-path bending element, and a second optical-path bending element, a final image of an object is formed by the image forming optical system, the objective optical system and the relay optical system are disposed in the first optical path, the second optical path is formed between the first optical-path bending element and the second optical-path bending element, the third optical path is formed between the second optical-path bending element and the final image, the first optical-path bending element has a first reflecting surface disposed in the first optical path and a second reflecting surface disposed in the second optical path, the second optical-path bending element has a third reflecting surface disposed in the second optical path and a fourth reflecting surface disposed in the third optical path, a first optical axis of the first optical system, a second optical axis of the first optical system, a third optical axis of the first optical system, a first optical axis of the second optical system, a second optical axis of the second optical system, and a third optical axis of the second optical system are all positioned in a same plane, the image forming optical system includes, in order from the object side, the first optical-path bending element, the first lens unit, the second optical-path bending element, and a second lens unit, each of the first lens unit and the second lens unit has a positive refractive power, and the following conditional expressions (1), (2), (4), (5), and (6) are satisfied:

D1<D2 (1)
D3<D2 (2)
βh≤−1 (4)
βv≤−1 (5)
0.9≤βh/βv≤1.1 (6)

where,

D1 denotes a distance between the first optical axis of the first optical system and the first optical axis of the second optical system, D2 denotes a distance between the second optical axis of the first optical system and the second optical axis of the second optical system, D3 denotes a distance between the third optical axis of the first optical system and the third optical axis of the second optical system, βh denotes a combined magnification of the first lens unit and the second lens unit in a first direction, and βv denotes a combined magnification of the first lens unit and the second lens unit in a second direction, and here the first optical axis of the first optical system is an optical axis of the first optical path of the first optical system, the second optical axis of the first optical system is an optical axis of the second optical path of the first optical system, the third optical axis of the first optical system is an optical axis of the third optical path of the first optical system, the first optical axis of the second optical system is an optical axis of the first optical path of the second optical system, the second optical axis of the second optical system is an optical axis of the second optical path of the second optical system, the third optical axis of the second optical system is an optical axis of the third optical path of the second optical system, the unit of distance is millimeter, the first direction is a parallax direction, the second direction is a direction perpendicular to the parallax direction, and the parallax direction is a direction orthogonal to both the first optical axis of the first optical system and the first optical axis of the second optical system.

4. The stereoscopic-vision endoscope optical system according to claim 3, wherein:

the second optical-path bending element is a prism having a surface of incidence and a surface of emergence, light reaching the second optical-path bending element travels in order through the surface of incidence, the third reflecting surface, the fourth reflecting surface, and the surface of emergence, and the following conditional expression (7) is satisfied:

0.8 Φpri2in/Φpri2ex≤1.3 (7)

where,

Φpri2in denotes an effective diameter of the surface of incidence of the second optical-path bending element, and Φpri2ex denotes an effective diameter of the surface of emergence of the second optical-path bending element.

5. The stereoscopic-vision endoscope optical system according to claim 3, wherein the following conditional expression (9) is satisfied:

0.8 DG2b/FLG2≤1.5 (9)

where,

DG2b denotes a distance from an image-side principal point of the second lens unit up to the final image, and FLG2 denotes a focal length of the second lens unit.

6. The stereoscopic-vision endoscope optical system according to claim 3, wherein the following conditional expression (10) is satisfied:

0.02 Yimg/FLG2≤0.2 (10)

where,

Yimg denotes the maximum height of the final image, and

FLG2 denotes a focal length of the second lens unit.

7. The stereoscopic-vision endoscope optical system according to claim 3, wherein:

an intermediate image of an object is formed on an image side of the relay optical system, and the following conditional expression (14) is satisfied:

0.6≤DG1f/FLG1≤1.2 (14)

where,

DG1f denotes a distance from an object-side principal point of the first lens unit up to the intermediate image, and FLG1 denotes a focal length of the first lens unit.

8. The stereoscopic-vision endoscope optical system according to claim 3, wherein the following conditional expression (15) is satisfied:

0<Yimg/FLG1≤0.3 (15)

where,

Yimg denotes the maximum height of the final image, and

FLG1 denotes a focal length of the first lens unit.

9. The stereoscopic-vision endoscope optical system according to claim 3, wherein the following conditional expression (16) is satisfied:

0.3 Dax1/(Φrmax+Dax1)≤0.8 (16)

where,

Dax1 denotes a distance between the first optical axis of the first optical system and the first optical axis of the second optical system, and Φrmax denotes the maximum lens diameter in the relay optical system.

10. The stereoscopic-vision endoscope optical system according to claim 3, wherein:

an image of an object is formed on the object side of the relay optical system, by the objective optical system, and the following conditional expression (17) is satisfied:

1.0≤Φrmax/Ymidimg≤5.0 (17)

where,

Φrmax denotes the maximum lens diameter in the relay optical system, and

Ymidimg denotes the maximum height of the image of the object.

11. The stereoscopic-vision endoscope optical system according to claim 3, wherein:

the first lens unit includes a movable lens unit, and focusing is carried out by moving the movable lens unit.

12. The stereoscopic-vision endoscope optical system according to claim 3, wherein:

the second lens unit includes a movable lens unit, and focusing is carried out by moving the movable lens unit.

13. A stereoscopic-vision endoscope optical system comprising:

a first optical system; and a second optical system, wherein:

the first optical system and the second optical system are identical optical systems, a first optical path, a second optical path, and a third optical path are formed in each of the first optical system and the second optical system, each of the first optical system and the second optical system includes, in order from an object side, an objective optical system, a relay optical system, and an image forming optical system, the image forming optical system includes a first lens unit, a first optical-path bending element, and a second optical-path bending element, a final image of an object is formed by the image forming optical system, the objective optical system and the relay optical system are disposed in the first optical path, the second optical path is formed between the first optical-path bending element and the second optical-path bending element, the third optical path is formed between the second optical-path bending element and the final image, the first optical-path bending element has a first reflecting surface disposed in the first optical path and a second reflecting surface disposed in the second optical path, the second optical-path bending element has a third reflecting surface disposed in the second optical path and a fourth reflecting surface disposed in the third optical path, a first optical axis of the first optical system, a second optical axis of the first optical system, a third optical axis of the first optical system, a first optical axis of the second optical system, a second optical axis of the second optical system, and a third optical axis of the second optical system are all positioned in a same plane, the image forming optical system includes, in order from the object side, the first lens unit, the first optical-path bending element, the second optical-path bending element, and a second lens unit, each of the first lens unit and the second lens unit has a positive refractive power, and the following conditional expressions (1), (2), (4), (5), and (6) are satisfied:

D1<D2 (1)
D3<D2 (2)
$\beta h \leq -1$ (4)
$\beta v \leq -1$ (5)
$0.9 \leq \beta h/\beta y$ 1.1 (6)

where,

D1 denotes a distance between the first optical axis of the first optical system and the first optical axis of the second optical system, D2 denotes a distance between the second optical axis of the first optical system and the second optical axis of the second optical system, D3 denotes a distance between the third optical axis of the first optical system and the third optical axis of the second optical system, βh denotes a combined magnification of the first lens unit and the second lens unit in a first direction, and βv denotes a combined magnification of the first lens unit and the second lens unit in a second direction, and here the first optical axis of the first optical system is an optical axis of the first optical path of the first optical system, the second optical axis of the first optical system is an optical axis of the second optical path of the first optical system, the third optical axis of the first optical system is an optical axis of the third optical path of the first optical system, the first optical axis of the second optical system is an optical axis of the first optical path of the second optical system, the second optical axis of the second optical system is an optical axis of the second optical path of the second optical system, the third optical axis of the second optical system is an optical axis of the third optical path of the second optical system, the unit of distance is millimeter, the first direction is a parallax direction, the second direction is a direction perpendicular to the parallax direction, and the parallax direction is a direction orthogonal to both the first optical axis of the first optical system and the first optical axis of the second optical system.

14. The stereoscopic-vision endoscope optical system according to claim 13, wherein:

the first optical-path bending element is a prism having a surface of incidence and a surface of emergence, the second optical-path bending element is a prism having a surface of incidence and a surface of emergence, light reaching the first optical-path bending element travels in order through the surface of incidence of the first optical-path bending element, the first reflecting surface, the second reflecting surface, and the surface of emergence of the first optical-path bending element, light reaching the second optical-path bending element travels in order through the surface of incidence of the second optical-path bending element, the third reflecting surface, the fourth reflecting surface, and the surface of emergence of the second optical-path bending element, and the following conditional expression (8) is satisfied:

0.3 $\Phi pri1in/\Phi pri2ex \leq 1.3$ (8)

where, $\Phi pri1$ in denotes an effective diameter of the surface of incidence of the first optical-path bending element, and $\Phi pri2ex$ denotes an effective diameter of the surface of emergence of the second optical-path bending element.

15. The stereoscopic-vision endoscope optical system according to claim 13, wherein the following conditional expression (9) is satisfied:

$0.8 \leq DG2b/FLG2 \leq 1.5$ (9)

where,

DG2b denotes a distance from an image-side principal point of the second lens unit up to the final image, and FLG2 denotes a focal length of the second lens unit.

16. The stereoscopic-vision endoscope optical system according to claim 13, wherein the following conditional expression (10) is satisfied:

$0.02 \leq Yimg/FLG2 \leq 0.2$ (10)

where,

Yimg denotes the maximum height of the final image, and

FLG2 denotes a focal length of the second lens unit.

17. The stereoscopic-vision endoscope optical system according to claim 13, wherein:

an intermediate image of an object is formed on an image side of the relay optical system, and the following conditional expression (14) is satisfied:

0.6 $DG1f/FLG1 \leq 1.2$ (14)

where,

DG1f denotes a distance from an object-side principal point of the first lens unit up to the intermediate image, and FLG1 denotes a focal length of the first lens unit.

18. The stereoscopic-vision endoscope optical system according to claim 13, wherein:

the second lens unit includes a movable lens unit, and focusing is carried out by moving the movable lens unit.

19. A stereoscopic-vision endoscope optical system comprising:

a first optical system; and a second optical system, wherein:

the first optical system and the second optical system are identical optical systems, a first optical path, a second optical path, and a third optical path are formed in each of the first optical system and the second optical system, each of the first optical system and the second optical system includes, in order from an object side, an objective optical system, a relay optical system, and an image forming optical system, the image forming optical system includes a first lens unit, a first optical-path bending element, and a second optical-path bending element, a final image of an object is formed by the image forming optical system, the objective optical system and the relay optical system are disposed in the first optical path, the second optical path is formed between the first optical-path bending element and the second optical-path bending element, the third optical path is formed between the second optical-path bending element and the final image, the first optical-path bending element has a first reflecting surface disposed in the first optical path and a second reflecting surface disposed in the second optical path, the second optical-path bending element has a third reflecting surface disposed in the second optical path and a fourth reflecting surface disposed in the third optical path, a first optical axis of the first optical system, a second optical axis of the first optical system, a third optical axis of the first optical system, a first optical axis of the second optical system, a second optical axis of the second optical system, and a third optical axis of the second optical system are all positioned in a same plane, the image forming optical system includes, in order from the object side, the first optical-path bending element, the first lens unit, and the second optical-path bending element, the first lens unit has a positive refractive power, and the following conditional expressions (1), (2), (11), (12), and (13) are satisfied:

$D1<D2$ (1)
$D3<D2$ (2)
$\beta G1h \leq -1$ (11)
$\beta G1v \leq -1$ (12)
$0.9 \leq \beta G1h/\beta G1v \leq 1.1$ (13)

where,

D1 denotes a distance between the first optical axis of the first optical system and the first optical axis of the second optical system, D2 denotes a distance between the second optical axis of the first optical system and the second optical axis of the second optical system, D3 denotes a distance between the third optical axis of the first optical system and the third optical axis of the second optical system, $\beta G1h$ denotes a magnification of the first lens unit in a first direction, and $\beta G1v$ denotes a magnification of the first lens unit in a second direction, and here the first optical axis of the first optical system is an optical axis of the first optical path of the first optical system, the second optical axis of the first optical system is an optical axis of the second optical path of the first optical system, the third optical axis of the first optical system is an optical axis of the third optical path of the first optical system, the first optical axis of the second optical system is an optical axis of the first optical path of the second optical system, the second optical axis of the second optical system is an optical axis of the second optical path of the second optical system, the third optical axis of the second optical system is an optical axis of the third optical path of the second optical system, the unit of distance is millimeter, the first direction is the parallax direction, the second direction is a direction perpendicular to the parallax direction, and the parallax direction is a direction orthogonal to both the first optical axis of the first optical system and the first optical axis of the second optical system.

20. An endoscope comprising:

the stereoscopic-vision endoscope optical system according to claim 19; and an imager configured to pick up the final image.

* * * * *